(12) United States Patent
Aube et al.

(10) Patent No.: US 8,735,391 B2
(45) Date of Patent: May 27, 2014

(54) SYNTHESIS OF FUNCTIONALIZED OCTAHYDRO-ISOQUINOLIN-1-ONE-8-CARBOXAMIDES, OCTAHYDRO-ISOQUINOLIN-1-ONE-8-CARBOXYLIC ESTERS AND ANALOGS, AND THERAPEUTIC METHODS

(75) Inventors: Jeffrey Aube, Lawrence, KS (US);
Bryan L. Roth, Durham, NC (US);
Partha Ghosh, Lawrence, KS (US);
Kevin J. Frankowski, Lawrence, KS (US)

(73) Assignee: University of Kansas, Kansas City, KS (US)

( * ) Notice: Subject to any disclaimer, the term of this patent is extended or adjusted under 35 U.S.C. 154(b) by 169 days.

(21) Appl. No.: 12/567,573

(22) Filed: Sep. 25, 2009

(65) Prior Publication Data

US 2010/0256142 A1    Oct. 7, 2010

Related U.S. Application Data

(60) Provisional application No. 61/100,619, filed on Sep. 26, 2008.

(51) Int. Cl.
| | | |
|---|---|---|
| *A61K 31/535* | (2006.01) | |
| *A61K 31/497* | (2006.01) | |
| *A61K 31/4965* | (2006.01) | |
| *A61K 31/47* | (2006.01) | |

(52) U.S. Cl.
USPC .............. 514/235.2; 514/254.11; 514/255.05; 514/309; 514/320

(58) Field of Classification Search
None
See application file for complete search history.

(56) References Cited

U.S. PATENT DOCUMENTS 5,470,979 A    11/1995    Trova

FOREIGN PATENT DOCUMENTS

| WO | 99-31085 A1 | 6/1999 |
|---|---|---|
| WO | 2005-075431 A1 | 8/2005 |
| WO | 2005-123687 A1 | 12/2005 |

OTHER PUBLICATIONS

Heilbron et al (J Chem Soc 1945:84-87, 1945).*
STN Search Report (Accession No. 1945:17549).*
Stella et al (Prodrugs: Challenges and Rewards, Part 1, 2007).*
CAS RN 163488-73-1 (entered into STN Jun. 2, 1995).*
Frankowski et al (J Comb Chem 9:1188-1192, 2007—published online Sep. 27, 2007).*
STN Search Report ((Accession No. 2007:108861).*
International Search Report and Written Opinion dated May 7, 2010 as issued in PCT application PCT/US2009/058647 filed Sep. 28, 2009.

* cited by examiner

*Primary Examiner* — Craig Ricci
(74) *Attorney, Agent, or Firm* — Licata & Tyrrell P.C.

(57) ABSTRACT

A functionalized polycyclic compound can have a structure of Formula 1 or salt, prodrug, analog, or derivative thereof, which compound can be prepared by providing a diene; reacting the diene with a dienophile under sufficient conditions for a combined Diels-Alder/acylation reaction so as to provide a polycyclic compound having a carboxylic acid; and coupling the carboxylic acid with an amine-containing compound or a hydroxyl-containing compound so as to form an amide or an ester and producing a compound having a structure of Formula 1. The compound can be used for modulating an opioid receptor, which can be conducted by administering to an opioid receptor a functionalized polycyclic compound as described herein in an effective amount to modulate the functionality of the opioid receptor. Such opioid modulation can provide a biological benefit to a subject.

2 Claims, No Drawings

SYNTHESIS OF FUNCTIONALIZED OCTAHYDRO-ISOQUINOLIN-1-ONE-8-CARBOXAMIDES, OCTAHYDRO-ISOQUINOLIN-1-ONE-8-CARBOXYLIC ESTERS AND ANALOGS, AND THERAPEUTIC METHODS

CROSS-REFERENCE TO RELATED APPLICATIONS

This U.S. patent application claims benefit of U.S. provisional patent application having Ser. No. 61/100,619, filed on Sep. 26, 2008, which provisional application is incorporated herein by specific reference in its entirety.

GOVERNMENT SUPPORT

This invention was made with government support under Grant Nos. RO1DA017204 and P050-GM069663 awarded by the National Institutes of Health. The government has certain rights in the invention.

BACKGROUND OF THE INVENTION

Opioid receptors are a group of G-protein coupled receptors that have been identified to have opioids as ligands, which are about 70% identical with differences located at N and C termini of the receptors. Accordingly, opioid drugs have been developed to exploit the biological activity of activating these receptors. Examples of the opioid receptor types, subtypes, location, and agonist activation activities are shown in Table A below. It has been found that modulating the activity of the opioid receptors through an agonist or antagonist can have different therapeutic benefits. Various types of substances, ranging from small molecules through polypeptides, have been explored to identify new drugs that behave as agonists or antagonists of the opioid receptors.

TABLE A

| Receptor | Location | Function |
|---|---|---|
| delta (δ) $OP_1^{(?)}$ | Brain pontine nuclei amygdala olfactory bulbs deep cortex | analgesia antidepressant effects |
| kappa (κ) $OP_2^{(?)}$ | Brain hypothalamus periaqueductal gray claustrum Cortex Hippocampus spinal cord substantia gelatinosa | Spinal analgesia sedation miosis inhibition of ADH release |
| mu (μ) $OP_3^{(?)}$ | Brain cortex (laminae III and IV) thalamus striosomes periaqueductal gray spinal cord substantia gelatinosa | Supraspinal analgesia respiratory depression miosis euphoria reduced GI motility |
| Nociceptin receptor $OP_4$ | Brain cortex amygdala hippocampus septal nuclei habenula hypothalamus spinal cord | treat heart failure treat migraines appetite development of tolerance to μ agonists |

In addition to the activation of opioid receptors, inactivation or antagonism of opioid receptors by antagonists can also provide beneficial therapeutic effects. For example, a delta opioid receptor (DOR) antagonist may be useful for treatment for alcoholism and depression. A kappa opioid receptor (KOR) antagonist may be useful for a treatment for drug addiction, depression, inflammation, gastrointestinal, and renal diseases. A mu opioid receptor (MOR) antagonist may be useful for reversing side effects or overdose of a MOR agonist or opioid, obesity, and 1-DOPA induced dyskinesia in Parkinson's Disease. A nociceptin receptor (NR) antagonist may be useful for providing analgesic and antidepressant biological activity.

Other therapeutic benefits and biological activities of opioid receptors continue to be studied. Accordingly, it is important to develop new compounds that have activity with opioid receptors. While traditional chemistry techniques can be applied to creating new compounds, it is also desirable to improve chemical synthesis techniques. This can include simplifying the synthetic chemistry so that compounds can be prepared more easily.

Therefore, it would be advantageous to develop new compounds that were active with opioid receptors. Additionally, it would be beneficial to have improved synthesis techniques so that new compounds can be prepared easier and with more straight forward synthesis protocols.

BRIEF SUMMARY OF THE INVENTION

In one embodiment, the present invention includes functionalized polycyclic compounds having a structure of Formula 1 or salt, prodrug, analog, or derivative thereof, wherein Formula 1 is shown below. The structure of Formula 1 can be defined as follows: R1 and R3 are independently nothing, hydrogen, halogen, hydroxyl, straight or branched substituted or unsubstituted alkoxy, amine, straight or branched substituted or unsubstituted alkyl, substituted or unsubstituted cycloalkyl, substituted or unsubstituted aryl, branched or unbranched or cyclic substituted or unsubstituted arylalkyl, or combinations thereof; R2, R4, R5, and R6 are independently a hydrogen, halogen, hydroxyl, straight or branched substituted or unsubstituted alkoxy, amine, straight or branched substituted or unsubstituted alkyl, substituted or unsubstituted cycloalkyl, substituted or unsubstituted aryl, branched or unbranched or cyclic substituted or unsubstituted arylalkyl, or combinations thereof, or R4 and R5 together form a bond or a ring therebetween; R7 and R8 are both a hydrogen or together form a bond therebetween, or R7 and R8 together can be O (e.g., an epoxide); R9 and R10 are each independently an O or two separate hydrogen atoms; X1 and X2 independently are O, N, or S; n is from 0 to 5; when X1 is N and R1 is nothing, then R2 is a ring with the N; when X1 is O and R1 is nothing, then R2 is as defined; and when X2 is N, R3 is a something. Also, the compound can be defined as follows: wherein X1 and X2 are both N; X1 is N and X2 is O; X1 is O and X2 is N; and X1 and X1 are both O.

In one embodiment, R1-R3 can include an aryl; the aryl is substituted with one or more electron withdrawing groups. For example, the electron withdrawing groups are selected from Br, Cl, I, and $CF_3$.

In one embodiment, the compound has a structure of one of Formulas 2-16 shown below.

In one embodiment, one or more of R1, R2, R3, R4, R5, or R6 is one of chains 1-16 shown below.

In one embodiment, the compound is selected from the compounds of Tables 4, 5, 8, and 9.

In one embodiment, the present invention includes a method for preparing a functionalized polycyclic compound. Such a method can include: providing a diene; reacting the diene with a dienophile under sufficient conditions for a combined Diels-Alder/acylation reaction so as to provide a polycyclic compound having a carboxylic acid; and coupling the carboxylic acid with an amine-containing compound or a hydroxyl-containing compound so as to form an amide or an ester and producing a compound having a structure of Formula 1 (as shown and defined herein) or derivative thereof.

In one embodiment, the Diels-Alder/acylation is conducted at a temperature of at least about 165 degrees C. (+/−10-20 degrees C.) for a duration of at least about 1.5 hours (+/−15-30 minutes) when using a solvent. For neat or near neat conditions, no external heating is required, and the reaction is exothermic to provide heat, and thereby, the heat and time of a neat or near neat reaction protocol can vary, and some results have produced sufficient reactions in as little as 10 minutes.

In one embodiment, the combined Diels-Alder/acylation reaction is performed in an organic solvent. For example, the solvent can be dichloroethane or toluene. Optionally, the combined Diels-Alder/acylation reaction is at least near-neat. Also, the reaction can be performed without solvent. The reaction can be exothermic so as to provide an increase in temperature.

In one embodiment, the coupling of the carboxylic acid can be catalyzed with a catalyst. For example, the catalyst can be DMAP and/or a coupling reagent such as EDC-HCl.

The diene of the reaction can be an amine-containing diene or a hydroxyl-containing diene. The dienophile can be a maleic anhydride or citraconic anhydride or the like.

In one embodiment, the invention can include a method for preparing a functionalized polycyclic compound having a carboxylic acid. Such a method can include providing a hydroxyl-containing diene or an amine-containing diene; and reacting the diene with a dienophile under sufficient conditions for a combined Diels-Alder/acylation reaction so as to provide a polycyclic compound having a carboxylic acid having Formula 17 as shown below. In Formula 17, R3, R4, R5, and R6 can be independently a hydrogen, halogen, hydroxyl, straight or branched substituted or unsubstituted alkoxy, amine, straight or branched substituted or unsubstituted alkyl, substituted or unsubstituted cycloalkyl, substituted or unsubstituted aryl, branched or unbranched or cyclic substituted or unsubstituted arylalkyl, or combinations thereof, or R4 and R5 together form a ring therebetween; X can be an O or N; and n can be from 0 to 5. The method can also include preparing the hydroxyl-containing diene or the amine-containing diene. For example, the aminodiene component can be prepared from 3,5-hexadien-1-ol or the like.

In one embodiment, the invention can include a pharmaceutical composition having a pharmaceutically acceptable carrier, and a functionalized polycyclic compound.

In one embodiment, the invention can include a method of modulating an opioid receptor, which can be conducted by administering to an opioid receptor a functionalized polycyclic compound as described herein in an effective amount to modulate the functionality of the opioid receptor. The modulated opioid receptor can be selected from a delta, mu, kappa, or nociceptin opioid receptor. The compound can be an opioid agonist or antagonist.

In one embodiment, the invention can include a method of providing a therapy to a subject, which can be conducted by administering to the subject having an opioid receptor a functionalized polycyclic compound as described herein in a therapeutically effective amount to modulate the functionality of the opioid receptor so as to provide a biological benefit to the subject. For example, the biological benefit is one or more of the following: treatment for alcoholism; treatment for drug addiction; reversing side effects or overdose of a MOR agonist or opioid; treatment for obesity; treatment for L-DOPA-induced dyskinesia in Parkinson's Disease; providing analgesic treatment; providing antidepressant treatment; providing an anorectant treatment; providing weight loss; treatment for a mood disorder; treatment for bipolar disorders; treatment for psychotic disorders; treatment for drug seeking behavior; treatment for stress-induced drug seeking behavior; providing spinal analgesia; providing sedation; providing miosis; inhibiting ADH release; providing respiratory depression; providing euphoria; providing reduced GI motility; treatment of heart failure; treatment of migraines; treatment of a variety of inflammatory disorders; treatment of renal disorders; treatment of cardiovascular disorders; and combinations thereof.

DETAILED DESCRIPTION OF THE PREFERRED EMBODIMENTS

Generally, the present invention relates to new compounds of general Formulas 1-16 below. The compounds generically are functionalized polycyclic analogs with amide or ester functional groups, and can be included in analog libraries. The compounds can include a two-ring polycycle, wherein one homocyclic ring has 6 carbon atoms fused to a heterocyclic ring of 5-8 atoms with the hetero atoms being N or O, and where the heterocyclic ring can be saturated or include a ketone. The homocycle and heterocycle can both include functional groups. The homocycles can be cycloalkyls, cycloalkenes, cyclohexanes, cyclohexenes and the like. The heterocycles can be piperidines, 2-piperidones, lactones, tetrahydropyrans, and corresponding heterocycles having more or less atoms in the cycle. The compounds can be referred to as N-alkyl-octahydroisoquinolin-1-one-8-carboxyls and analogs thereof.

Also, the present invention includes new methods of synthesizing the compounds, such as a modified Diels-Alder/acylation reaction scheme and library production techniques. The compounds can be bioactive with regard to interacting and modulating opioid receptors, and may be agonists and/or antagonists. The new compounds can be biologically active with opioid receptors, such as being agonists with high activity or low activity or as antagonists. Some compounds can be broad spectrum agents that interact with more than one opioid receptor to provide biological activity. Other compounds can have more targeted, specific activities to a preferred opioid receptor, which can be important when selectivity and avoidance of side effects is desirable. Additionally, the compounds may be biologically active with other enzymes, receptors, or other proteins. The agonists and antagonists of opioid receptors can be used in therapeutic protocols to provide a treatment to a patient.

Additionally, the new compounds can be prepared with simpler synthetic protocols, which can make creating analog libraries a more straight forward process. The simpler synthetic protocols can include combining reaction steps so that the synthesis is easier, such as by using domino reaction synthetic schemes.

Domino reactions, in which multiple chemical reactions are carried out in a single step, are attractive tools for library synthesis because they can lead to complex structures quickly and with a minimum of chemical manipulations. The domino reactions can be used to generate scaffolds that contain reactive sites that can be used for subsequent modification and analog production, which leads to focused chemical libraries. The use of a strategy-level carbon-carbon bond forming reaction, such as the Diels-Alder cycloaddition, is attractive for library synthesis because of its well-known scope and ability to lead to cyclic materials containing multiple stereocenters. Accordingly, new synthetic reaction protocols have been developed that combine the Diels-Alder reaction with an imide acylation reaction to produce functionalized polycyclic-carboxylic acid analogs. The utility of this reaction scheme has been demonstrated by the synthesis of a small solution phase focused library of compounds, which are described herein. The carboxylic acid can then be reacted with various functional groups to provide a library.

For example, a classical Diels-Alder reaction can be modified so that a reaction of a maleic anhydride (or other dienophile) with an amine-containing diene can be performed in a single step, such as is shown in Scheme 1 below. In this reaction protocol, the Alder-endo rule can result in the amine-containing side chain emerging cis to a reactive carbonyl group. This allows for both the Diels-Alder and the acylation steps to be performed simultaneously in a tandem, one-pot synthesis of functionalized polycyclic analogs that contain a carboxylic acid, which allows for diversification in a second step. That is, the modified Diels-alder reaction can produce a scaffold having a reactive carboxylic acid group that can then be synthetically transformed to different functional groups to obtain an analog library.

It was surprising and unexpected that the modified Diels-Alder reaction could successfully produce functionalized polycyclic-carboxylic acids with a reactive group for simple conjugation chemistry. Previously, much work in this area has focused on intramolecular versions in which the diene and dienophiles are attached prior to cycloaddition, which is unfavorable in comparison to the modified Diels-Alder reaction described herein. Accordingly, it is surprising and unexpected that the chemical synthesis described herein can include the use of an extremely reactive dienophile in order to form the C—N bond without a separate alkylation event, and the availability to provide a carboxylic acid group for downstream manipulation.

Additionally, new reactions are described herein for preparing functionalized polycyclic esters and lactones.

A. Definitions

As used herein, the terms "an effective amount", "therapeutic effective amount", or "therapeutically effective amount" shall mean an amount or concentration of a compound according to the present invention which is effective within the context of its administration or use. Thus, the term "effective amount" is used throughout the specification to describe concentrations or amounts of compounds according to the present invention which may be used to produce a favorable change in the disease or condition treated, inhibited, or prevented, whether that change is a remission, a decrease in desire for a drug such as cocaine or in addiction characteristics, a favorable physiological result, or the like, depending upon the disease or condition treated.

As used herein, the term "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

As used herein, the term "coadministration" or "combination therapy" is used to describe a therapy in which at least two active compounds in effective amounts are used for the treatment, inhibition, and/or prevention of a condition.

As used herein, the term "treating" or "treatment" of a disease, including drug addiction and drug-seeking behavior, includes: (a) preventing the disease, i.e. causing the clinical symptoms of the disease not to develop in a mammal that may be exposed to or predisposed to the disease but does not yet experience or display symptoms of the disease; (b) inhibiting the disease, i.e., arresting or reducing the development of the disease or its clinical symptoms; or (c) relieving the disease, i.e., causing regression of the disease or its clinical symptoms.

As used herein, the term "unit dosage form," refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle.

As used herein, a "subject" or a "patient" refers to any animal (preferably, a human), and preferably a mammal. Examples of a subject or patient include a human, a non-human primate, a cow, a horse, a pig, a sheep, a goat, a dog, a cat or a rodent such as a mouse, a rat, a hamster, or a guinea pig. Generally, the invention is directed toward use with humans.

Chemical Structures

Generally, the compounds of the present inventions are functionalized polycyclic analogs and derivatives. Preferably, the compounds modulate the activity of an opioid receptor, such as a DOR, KOR, MOR, or NR. The compounds of the invention can generally be described by the scaffolds in Formulas 1-16 shown below.

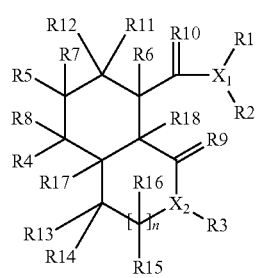

Formula 1

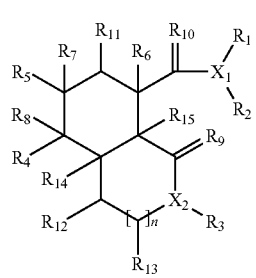

Formula 2

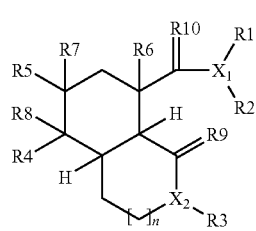

Formula 3

Formula 4 through Formula 16 (chemical structures)

In Formulas 1 through 16, R1 and R3 can be nothing, hydrogen, halogen, hydroxyl, straight or branched substituted or unsubstituted alkoxy, amine, straight or branched substituted or unsubstituted alkyl, substituted or unsubstituted cycloalkyl, substituted or unsubstituted aryl, branched or unbranched or cyclic substituted or unsubstituted arylalkyl, or combinations thereof, where the alkyls can be C1-C20, C1-C10, C1-C6, or C1-C4, where the rings can be 3, 4, 5, 6, 7, or 8 membered, and any can include chain atoms having hetero atoms selected from N, O, S, or P. R2, R4, R5, R6, R11, R12, R13, R14, R15, R16, R17, and R18 can independently be hydrogen, halogen, hydroxyl, straight or branched substituted or unsubstituted alkoxy, amine, straight or branched substituted or unsubstituted alkyl, substituted or unsubstituted cycloalkyl, substituted or unsubstituted aryl, branched or unbranched or cyclic substituted or unsubstituted arylalkyl, or combinations thereof, where the alkyls can be C1-C20, C1-C10, C1-C6, or C1-C4, where the rings can be 3, 4, 5, 6, 7, or 8 membered, and any can include chain atoms having hetero atoms selected from N, O, S, or P. R4 and R5 together, R11 and R12 together, R13 and R14 together, and R15 and R16 together can form a bond or a ring therebetween. R7 and R8 are both a hydrogen or together form a bond therebetween, or R7 and R8 together can be O (e.g., epoxide). R9 and R10 independently can be an O or two separate hydrogen atoms. X1 and X2 independently can be O or N. The "n" can be from 0 to 5, with 0, 1, and 2 preferred, with 1 most preferred. When X1 is N and R1 is nothing, then R2 is a ring with the nitrogen. When X1 is O and R1 is nothing, then R2 is as defined. When X2 is N, R3 is something, such as described for R2. The compounds can also be stereoisomers of the compounds illustrated.

In one embodiment, R14 and R15 are hydrogen. It can also be preferred that one or more of R1'-R18 are hydrogen. However, any of these R groups can be substituted as described herein.

In one embodiment, when any of R1-R3 includes an aryl, the aryl can be substituted with one or more electron withdrawing groups, such as Br, Cl, I, $CF_3$ (halogenated alkyl) or the like, especially for an R2 and/or R3.

In any of the compounds described herein, an R group alkyl or aryl backbone carbon can be substituted with O, N, S, or P, with O and N preferred. Any alkyl carbon can have a hydrogen replaced with a halogen, Cl, F, $CH_3$, $CH_3CH_2$, or higher or lower substituted or unsubstituted straight chain or branched aliphatic (e.g., C1-C10), an adamantyl (e.g., 2-adamantyl or adamantane derivative), or cycle or heterocycle. R1-R6 can independently include one or more fused or unfused cycles or heterocycles selected from phenyl, pyridine, pyrimidine, pyrazine, 1,3,5-triazine, 1,2,4-triazine, quinoline, isoquinoline, acridine, phenanthrolines, benzoquinolines, phenathridines, phenazines, quinoxalines, quinazolines, phthalazines, pteridines, cinnolines, pyrroles, imidazoles, 1,2,3-triazoles, 1,2,4, triazoles, tetrazoles, isoxazoles, 1,3-thiazoles, benzimidazoles, indoles, indazoles, benzothiazoles, phenols, naphthols, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3) oxadiazole, 5-(1,2,3) oxadiazole, 4-(1,2,3) triazole, 5-(1,2,3) triazole, or 2-(1,3,4) thiadiazole. Also, R1-R5 can independently include amino acids or polypeptides.

Any of the compounds of Formulas 1-16 can include any one of R1, R2, R3, R4, R5, or R6 being one of the following side chains (side chains 1-16):

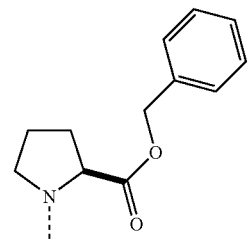

side chain 1

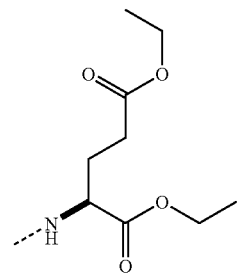

side chain 2

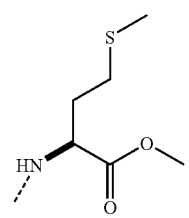

side chain 3

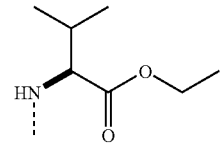

side chain 4

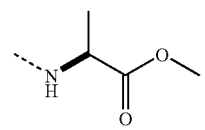

side chain 5

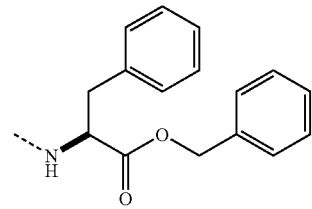

side chain 6

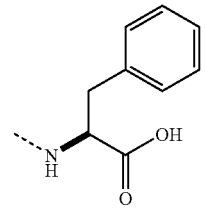

side chain 7

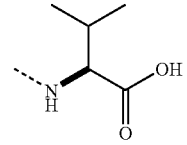

side chain 8 side chain 9
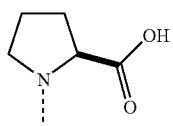

side chain 10
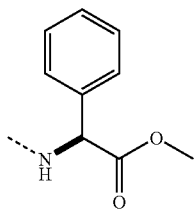

side chain 11
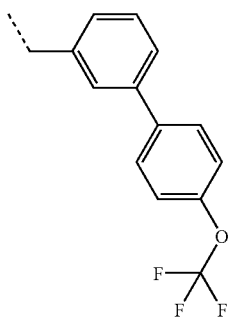

side chain 12
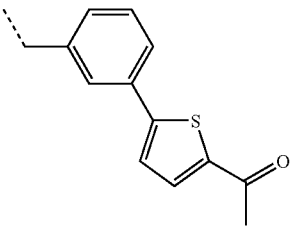

side chain 13
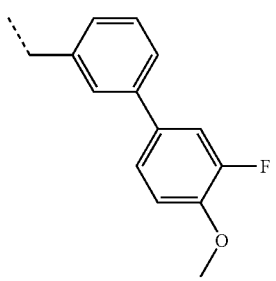

side chain 14
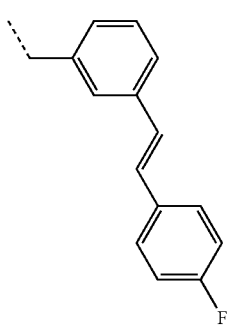

side chain 15
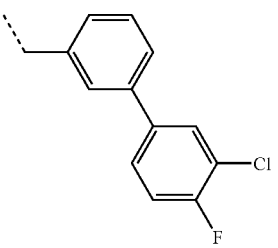

side chain 16
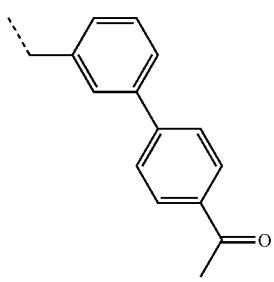

The compounds described herein can be prepared into racemic mixtures, or the individual enantiomers thereof. Each compound can also be present as an individual enantiomer that is separate from its other enantiomers. It is thought that an individual enantiomer may have enhanced biological activity over its other enantiomers.

As used herein, the term "alkyl" or "aliphatic" can refer to a hydrocarbyl moiety, such as an hydrocarbon group, that can be straight or branched, saturated or unsaturated, and/or substituted or unsubstituted, which has twenty or less carbons in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an alkyl or aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also include modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms.

Examples of heterocyclic moieties include but are not limited to morpholino, imidazole, tetrahydrofuran, and pyrrolidino.

As used herein, the term "aryl" or "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Examples of aromatic compounds that can be present include benzene, benzyl, toluene, xylene, and the like. The aromatic compound can include hetero atoms so as to be a hetero aromatic such as pyridine, furan, and the like. Also, an aromatic can be a polycyclic aromatic such as naphthalene, anthracene, phenanthrene, polycyclic aromatic hydrocarbons, indole, quinoline, isoquinoline, and the like. Any aryl herein can be a heteroaryl or polyaryl.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$, where R can be any of R1-R5. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcylohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "halo" means fluoro, chloro, bromo, or iodo, preferably fluoro and chloro.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons. The amino acids can be natural, unnatural, common, essential, non-essential or analogs or derivatives thereof.

As used herein, the term "peptide" is meant to refer to any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain. The terms "peptide," "polypeptide," and "poly(amino acid)" are used synonymously herein to refer to this class of compounds without restriction as to size. The largest members of this class are referred to as proteins.

Additionally, some of the compounds of the present invention can be prepared as racemic mixtures of isomers, mixtures of isomers, or optically isolated isomers. Compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The present invention can include racemic mixtures of the compounds defined by Formulas 1-15 and the pure individual enantiomers. All possible enantiomers under Formulas 1-15 are considered to be disclosed herein.

The compounds of this invention may possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", $4^{th}$ edition J. March, John Wiley and Sons, New York, 1992).

In some embodiments, the compounds in the compositions may be present as a pharmaceutically acceptable salt. The pharmaceutically acceptable salts includes salts of the active agent or components of the composition, prepared, for example, with acids or bases, depending on the particular substituents found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, hydrochloric acid, hydrobromic acid, sulfuric acid, nitric acid, phosphoric acid and the like, and organic acids such as trifluoroacetic, acetic, propionic, glycolic, pyruvic, oxalic, maleic, malonic, succinic, fumaric, tartaric, citric, benzoic, cinnamic, mandelic, methanesulfonic, ethanesulfonic, p-toluenesulfonic, salicylic, isobutyric, suberic, phthalic, benzenesulfonic, p-tolylsulfonic, salicylic, formic, naphthalene-2-sulfonic, and the like. Still other suitable acids include amino acids such as arginate, aspartate, glutamate, and the like.

Additionally, the compounds can be prepared to be prodrugs that include a cleavable linker between the base analog and the prodrug portion. Phosphate groups that cleave to leave hydroxyl groups are one example of prodrug moieties. Also, the ester compounds described herein can be cleaved in vivo and they themselves may be considered prodrugs. The prodrugs, such as the esters, can have shorter half lives while retaining opioid receptor activity.

As used herein, the term "analog" or the like is meant to refer to a structurally related compound or compounds with a common scaffold that different functional groups or substituents. For example, the different R groups in Formulas 1-14 can be prepared into analogs of each other by changing one or more R groups.

As used herein, the term "derivative" or the like is meant to refer to a substitution of an atom with another atom or group.

For example, when a hydrogen is replaced with a halogen or an alkyl group, such a change produces a derivative.

Pharmaceutical Compositions and Methods

Generally, the pharmaceutical compositions can be used for providing a compound in an effective amount for interacting with an opioid receptor (OR). Such a composition can include a pharmaceutically acceptable carrier containing a functionalized polycycle analog as described herein, such as an analog or derivative of the chemical structures shown herein and described in the tables. The compounds can be analogs of Formulas 1-16. It is surprising and unexpected that the compounds described herein of Formulas 1-16 can modulate opioid receptors because these compounds have substantially no similarity to other compounds, such as opiates, that modulate opioid compounds.

The compound can be present in a therapeutically effective amount for providing any function for any opioid receptor at any location. Examples include the following: providing analgesia; providing anorectic characteristics; providing weight loss; treating, inhibiting, and/or preventing depression; treating, inhibiting, and/or preventing a mood disorder; treating, inhibiting, and/or preventing bipolar disorders; treating, inhibiting, and/or preventing drug addiction; treating, inhibiting, and/or preventing drug seeking behavior; or treating, inhibiting, and/or preventing stress-induced drug seeking behavior; treating, inhibiting, and/or preventing inflammatory disorders; treating, inhibiting, and/or preventing renal disorders; treating, inhibiting; and/or preventing cardiovascular disorders; psychotic disorders. Additionally, the therapeutically effective amount can be an amount sufficient to provide a therapeutic benefit associated with agonizing or antagonizing an opioid receptor, such as the activities of Table A.

The compounds can be used for modulating opioid receptors present in human or animal tissue in vitro or in vivo. This can include administering an effective amount of a compound that is an opioid receptor agonist or antagonist to a subject such that a sufficient amount of the compound active in the brain for modulating opioid receptor activity. For example, the administration can be via subcutaneous, intravenous, inhalation, and the like.

In one embodiment, the compound can be selective for a specific opioid receptor and preferentially target a DOR, KOR, MOR or NR. The compound can be more effective at modulating one opioid receptor over another receptor. Moreover, the compound can be capable of crossing the blood brain barrier. Also, the compound may be insufficient for substantial interaction with other opioid receptors The compounds of the present invention can be formulated into a pharmaceutically acceptable formulation. Such a composition can be useful to prevent, alleviate, eliminate, inhibit or delay the onset of a disease, disorder, and/or condition related thereto. Accordingly pharmaceutical compositions can be used as a prophylactic or treatment for a disease, disorder, and/or condition.

In embodiments of the present invention, the pharmaceutical composition comprises at least one active component and inactive components. The active components are an opioid receptor modulation compound as described herein and their derivatives/analogues, salts, and prodrugs thereof. The inactive components are selected from the group consisting of excipients, carriers, solvents, diluents, stabilizers, enhancers, additives, adhesives, and combinations thereof.

The amount of the compound in a formulation can vary within the full range employed by those skilled in the art. Typically, the formulation will contain, on a weight percent basis, from about 0.01-99.99 weight percent of the compounds of the present invention based on the total formulation, with the balance being one or more suitable pharmaceutical excipients. Preferably, the compounds are present at a level of about 1-80 weight percent.

Pharmaceutical preparations include sterile aqueous or non-aqueous solutions, suspensions and emulsions. Examples of non-aqueous solvents are propylene glycol, polyethylene glycol, vegetable oil such as olive oil, injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents and inert gases and the like. Those of skill in the art can readily determine the various parameters for preparing these pharmaceutical compositions without resort to undue experimentation.

Pharmacological compositions may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

Additionally, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The pharmaceutically acceptable excipients, such as vehicles, adjuvants, carriers or diluents, are readily available to the public. Examples of suitable excipients can include, but are not limited to, the following: acidulents, such as lactic acid, hydrochloric acid, and tartaric acid; solubilizing components, such as non-ionic, cationic, and anionic surfactants; absorbents, such as bentonite, cellulose, and kaolin; alkalizing components, such as diethanolamine, potassium citrate, and sodium bicarbonate; anticaking components, such as calcium phosphate tribasic, magnesium trisilicate, and talc; antimicrobial components, such as benzoic acid, sorbic acid, benzyl alcohol, benzethonium chloride, bronopol, alkyl parabens, cetrimide, phenol, phenylmercuric acetate, thimerosol, and phenoxyethanol; antioxidants, such as ascorbic acid, alpha tocopherol, propyl gallate, and sodium metabisulfite; binders, such as acacia, alginic acid, carboxymethyl cellulose, hydroxyethyl cellulose; dextrin, gelatin, guar gum, magnesium aluminum silicate, maltodextrin, povidone, starch, vegetable oil, and zein; buffering components, such as sodium phosphate, malic acid, and potassium citrate; chelating components, such as EDTA, malic acid, and maltol; coating components, such as adjunct sugar, cetyl alcohol, polyvinyl alcohol, carnauba wax, lactose maltitol, titanium dioxide; controlled release vehicles, such as microcrystalline wax, white wax, and yellow wax; desiccants, such as calcium sulfate; detergents, such as sodium lauryl sulfate; diluents, such as calcium phosphate, sorbitol, starch, talc, lactitol, polymethacrylates, sodium chloride, and glyceryl palmitostearate; disintegrants, such as colloidal silicon dioxide, croscarmellose sodium, magnesium aluminum silicate, potassium polacrilin, and sodium starch glycolate; dispersing components, such as poloxamer 386, and polyoxyethylene fatty esters (polysorbates); emollients, such as cetearyl alcohol, lanolin, mineral oil, petrolatum, cholesterol, isopropyl myristate, and lecithin; emulsifying components, such as anionic emulsifying wax, monoethanolamine, and medium chain triglycerides; flavoring components, such as ethyl maltol, ethyl vanillin, fumaric acid, malic acid, maltol, and menthol; humectants, such as glycerin, propylene glycol, sorbitol, and triacetin; lubricants, such as calcium stearate, canola oil, glyceryl palmitostearate, magnesium oxide, poloxymer, sodium benzoate, stearic acid, and zinc stearate; solvents, such as alcohols, benzyl phenylformate, vegetable oils, diethyl phthalate, ethyl oleate, glycerol, glycofurol, for indigo carmine, polyethylene glycol, for sunset yellow, for tartazine, triacetin; stabilizing components, such as cyclodextrins, albumin, xanthan gum; and tonicity components, such as glycerol, dextrose, potassium chloride, and sodium chloride; and mixture thereof. Excipients include those that alter the rate of absorption, bioavailability, or other pharmacokinetic properties of pharmaceuticals, dietary supplements, alternative medicines, or nutraceuticals.

Other examples of suitable excipients, binders and fillers are listed in Remington's Pharmaceutical Sciences, 18th Edition, ed. Alfonso Gennaro, Mack Publishing Co. Easton, Pa., 1995 and Handbook of Pharmaceutical Excipients, 3rd Edition, ed. Arthur H. Kibbe, American Pharmaceutical Association, Washington D.C. 2000, both of which are incorporated herein by reference.

In general, pharmaceutically acceptable carriers for are well-known to those of ordinary skill in the art. This carrier can be a solid or liquid and the type is generally chosen based on the type of administration being used. Suitable pharmaceutical carriers are, in particular, fillers, such as sugars, for example lactose, sucrose, mannitol or sorbitol, cellulose preparations and/or calcium phosphates, for example tricalcium phosphate or calcium hydrogen phosphate, furthermore, binders such as starch paste, using, for example, corn, wheat, rice or potato starch, gelatin, tragacanth, methylcellulose and/or polyvinylpyrrolidone, if desired, disintegrants, such as the above mentioned starches; furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example, to identify or to indicate different doses of active ingredient, may be added to the tablets or sugar-coated tablet coatings.

Additional pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Additional formulations for use in the present invention can be found in Remington's Pharmaceutical Sciences (Mack Publishing Company, Philadelphia, Pa., 17th ed. (1985)), which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. Other examples of suitable pharmaceuticals are listed in 2000 Med Ad News 19:56-60 and The Physicians Desk Reference, 53rd edition, 792-796, Medical Economics Company (1999), both of which are incorporated herein by reference.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

According to the methods of the present invention, the compositions of the invention can be administered by injection by gradual infusion over time or by any other medically acceptable mode. Any medically acceptable method may be used to administer the composition to the patient. The particular mode selected will depend of course, upon factors such as the particular drug selected, the severity of the state of the subject being treated, or the dosage required for therapeutic efficacy. The methods of this invention, generally speaking, may be practiced using any mode of administration that is medically acceptable, meaning any mode that produces effective levels of the active composition without causing clinically unacceptable adverse effects.

The administration may be localized (i.e., to a particular region, physiological system, tissue, organ, or cell type) or systemic. For example, the composition may be administered through parental injection, implantation, orally, vaginally, rectally, buccally, pulmonary, topically, nasally, transdermally, surgical administration, or any other method of administration where access to the target by the composition is achieved. In one example, the administration is directly into the brain or brain cavity. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be used for some treatments because of the convenience to the patient as well as the dosing schedule. Compositions suitable for oral administration may be presented as discrete units such as capsules, pills, cachettes, tables, or lozenges, each containing a predetermined amount of the active compound. Other oral compositions include suspensions in aqueous or non-aqueous liquids such as a syrup, an elixir, or an emulsion.

The compounds can be encapsulated in a vehicle such as liposomes that facilitates transfer of the bioactive molecules into the targeted tissue, as described, for example, in U.S. Pat. No. 5,879,713 to Roth et al. and Woodle, et al., U.S. Pat. No. 5,013,556, the contents of which are hereby incorporated by reference. The compounds can be targeted by selecting an encapsulating medium of an appropriate size such that the medium delivers the molecules to a particular target. For example, encapsulating the compounds within microparticles, preferably biocompatible and/or biodegradable microparticles, which are appropriate sized to infiltrate, but remain trapped within, the capillary beds and alveoli of the lungs can be used for targeted delivery to these regions of the body following administration to a patient by infusion or injection.

Microparticles can be fabricated from different polymers using a variety of different methods known to those skilled in the art. The solvent evaporation technique is described, for example, in E. Mathiowitz, et al., J. Scanning Microscopy, 4, 329 (1990); L. R. Beck, et al., Fertil. Steril., 31, 545 (1979); and S. Benita, et al., J. Pharm. Sci., 73, 1721 (1984). The hot-melt microencapsulation technique is described by E. Mathiowitz, et al., Reactive Polymers, 6, 275 (1987). The spray drying technique is also well known to those of skill in the art. Spray drying involves dissolving a suitable polymer in an appropriate solvent. A known amount of the compound is suspended (insoluble drugs) or co-dissolved (soluble drugs) in the polymer solution. The solution or the dispersion is then spray-dried. Microparticles ranging between 1-10 microns are obtained with a morphology which depends on the type of polymer used:

Embodiments may also include administration of at least one pharmacological agent using a pharmacological delivery device or system such as, but not limited to, pumps (implantable or external devices), epidural injectors, syringes or other injection apparatus, catheter and/or reservoir operatively associated with a catheter, injection, and the like. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags. In one embodiment, a catheter can be used to direct the composition directly to the brain or other location in the body for systemic delivery.

The compositions of the present invention may be given in dosages, generally at the maximum amount while avoiding or minimizing any potentially detrimental side effects. The compositions can be administered in effective amounts, alone or in a cocktail with other compounds, for example, other compounds that can be used to treat, inhibit, or prevent drug addiction or drug-seeking behavior.

In one embodiment of the present invention, therapeutically effective amounts of compounds of the present invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-70 mg per day.

In another embodiment of the present invention, dosages may be estimated based on the results of experimental models, optionally in combination with the results of assays of the present invention. Generally, daily oral doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition.

Use of a long-term release implant may be particularly suitable in some cases. "Long-term release," as used herein, means that the implant is constructed and arranged to deliver therapeutic levels of the composition for at least 30 or 45 days, and preferably at least 60 or 90 days, or even longer in some cases. Long-term release implants are well known to those of ordinary skill in the art, and include some of the release systems described above.

Dosage amount and interval may be adjusted individually to provide plasma levels of the active compound which are sufficient to maintain therapeutic effect. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Synthesis

Generally, the methods for synthesizing a functionalized polycyclic analog, such as those having a carboxylic acid, amide, and/or ester can include one or more reactions in accordance with one or more of Schemes 1, 2, 3, 4, 5, 6, 7, 8, 9, 10, and/or combinations thereof. This can include synthesizing one or a plurality of functionalized polycyclic analog, such as those according to Formulas 1-15.

In one embodiment, the invention includes a method for preparing a functionalized polycyclic compound having a carboxylic acid. Such a method can include: providing a hydroxyl-containing diene or an amine-containing diene; and reacting the diene with a dienophile under sufficient conditions for a combined Diels-Alder/acylation reaction so as to provide a polycyclic compound having a carboxylic acid having Formula 17:

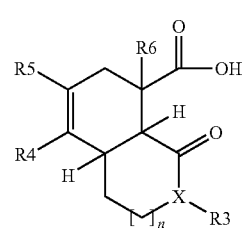

Formula 17

In Formula 17, R3, R4, R5, and R6 are independently a hydrogen, halogen, hydroxyl, straight or branched substituted or unsubstituted alkoxy, amine, straight or branched substituted or unsubstituted alkyl, substituted or unsubstituted cycloalkyl, substituted or unsubstituted aryl, branched or unbranched or cyclic substituted or unsubstituted arylalkyl, or combinations thereof, or R4 and R5 together, form a ring therebetween; X is an O, N, or S; and n is from 0 to 5. R3-R6 can be as described herein.

Additionally, the compounds herein of Formulas 1-16 can be prepared in accordance with the compound of Formula 17, and then further reacted by standard chemical synthesis to obtain any of the compounds of Formulas 1-16. While the specific protocol is described for Formula 17, the compounds can undergo further reaction to prepare the other compounds. Also, the starting reagents can be modulated in order to have the various R1-R18 groups as shown in Formula 1.

In one embodiment, the reaction can include preparing an amine-containing diene component. For example, the amine-containing diene component is prepared from 3,5-hexadien-1-ol.

In one embodiment, the reaction can include a thermal reaction of a diene with a dienophile such as a maleic anhydride. For example, when the thermal reaction provides a functionalized polycyclic carboxylic acid analog. The reaction can be in a solvent (e.g., dichloroethane or toluene) or neat. The thermal reaction conditions can include a temperature from about 25° C. to about 165° C., more preferably about 100° C. to about 165° C., and most preferably from about 150° C. to about 165° C. The thermal reaction conditions can be conducted for a duration from about 1 min to about 1.5 hours, more preferably about 30 minutes to about 1.5 hours, and most preferably from about 30 minutes to about 1 hour.

In one embodiment, a synthetic method can also include separation of individual enantiomers from a racemic mixture into compositions having a substantially pure enantiomer. The purified enantiomers can be considered to be more pure for a specific enantiomer compared to the racemic mixture.

The synthetic methods have been used to prepare heterocyclic libraries having potential biological activity. A Diels-Alder reaction was modified so that a reaction of maleic anhydride dienophile with an amine-containing diene was conducted as shown in Scheme 1. The reaction can produce an amine-containing side chain that is cis to a reactive carbonyl group. This provides a carboxylic acid group for downstream manipulation.

Scheme 1

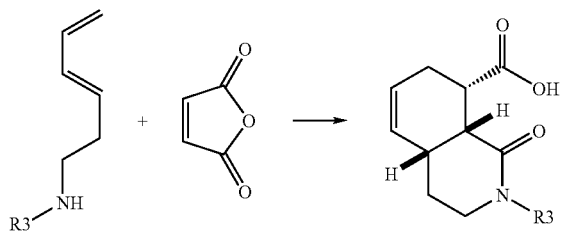

The synthesis of the amine-containing diene components can be conducted from 3,5-hexadien-1-ol, which is readily synthesized from ethyl sorbate by deconjugation and reduction. Other alkyldiene-ols can also be used to prepare the amine-containing diene. Mesylation and subsequent displacement with a primary amine readily produced the desired aminodienes in reasonable overall yields and on 1-2 g scale (Table 1). The displacement of mesylate by the amine was facilitated by microwave irradiation (acetonitrile, 130° C., 1 h); however, other methods to increase the temperature can be used. The amines were purified by silica gel chromatography prior to use in the next step. The compound number is identified by C#.

TABLE 1

Synthesis of the 1-amino-3,5-hexadienes 1{1-6}.

| entry | $R_1$ | C # | yield (%) |
|---|---|---|---|
| 1 | n-butyl | 1{1} | 87 |
| 2 | cyclopropyl | 1{2} | 40 |
| 3 | cyclohexyl | 1{3} | 78 |
| 4 | benzyl | 1{4} | 92 |
| 5 | 3,4-dichlorobenzyl | 1{5} | 97 |
| 6 | 3,4-dimethoxybenzyl | 1{6} | 80 |

The thermal reactions of diene reagents 1{1-6} and maleic anhydride were also studied through Table 2, as shown below. High internal pressures and temperatures were obtained by microwave irradiation, which facilitated the overall reaction. The diene reagents (1{1-6}) and maleic anhydride were combined in a 10 mL microwave vial in dichloroethane (DCE) and heated to 165° C. After 1.5 h, maximum yields of the functionalized polycyclic analogs 2{1-6} were obtained. A survey of reaction conditions showed that improved yields were obtained using 1.25 equivalents of the dienophile (maleic anhydride) relative to the diene 1{1-6}. While various organic solvents can be used in the process, such as $CH_2Cl_2$, toluene, and $CH_3CN$, dichloroethane obtained improved conversion in this reaction. In addition, the relatively high temperatures and ca. 1.5 h reaction times were also found to improve or provide optimal yields.

The synthetic protocol was initially conducted with six dienes being reacted with maleic anhydride to produce a series of six functionalized polycyclic scaffolds (Table 2). All of the reactions shown gave functionalized polycyclic scaffolds in good yields and, when carried out on scale, in 0.5-1.5 g quantities.

TABLE 2

Diels-Alder Reactions of Dienes 1{1-6} with Maleic Anhydride.

| entry | diene | $R_1$ | product | yield (%) |
|---|---|---|---|---|
| 1 | 1{1} | n-butyl | 2{1} | 74 |
| 2 | 1{2} | cyclopropyl | 2{2} | 76 |
| 3 | 1{3} | cyclohexyl | 2{3} | 68 |
| 4 | 1{4} | benzyl | 2{4} | 74 |
| 5 | 1{5} | 3,4-dichlorobenzyl | 2{5} | 80 |
| 6 | 1{6} | 3,4-dimethoxybenzyl | 2{6} | 80 |

The modified reaction can be conducted with other amino-containing dienes that may have a longer or shorter alkyl group as well as an alkyl group that is straight or branched substituted or unsubstituted. The maleic anhydride dienophile may also be replaced with other dienophiles.

Two additional dienophiles were shown to produce cycloaddition products. The reaction of an aminodiene 1{2} with citraconic anhydride under the above conditions produced a methyl functionalized polycyclic product 3{2} in 54% yield (Scheme 3). In addition, the reaction of an aminodiene 1{5} and citraconic anhydride at 100° C. thermal heating for 5.5 hours without solvent gave the functionalized polycyclic product 3{5} in 76% yield (Scheme 2).

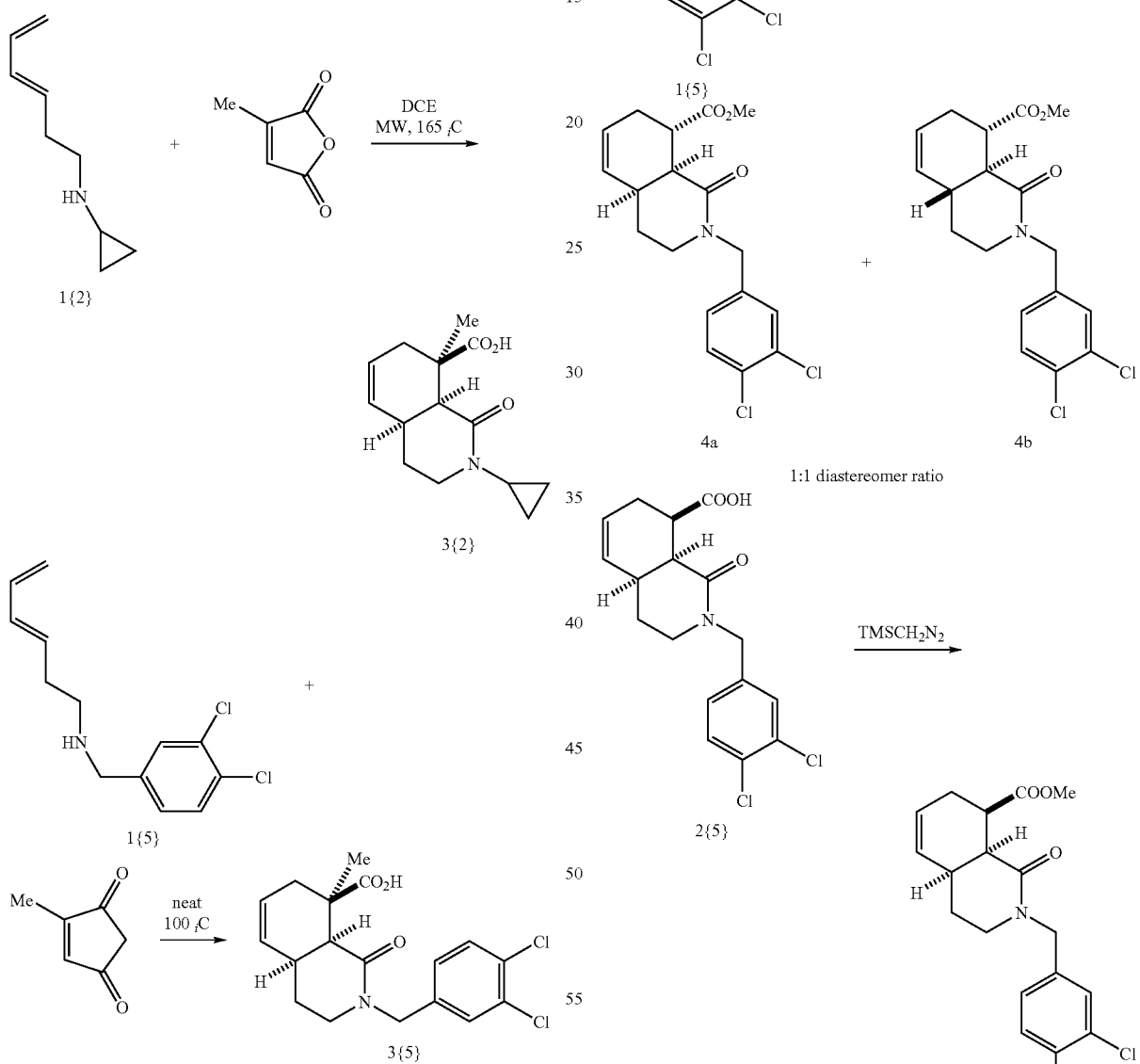

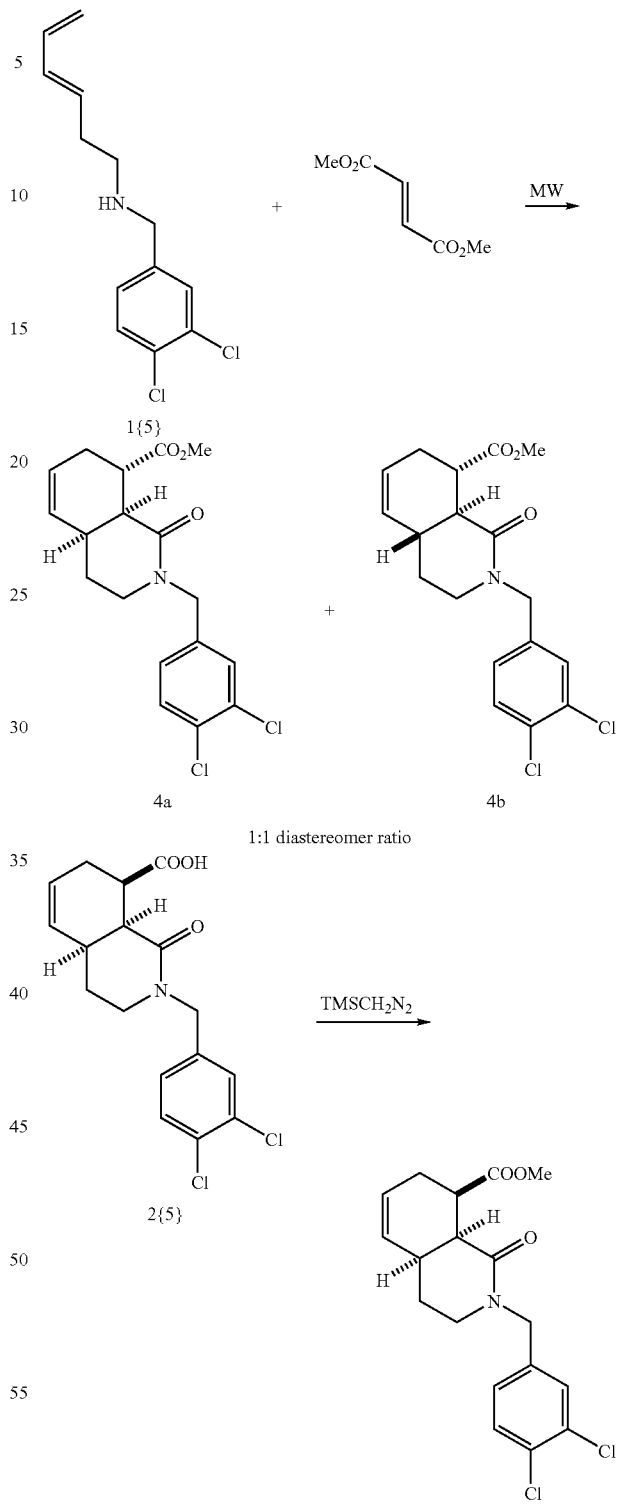

Additionally, dimethyl fumarate (it may be substituted with another dialkyl fumarate) was reacted with aminodiene 1{5} and to give compounds 4a and 4b, as an equimolar mixture of isomers, in 68-76% combined yield (Scheme 3). Treatment of adduct 2{5} with (trimethylsilyl)diazomethane smoothly produced the ester 5, which was shown to be isomerically distinct from 4a and 4b (Scheme 3), demonstrating that both Diels-Alder reactions were stereoselective.

Library Synthesis

The methods of chemical synthesis can be used to prepare a scaffold having a free carboxylic acid group that can be reacted with various amines to produce a library of analogs. For example, the amine can be any of structures 6{1} through 6{12} or related amines or other amines.

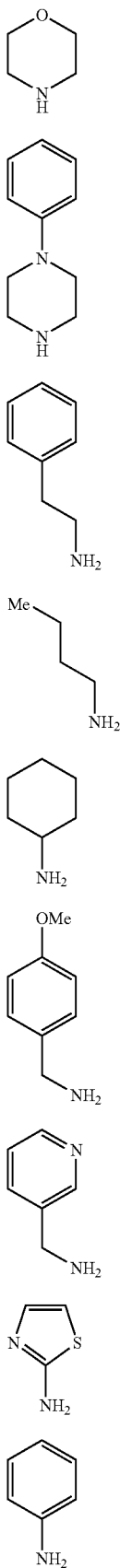

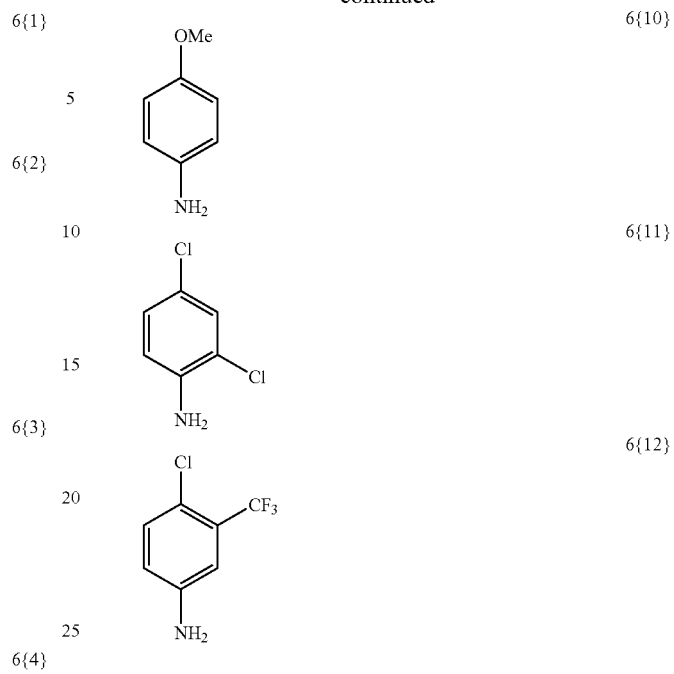

In one embodiment, the functionalizing reaction between the polycyclic carboxylic acid and an amine can be catalyzed with a catalyst. For example, the catalyst can be DMAP and/or the coupling reagent EDC-HCl).

The six scaffolds 2{1-6} prepared as described were subjected to an additional diversity step to prepare analogs. The carboxylic acids were reacted with the twelve amines 6{1-12} shown above using a catalytic amount of DMAP and N-(3'-dimethylaminopropyl)-N-ethylcarbodiimide hydrochloride (EDC.HCl) as the primary coupling reagent (Scheme 4). The amine components (6{1-12}) could be substituted with other amines to produce different analogs. The examples show productive coupling of the functionalized polycyclic analog scaffolds over a range of amines with diverse chemical reactivity. The reactions were stirred at room temperature for 14 h then partitioned between $CH_2Cl_2$ and water in phase separator tubes fitted with hydrophobic filters. The organic layers obtained were directly subjected to solid phase extraction (SPE). Elution with $CH_2Cl_2$:acetone (1:1) provided the crude amide coupled products. The compounds thus prepared were subjected to mass-directed HPLC purification to produce the adducts shown (Table 3). The compounds can be identified by combining the functionalized polycyclic analog scaffold and the amine groups to form an amide.

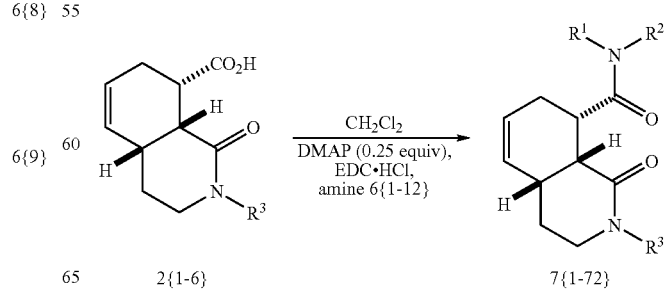

TABLE 3

Parallel synthesis of a 72-member functionalized polycyclic amide library.

| product | scaffold | amine | crude purity (%) | purified yield | final purity (%) | HRMS, calcd for [M + H]+ | HRMS, found |
|---|---|---|---|---|---|---|---|
| 7{1} | 2{1} | 6{1} | 97 | 26 mg (82%) | 100 | 321.2178 | 321.2186 |
| 7{2} | 2{1} | 6{2} | 88 | 35 mg (88%) | 100 | 396.2651 | 396.2655 |
| 7{3} | 2{1} | 6{3} | 86 | 31 mg (88%) | 91 | 355.2386 | 355.2395 |
| 7{4} | 2{1} | 6{4} | 91 | 21 mg (68%) | 100 | 307.2386 | 307.2399 |
| 7{5} | 2{1} | 6{5} | 93 | 21 mg (62%) | 100 | 333.2542 | 333.2568 |
| 7{6} | 2{1} | 6{6} | 84 | 31 mg (85%) | 100 | 371.2335 | 371.2359 |
| 7{7} | 2{1} | 6{7} | 93 | 11 mg (31%) | 100 | 342.2182 | 342.2205 |
| 7{8} | 2{1} | 6{8} | 91 | 28 mg (84%) | 98 | 334.1589 | 334.1610 |
| 7{9} | 2{1} | 6{9} | 84 | 25 mg (78%) | 100 | 327.2073 | 327.2091 |
| 7{10} | 2{1} | 6{10} | 81 | 31 mg (87%) | 100 | 357.2178 | 357.2211 |
| 7{11} | 2{1} | 6{11} | 60 | 29 mg (73%) | 100 | 395.1293 | 395.1315 |
| 7{12} | 2{1} | 6{12} | 71 | 32 mg (75%) | 99 | 429.1557 | 429.1585 |
| 7{13} | 2{2} | 6{1} | 80 | 18 mg (60%)[a] | 87[a] | 305.1865 | 305.1884 |
| 7{14} | 2{2} | 6{2} | 79 | 26 mg (69%) | 91 | 380.2338 | 380.2351 |
| 7{15} | 2{2} | 6{3} | 84 | 17 mg (50%) | 97 | 339.2073 | 339.2079 |
| 7{16} | 2{2} | 6{4} | 89 | 20 mg (67%) | 100 | 291.2073 | 291.2088 |
| 7{17} | 2{2} | 6{5} | 10 | 1 mg (6%) | 100 | 317.2229 | 317.2252 |
| 7{18} | 2{2} | 6{6} | 97 | 22 mg (61%) | 97 | 355.2022 | 355.2034 |
| 7{19} | 2{2} | 6{7} | 84 | 2 mg (7%) | 100 | 326.1869 | 326.1887 |
| 7{20} | 2{2} | 6{8} | 54 | 18 mg (57%) | 99 | 318.1276 | 318.1291 |
| 7{21} | 2{2} | 6{9} | 85 | 13 mg (42%) | 100 | 311.1760 | 311.1784 |
| 7{22} | 2{2} | 6{10} | 74 | 19 mg (56%) | 100 | 341.1865 | 341.1890 |
| 7{23} | 2{2} | 6{11} | 50 | 21 mg (56%) | 99 | 379.0980 | 379.0995 |
| 7{24} | 2{2} | 6{12} | 57 | 29 mg (70%) | 100 | 413.1244 | 413.1268 |
| 7{25} | 2{3} | 6{1} | 95 | 18 mg (53%) | 100 | 347.2335 | 347.2345 |
| 7{26} | 2{3} | 6{2} | 89 | 28 mg (65%) | 99 | 422.2808 | 422.2815 |
| 7{27} | 2{3} | 6{3} | 88 | 24 mg (63%) | 99 | 381.2542 | 381.2547 |
| 7{28} | 2{3} | 6{4} | 91 | 14 mg (42%) | 100 | 333.2542 | 333.2550 |
| 7{29} | 2{3} | 6{5} | 85 | 30 mg (83%) | 96 | 359.2699 | 359.2714 |
| 7{30} | 2{3} | 6{6} | 65 | 36 mg (90%) | 98 | 397.2491 | 397.2509 |
| 7{31} | 2{3} | 6{7} | 99 | 18 mg (50%) | 95 | 368.2338 | 368.2372 |
| 7{32} | 2{3} | 6{8} | 77 | 20 mg (56%) | 95 | 360.1746 | 360.1762 |
| 7{33} | 2{3} | 6{9} | 86 | 24 mg (69%) | 98 | 353.2229 | 353.2241 |
| 7{34} | 2{3} | 6{10} | 65 | 30 mg (78%) | 98 | 383.2335 | 383.2347 |
| 7{35} | 2{3} | 6{11} | 49 | 22 mg (51%) | 100 | 421.1450 | 421.1469 |
| 7{36} | 2{3} | 6{12} | 69 | 32 mg (69%) | 99 | 455.1713 | 455.1721 |

TABLE 3-continued

Parallel synthesis of a 72-member functionalized polycyclic amide library.

| product | scaffold | amine | crude purity (%) | purified yield | final purity (%) | HRMS, calcd for [M + H]+ | HRMS, found |
|---|---|---|---|---|---|---|---|
| 7{37} | 2{4} | 6{1} | 89 | 21 mg (59%) | 100 | 355.2022 | 355.2035 |
| 7{38} | 2{4} | 6{2} | 87 | 31 mg (72%) | 97 | 430.2495 | 430.2491 |
| 7{39} | 2{4} | 6{3} | 88 | 29 mg (75%) | 96 | 389.2229 | 389.2237 |
| 7{40} | 2{4} | 6{4} | 82 | 14 mg (42%) | 98 | 341.2229 | 341.2236 |
| 7{41} | 2{4} | 6{5} | 65 | 30 mg (81%) | 100 | 367.2386 | 367.2401 |
| 7{42} | 2{4} | 6{6} | 76 | 39 mg (96%) | 99 | 405.2178 | 405.2204 |
| 7{43} | 2{4} | 6{7} | 99 | 20 mg (54%) | 97 | 376.2025 | 376.2053 |
| 7{44} | 2{4} | 6{8} | 97 | 32 mg (90%) | 99 | 368.1433 | 368.1456 |
| 7{45} | 2{4} | 6{9} | 91 | 34 mg (93%) | 100 | 361.1916 | 361.1924 |
| 7{46} | 2{4} | 6{10} | 87 | 35 mg (85%) | 100 | 391.2022 | 391.2031 |
| 7{47} | 2{4} | 6{11} | 28 | 11 mg (26%) | 100 | 429.1137 | 429.1150 |
| 7{48} | 2{4} | 6{12} | 72 | 45 mg (99%) | 100 | 463.1400 | 463.1426 |
| 7{49} | 2{5} | 6{1} | 98 | 21 mg (48%) | 100 | 423.1242 | 423.1257 |
| 7{50} | 2{5} | 6{2} | 84 | 29 mg (58%) | 99 | 498.1715 | 498.1718 |
| 7{51} | 2{5} | 6{3} | 82 | 23 mg (49%) | 99 | 457.1450 | 457.1463 |
| 7{52} | 2{5} | 6{4} | 90 | 22 mg (54%) | 100 | 409.1450 | 409.1454 |
| 7{53} | 2{5} | 6{5} | 98 | 24 mg (55%) | 100 | 435.1606 | 435.1616 |
| 7{54} | 2{5} | 6{6} | 79 | 44 mg (92%) | 100 | 473.1399 | 473.1407 |
| 7{55} | 2{5} | 6{7} | 98 | 27 mg (61%) | 99 | 444.1246 | 444.1255 |
| 7{56} | 2{5} | 6{8} | 90 | 11 mg (24%) | 100 | 436.0653 | 436.0671 |
| 7{57} | 2{5} | 6{9} | 91 | 33 mg (77%) | 100 | 429.1137 | 429.1152 |
| 7{58} | 2{5} | 6{10} | 84 | 35 mg (75%) | 100 | 459.1242 | 459.1247 |
| 7{59} | 2{5} | 6{11} | 32 | 2 mg (5%) | 98 | 497.0357 | 497.0356 |
| 7{60} | 2{5} | 6{12} | 77 | 44 mg (82%) | 100 | 531.0621 | 531.0616 |
| 7{61} | 2{6} | 6{1} | 85 | 20 mg (48%) | 100 | 415.2233 | 415.2246 |
| 7{62} | 2{6} | 6{2} | 66 | 33 mg (67%) | 83 | 490.2706 | 490.2709 |
| 7{63} | 2{6} | 6{3} | 74 | 23 mg (51%) | 100 | 449.2440 | 449.2453 |
| 7{64} | 2{6} | 6{4} | 76 | 13 mg (34%) | 100 | 401.2440 | 401.2445 |
| 7{65} | 2{6} | 6{5} | 86 | 13 mg (31%) | 100 | 427.2597 | 427.2602 |
| 7{66} | 2{6} | 6{6} | 66 | 23 mg (49%) | 99 | 465.2389 | 465.2394 |
| 7{67} | 2{6} | 6{7} | 92 | 12 mg (28%) | 99 | 436.2236 | 436.2261 |
| 7{68} | 2{6} | 6{8} | 69 | 16 mg (37%) | 97 | 428.1644 | 428.1667 |
| 7{69} | 2{6} | 6{9} | 75 | 16 mg (39%) | 100 | 421.2127 | 421.2134 |
| 7{70} | 2{6} | 6{10} | 70 | 27 mg (64%) | 100 | 451.2233 | 451.2248 |

TABLE 3-continued

Parallel synthesis of a 72-member functionalized polycyclic amide library.

| product | scaffold | amine | crude purity (%) | purified yield | final purity (%) | HRMS, calcd for [M + H]+ | HRMS, found |
|---|---|---|---|---|---|---|---|
| 7{71} | 2{6} | 6{11} | 40 | 19 mg (39%) | 97 | 489.1348 | 489.1344 |
| 7{72} | 2{6} | 6{12} | 58 | 32 mg (61%) | 99 | 523.1611 | 523.1611 |

[a]Insoluble sample, purified by flash chromatography

All chemicals were used as purchased from commercial suppliers. Methylene chloride and THF were dried by being passed through two packed columns of neutral alumina using the PurSolv solvent purification system (Innovative Technology Inc.) prior to use. (E)-3,5-hexadien-1-ol was prepared following the protocol of Miller and Batey (Miller, C. A.; Batey, R. A. Org. Lett. 2004, 6, 699-702). (E)-3,5-hexadien-1-yl methanesulfonate and N-benzyl-N-[(E)-3,5-hexadien-1-yl]amine 1{4} were prepared following the protocol of Metz and coworkers (Plietker, B.; Seng, D.; Fröhlich, R; Metz, P. Tetrahedron 2000, 56, 873-879). The chromatography solvent "wet ether" refers to the organic layer of a 9:1:0.1 ether:aqueous potassium phosphate, monobasic (0.5 M):glacial acetic acid mixture (Taber, D. F.; Pan, Y.; Zhao, X. J. Org. Chem. 2004, 69, 7234-7240).

The parallel syntheses were performed on the Bohdan Miniblock XT parallel solution phase synthesizer obtained from Mettler-Toledo Auto Chem. Automated weighing was performed using the Bohdan Balance Automator (Mettler-Toledo Auto Chem). Parallel evaporation was performed on the GeneVac EZ-2 plus evaporator system. $^1$H and $^{13}$C NMR spectra were recorded on a Bruker AM 400 spectrometer (operating at 400 and 100 MHz respectively) in CDCl$_3$ with 0.03% TMS as an internal standard. Chemical shifts are reported in parts per million (ppm) downfield from TMS. $^{13}$C multiplicities were determined with the aid of an APT pulse sequence, differentiating the signals for methyl and methane carbons as "d" from methylene and quarternary carbons as "u". The infrared (IR) spectra were acquired as thin on a PerkinElmer Spectrum One FT-1R spectrometer and the absorption frequencies are reported in cm$^{-1}$. Melting points were determined on an Electrothermal Mel-Temp model number 101D apparatus and are uncorrected.

HPLC analysis was carried out using a Xterra MS C-18 column (5 μM, 4.6×150 mm) with gradient elution (10% CH$_3$CN to 100% CH$_3$CN) on a Waters mass-directed fractionation instrument using a Waters 2767 sample manager, a Waters 2525 HPLC pump, a 2487 dual λ absorbance detector and a Waters/MicroMass ZQ (quadrupole) MS connected to a PC with a MassLynx workstation. Purification was carried out using an Xterra MS C-18 column (5 μM, 19×150 mm) with narrow gradient elution (acetonitrile and water) with a UV fraction trigger. High resolution mass spectra (HRMS) [ESI+] were obtained using a Waters/MicroMass ICT Premier (TOF instrument).

General Procedures for Preparing Aminodienes

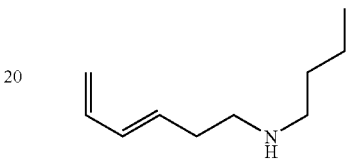

N-Butyl-N-[(E)-3,5-hexadien-1-yl]amine 1{1}. (E)-3,5-hexadien-1-yl methanesulfonate (726.8 mg, 4.54 mmol) and n-butylamine (4.5 mL, 40.54 mmol) were stirred in a sealed tube for 19 h at 65° C. The reaction was partitioned between NaOH (1 N, 30 mL) and ether. The organics were dried (Na$_2$SO$_4$), the solvent removed in vacuo and the residue purified by silica chromatography to give 1{1} as a pale yellow oil (552.0 mg, 3.60 mmol, 79% yield). TLC R$_f$=0.25 (CH$_2$Cl$_2$/acetone 1:1); $^1$H NMR δ 0.92 (t, J=7.3 Hz, 3 H), 1.34 (m, 2 H), 1.47 (m, 2 H), 2.30 (m, 2 H), 2.60 (t, J=7.0 Hz, 2 H), 2.68 (t, J=7.6 Hz, 2 H), 4.98 (d, J=10.0 Hz, 1 H), 5.11 (d, J=16.9 Hz, 1 H), 5.68 (m, 1 H), 6.09-6.15 (m, 1 H), 6.27-6.36 (m, 1 H); $^{13}$C NMR δ d 14.0, 132.6 (×2), 137.0; u 20.5, 32.3, 33.2, 49.2, 49.7, 115.4; IR 3253 (w), 3086 (m), 2958 (s), 2928 (s), 1652 (m) cm$^{-1}$; HRMS calcd for C$_{10}$H$_{20}$N 153.1596, obsd 154.1571.

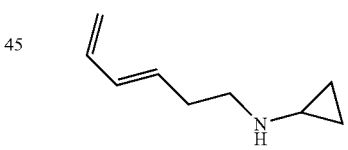

N-Cyclopropyl-N-[(E)-3,5-hexadien-1-yl]amine 1{2}. (E)-3,5-hexadien-1-yl methanesulfonate (515.7 mg, 3.22 mmol) and cyclopropylamine (2.2 mL, 32.18 mmol) were stirred in a sealed tube for 19 h at 65° C. The reaction was partitioned between NaOH (1 N, 30 mL) and ether. The organics were dried (Na$_2$SO$_4$), the solvent removed in vacuo and the residue purified by silica chromatography to give 1{2} as a pale yellow oil (175.4 mg, 1.28 mmol, 40% yield). TLC R$_f$=0.40 (CH$_2$Cl$_2$/acetone 1:1); $^1$H NMR δ 0.29-0.33 (m, 2 H), 0.39-0.43 (m, 2 H), 2.07-2.12 (m, 1 H), 2.24-2.30 (m, 2 H), 2.75 (t, J=6.9 Hz, 2 H), 4.97 (d, J=10.0 Hz, 1 H), 5.09 (d, J=16.9 Hz, 1 H), 5.62-5.69 (m, 1 H), 6.07-6.13 (m, 1 H), 6.25-6.34 (m, 1 H); $^{13}$C NMR δ d 30.2, 132.7, 132.7 (×2); u 6.4 (×2), 33.2, 48.9, 115.5; IR 3087 (m), 3008 (s), 2931 (s), 1652 (m), 1603 (m) cm$^{-1}$; HRMS calcd for C$_{10}$H$_{20}$N 138.1283, obsd 138.1244.

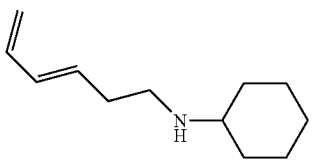

N-Cyclohexyl-N-[(E)-3,5-hexadien-1-yl]amine 1{3}. (E)-3,5-hexadien-1-yl methanesulfonate (801.0 mg, 5.00 mmol) and cyclohexylamine (5.7 mL, 50.00 mmol) were stirred in a sealed tube for 19 h at 65° C. The reaction was partitioned between NaOH (1 N, 30 mL) and ether. The organics were dried ($Na_2SO_4$), the solvent removed in vacuo and the residue purified by silica chromatography to give 1{3} as a pale yellow oil (734.5 mg, 4.10 mmol, 82% yield). TLC $R_f$=0.15 ($CH_2Cl_2$/acetone 1:1); $^1$H NMR δ 1.00-1.26 (m, 6 H), 1.58-1.88 (m, 4 H), 2.24-2.30 (m, 2 H), 2.38-2.43 (m, 1 H), 2.69 (t, J=7.0 Hz, 2 H), 4.97 (d, J=10.0 Hz, 1 H), 5.11 (d, J=16.4 Hz, 1 H), 5.62-5.71 (m, 1 H), 6.07-6.15 (m, 1 H), 6.25-6.36 (m, 1 H); $^{13}$C NMR δ d 56.9, 132.7, 132.8, 137.2; u 25.2 (×2), 26.3, 33.6, 33.8 (×2), 46.3, 115.5; IR 3085 (w), 2927 (s), 2853 (s), 1652 (m) $cm^{-1}$; HRMS calcd for $C_{12}H_{22}N$ 180.1752, 180.1741 obsd.

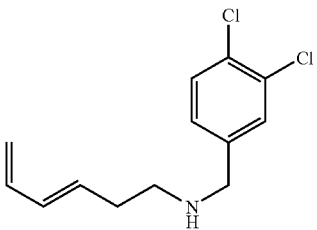 [SMILES: C=C/C=C/CCNCc1ccc(Cl)c(Cl)c1]

N-(3,4-Dichlorobenzyl)-N-[(E)-3,5-hexadien-1-yl]amine 1{5}. (E)-3,5-hexadien-1-yl methanesulfonate (310.5 mg, 1.94 mmol) and 3,4-dichlorobenzylamine (1,023.4 mg, 5.81 mmol) and MeCN (1 mL) were stirred in a sealed tube for 1 h at 130° C. under microwave irradiation. The reaction was partitioned between NaOH (1 N, 30 mL) and ether. The organics were dried ($Na_2SO_4$), the solvent removed in vacuo and the residue purified by silica chromatography to give 1(5) as a colorless oil (303.3 mg, 1.18 mmol, 61% yield). TLC $R_f$=0.85 ($CH_2Cl_2$/acetone 1:1); $^1$H NMR δ 2.30 (m, 2 H), 2.68 (t, J=6.5 Hz, 2 H), 3.74 (s, 2 H), 5.00 (d, J=8.6 Hz, 1 H), 5.12 (d, J=18.4 Hz, 1 H), 5.63-5.70 (m, 1 H), 6.08-6.15 (m, 1 H), 6.26-6.36 (m, 1 H), 7.15 (dd, J=8.1, 2.0 Hz, 1 H), 7.38 (d, J=8.2 Hz, 1 H), 7.43 (d, J=1.7 Hz, 1 H); $^{13}$C NMR δ d 127.4, 130.0, 130.3, 132.2, 132.9, 136.9; u 33.1, 48.5, 52.7, 115.7, 130.7, 132.4, 140.8; IR 3313 (w), 2914 (s), 2826 (s), 1806 (w), 1651 (m) $cm^{-1}$; HRMS calcd for $C_{13}K_{16}Cl_2N$ 256.0660, 256.0655 obsd.

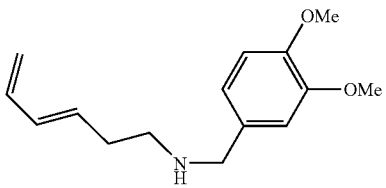 [SMILES: C=C/C=C/CCNCc1ccc(OC)c(OC)c1]

N-(3,4-Dimethoxybenzyl)-N-[(E)-3,5-hexadien-1-yl]amine 1{6}. (E)-3,5-hexadien-1-yl methanesulfonate (688.0 mg, 4.29 mmol) and 3,4-dichlorobenzylamine (2,513.0 mg, 15.03 mmol) and MeCN (2 mL) were stirred in a sealed tube for 1 h at 130° C. under microwave irradiation. The reaction was partitioned between NaOH (1 N, 30 mL) and ether. The organics were dried ($Na_2SO_4$), the solvent removed in vacuo and the residue purified by silica chromatography to give 1{6} as a light yellow oil (686.1 mg, 2.77 mmol, 65% yield). TLC $R_f$=0.34 ($CH_2Cl_2$/acetone 1:1); $^1$H NMR δ 2.32 (m, 2 H), 2.72 (t, J=7.1 Hz, 2 H), 3.75 (s, 2 H), 3.88 (s, 3 H), 3.90 (s, 3 H), 5.00 (d, J=10.1 Hz, 1 H), 5.12 (d, J=17.0 Hz, 1 H), 5.65-5.73 (m, 1 H), 6.09-6.16 (m, 1 H), 6.27-6.36 (m, 1 H), 6.81-6.86 (m, 2 H), 6.89 (d, J=1.44 Hz, 1 H); $^{13}$C NMR δ d 56.0, 56.1, 111.1, 111.5, 120.3, 132.7, 132.8, 137.1; u 33.2, 48.7, 53.8, 115.6, 133.2, 148.1, 149.1; IR 3318 (w), 3000 (s), 2934 (s), 2833 (s), 1801 (w), 1651 (m) $cm^{-1}$; HRMS calcd for $C_{15}H_{22}NO_2$ 248.1651, 248.1655 obsd.

General Procedures for the Tandem Diels-Alder/Acylation Reaction Sequence

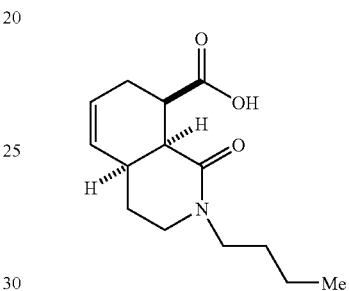

2-Butyl-1-oxo-1,2,3,4,4a,7,8,8a-octahydroisoquinoline-8-carboxylic acid 2{1}. Amino diene 1{1} (192.2 mg, 1.25 mmol) and maleic anhydride (153.0 mg, 1.56 mmol) were dissolved in dichloroethane (3 mL) and heated at 165° C. for 1.5 h under microwave irradiation. The solvent was removed in vacuo and the residue chromatographed to give 2{1} as a colorless oil (232.0 mg, 0.92 mmol, 74% yield). The product precipitated as a tan solid upon trituration with hexanes. TLC $R_f$=0.45 ("wet ether"); mp=96.5-101.5° C.; $^1$H NMR δ 0.93 (t, J=7.4 Hz, 3 H), 1.29 (q, J=7.6 Hz, 2 H), 1.48-1.53 (m, 2 H), 1.90-2.04 (m, 2 H), 2.28-2.46 (m, 2 H), 2.82 (s, 1 H), 2.89-2.90 (m, 1 H), 3.11-3.33 (m, 4 H), 3.49-3.57 (m, 1 H), 5.57 (d, J=10.0 Hz, 1 H), 5.88-5.93 (m, 1 H); $^{13}$C NMR δ d 13.8, 34.6, 41.3, 44.7, 127.5, 129.3; u 19.9, 25.2, 27.0, 28.8, 44.4, 47.7, 171.1, 176.6; IR 2933 (m), 2253 (m), 1709 (s), 1625 (m) cm'; HRMS calcd for $C_{14}H_{22}NO_3$ 252.1600, 252.1606 obsd.

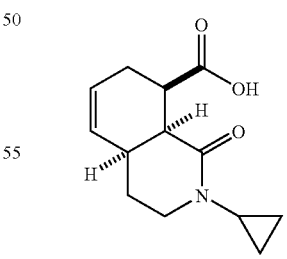

2-cyclopropyl-1-oxo-1,2,3,4,4a,7,8,8a-octahydroiso-quinoline-8-carboxylic acid 2{2}. Amino diene 1{2} (165.0 mg, 1.20 mmol) and maleic anhydride (147.5 mg, 1.50 mmol) were dissolved in dichloroethane (3 mL) and heated at 165° C. for 1.5 h under microwave irradiation. The solvent was removed in vacuo and the residue chromatographed to give 2{2} as an off-white solid (215.9 mg, 0.92 mmol, 76% yield).

TLC R$_f$=0.35 ("wet ether"); mp=147-149° C.; $^1$H NMR δ 0.48-0.54 (m, 1 H), 0.68-0.88 (m, 3 H), 1.84-1.98 (m, 2 H), 2.26-2.41 (m, 2 H), 2.64-2.70 (m, 1 H), 2.79-2.85 (m, 2 H), 3.14-3.21 (m, 3 H), 5.54 (d, J=8.6 Hz, 1 H), 5.85-5.86 (m, 1 H); $^{13}$C NMR δ d 30.3, 34.3, 42.2, 43.6, 127.5, 129.4; u 6.4, 6.9, 24.6, 27.3, 44.4, 173.3, 177.6; IR 3053 (s), 2886 (s), 1708 (s), 1639 (m) cm$^{-1}$; HRMS calcd for C$_{13}$H$_{18}$NO$_3$ 236.1287, 236.1293 obsd.

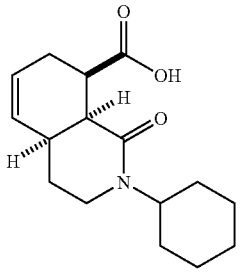 [SMILES: O=C(O)[C@@H]1CC=C[C@@H]2CCN(C3CCCCC3)C(=O)[C@@H]21]

2-cyclohexyl-1-oxo-1,2,3,4,4a,7,8,8a-octahydroisoquinoline-8-carboxylic acid 2{3}. Amino diene 1{3} (399.0 mg, 2.23 mmol) and maleic anhydride (272.8 mg, 2.78 mmol) were dissolved in dichloroethane (4 mL) and heated at 165° C. for 1.5 h under microwave irradiation. The solvent was removed in vacuo and the residue chromatographed to give 2{3} as a very light yellow solid (423.6 mg, 1.53 mmol, 68% yield). TLC R$_f$=0.56 ("wet ether"); mp=164.5-168.0° C.; $^1$H NMR δ 1.36-1.46 (m, 4 H), 1.58-1.71 (m, 4 H), 1.80-1.84 (m, 2 H), 1.90-1.95 (m, 2 H), 2.28-2.47 (m, 2 H), 2.78-2.82 (m, 1 H), 2.90-2.95 (m, 1 H), 3.05-3.14 (m, 2 H), 3.21-3.25 (m, 1 H), 4.39-4.46 (m, 1 H), 5.54 (d, J=10.1 Hz, 1 H), 5.88-5.91 (m, 1 H); $^{13}$C NMR δ d 33.9, 41.8, 44.4, 53.6, 127.4, 129.2; u 24.9, 25.4, 25.5, 25.6, 27.0, 29.3, 29.5, 38.3, 170.6, 177.5; IR 2930 (s), 2858 (s), 1708 (s), 1619 (s) cm$^{-1}$; HRMS calcd for C$_{16}$H$_{24}$NO$_3$ 278.1756, 278.1785 obsd.

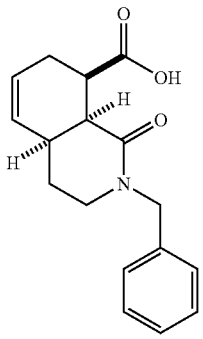 [SMILES: O=C(O)[C@@H]1CC=C[C@@H]2CCN(Cc3ccccc3)C(=O)[C@@H]21]

2-benzyl-1-oxo-1,2,3,4,4a,7,8,8a-octahydroisoquinoline-8-carboxylic acid 2{4}. Amino diene 1{4} (187.3 mg, 1.00 mmol) and maleic anhydride (122.6 mg, 1.25 mmol) were dissolved in dichloroethane (2.5 mL) and heated at 165° C. for 1.5 h under microwave irradiation. The solvent was removed in vacuo and the residue chromatographed to give 2{4} as a very light yellow solid (210.9 mg, 0.74 mmol, 74% yield). TLC R$_f$=0.56 ("wet ether"); mp=149.0-152.0° C.; $^1$H NMR δ 1.86-1.92 (m, 1 H), 1.95-2.04 (m, 1 H), 2.37-2.51 (m, 2 H), 2.82-2.85 (m, 1 H), 2.88-2.97 (m, 1 H), 3.15-3.19 (m, 2 H), 3.23-3.24 (m, 1 H), 4.53 (d, J=14.6 Hz, 1 H), 4.72 (d, J=14.9 Hz, 1 H), 5.55 (dd, J=1.8, 10.0 Hz, 1 H), 5.88-5.93 (m, 1 H), 7.20 (d, J=7.9 Hz, 2 H), 7.30-7.36 (m, 3 H); $^{13}$C NMR δ d 34.8, 41.3, 45.4, 127.5, 127.7, 127.8, 128.7, 129.5; u 25.6, 27.0, 44.0, 51.0, 135.9, 172.0, 175.6; IR 3026 (s), 2923 (s), 1704 (s), 1635 (s) cm$^{-1}$; HRMS calcd for C$_{17}$H$_{20}$NO$_3$ 286.1443, 286.1452 obsd.

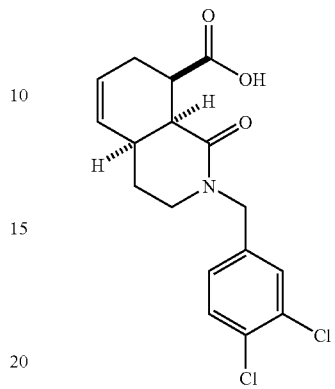

2-(3,4-dichlorobenzyl)-1-oxo-1,2,3,4,4a,7,8,8a-octahydroisoquinoline-8-carboxylic acid 2{5}. Amino diene 1{5} (256.2 mg, 1.00 mmol) and maleic anhydride (122.6 mg, 1.25 mmol) were dissolved in dichloroethane (2.5 mL) and heated at 165° C. for 1.5 h under microwave irradiation. The solvent was removed in vacuo and the residue chromatographed to give 2{5} as a very light yellow solid (283.4 mg, 0.80 mmol, 80% yield). TLC R$_f$=0.63 ("wet ether"); mp=208.0-209.5° C.; $^1$H NMR δ 1.89-1.95 (m, 1 H), 2.00-2.09 (m, 1 H), 2.35-2.51 (m, 2 H), 2.86-2.91 (m, 2 H), 3.12-3.22 (m, 2 H), 3.29-3.31 (m, 1 H), 4.31 (d, J=15.0 Hz, 1 H), 4.79 (d, J=15.0 Hz, 1 H), 5.58 (d, J=10.0 Hz, 1 H), 5.91-5.95 (m, 1 H), 7.05 (dd, J=1.7, 8.2 Hz, 1 H), 7.26 (d, J=2.1 Hz, 1 H), 7.40 (d, J=8.2 Hz, 1 H); $^{13}$C NMR δ d 34.7, 41.6, 44.5, 127.1, 127.6, 129.5, 129.7, 130.7; u 25.2, 27.0, 44.4, 50.6, 131.8, 132.8, 136.4, 171.9, 175.7; IR 3434 (s), 2107 (m), 1699 (s), 1626 (s) cm$^{-1}$; HRMS calcd for C$_{17}$H$_{18}$NO$_3$ 354.0664, 354.0667 obsd.

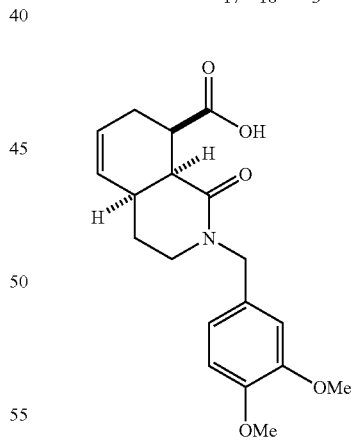

2-(3,4-dimethoxybenzyl)-1-oxo-1,2,3,4,4a,7,8,8a-octahydroisoquinoline-8-carboxylic acid 2{6}. Amino diene 1{6} (348.8 mg, 1.41 mmol) and maleic anhydride (172.9 mg, 1.76 mmol) were dissolved in dichloroethane (3.5 mL) and heated at 165° C. for 1.5 h under microwave irradiation. The solvent was removed in vacuo and the residue chromatographed to give 2{6} as a fluffy white solid (387.2 mg, 1.12 mmol, 80% yield). TLC R$_f$=0.23 ("wet ether"); mp=142.5-144.0° C.; $^1$H NMR δ 1.86-1.91 (m, 1 H), 1.96-2.04 (m, 1 H), 2.40-2.48 (m, 2 H), 2.82-2.86 (m, 1 H), 2.91-2.96 (m, 1 H), 3.13-3.17 (m, 2

H), 3.21-3.24 (m, 1 H), 3.87 (s, 3 H), 3.89 (s, 3 H), 4.35 (d, J=14.4 Hz, 1 H), 4.76 (d, J=14.4 Hz, 1 H), 5.54 (d, J=10.3 Hz, 1 H), 5.85-5.91 (m, 1 H), 6.74-6.76 (m, 2 H), 6.80-6.82 (m, 1 H); $^{13}$C NMR δ d 34.5, 41.8, 43.5, 55.8, 55.9, 110.9 (×2), 120.3, 127.8, 129.0; u 24.7, 26.9, 43.8, 50.6, 128.6, 148.5, 149.2, 171.1, 177.5; IR 2936 (s), 2253 (m), 1706 (s), 1627 (s) cm$^{-1}$; HRMS calcd for $C_{19}H_{24}NO_5$ 346.1654, 346.1670 obsd.

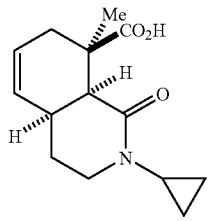

2-Cyclopropyl-8-methyl-1-oxo-1,2,3,4,4a,7,8,8a-octahydroisoquinoline-8-carboxylic acid 3{2}. Amino diene 1{2} (98.2 mg, 0.716 mmol) and citraconic anhydride (120.4 mg, 1.07 mmol) were dissolved in dichloroethane (2.0 mL) and heated at 165° C. for 1.5 h under microwave irradiation. The solvent was removed in vacuo and the residue chromatographed to give 3{2} as a sticky yellow gum (91.4 mg, 0.367 mmol, 51% yield). TLC $R_f$=0.57 ("wet ether"); mp=156.0-159.5° C.; $^1$H NMR δ 0.40-0.45 (m, 1 H), 0.67-0.72 (m, 2 H), 0.77-0.83 (m, 1 H), 1.23 (s, 3 H), 1.89-2.00 (complex, 3 H), 2.53-2.80 (m, 1 H), 2.94 (d, J=5.6 Hz, 1 H), 3.03-3.17 (m, 2 H), 5.49 (d, J=9.6 Hz, 1 H), 5.72-5.78 (m, 1 H); $^{13}$C NMR δ d 23.1, 29.9, 30.3, 47.6, 126.0, 128.7; u 6.0, 7.1, 27.4, 30.1, 42.0, 44.5, 172.1, 181.7; IR 3448 (m), 3016 (s), 2935 (s), 1701 (s), 1627 (s) cm$^{-1}$; HRMS calcd for $C_{14}H_{20}NO_3$ 250.1443, 250.1452 obsd.

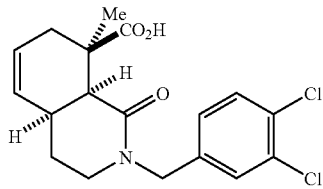 [SMILES: C[C@@]1(C(=O)O)CC=C[C@@H]2CCN(Cc3ccc(Cl)c(Cl)c3)C(=O)[C@@H]21]

2-(3,4-Dichlorobenzyl)-8-methyl-1-oxo-1,2,3,4,4a,7,8,8a-octahydroisoquinoline-8-carboxylic acid 3{5}a and WA. Amino diene 1{5} (200.0 mg, 0.781 mmol) and citraconic anhydride (175.0 mg, 1.56 mmol) were mixed together neat and heated at 100° C. for 5.5 h in a conventional oil bath. The residue was dissolved in $CH_2Cl_2$ and chromatographed to give 3{5}a and 3{5}b as a sticky, tan-colored foam (219.8 mg, 0.597 mmol, 76% yield). TLC $R_f$=0.71 ("wet ether"); mp=186.0-189.0° C.; $^1$H NMR δ 1.27 (s, 3H); 1.90-2.09 (m, 3 H), 2.55-2.64 (m, 1 H), 2.79-2.85 (m, 1 H), 3.04-3.08 (m, 3 H), 4.13 (d, J=15.2 Hz, 1 H), 4.84 (d, J=15.2 Hz, 1 H), 5.53 (d, J=9.8 Hz, 1 H), 5.80-5.84 (m, 1 H), 6.99 (dd, J=2.0, 8.1 Hz, 2 H), 7.20 (d, J=2.0 Hz, 1 H), 7.34 (d, J=8.4 Hz, 1 H); $^{13}$C NMR δ d 23.1, 30.6, 47.3, 126.2, 127.1, 128.9, 129.4, 130.5; u 26.9, 30.2, 42.2, 44.4, 49.6, 131.2, 135.0, 137.3, 170.3, 181.7; IR 3054 (m), 2918 (m), 2254 (m), 1698 (s), 1629 (s) cm$^{-1}$; HRMS calcd for $C_{18}H_{20}Cl_2NO_3$ 368.0820, 368.0824 obsd.

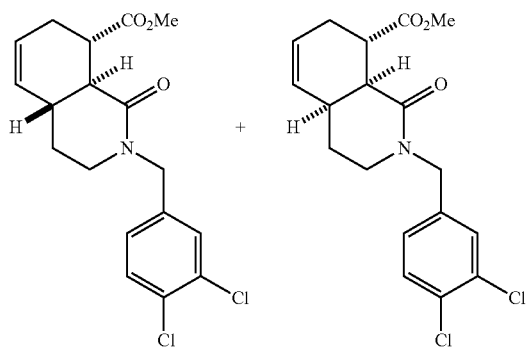

Methyl 2-(3,4-dichlorobenzyl)-1-oxo-1,2,3,4,4a,7,8,8a-octahydroisoquinoline-8-carboxylate 4a and 4b. Amino diene 1{5} (200.0 mg, 0.781 mmol) and dimethyl fumarate (150.0 mg, 1.04 mmol) were dissolved in dichloroethane (3.5 mL) and heated at 165° C. for 1.5 h under microwave irradiation. The solvent was removed in vacuo and the residue chromatographed to give the diastereomeric mixture 4a and 4b as a colorless oil (261.7 mg, 0.711 mmol, 91% yield). TLC $R_f$=0.84 (5% MeOH in $CHCl_3$); $^1$H NMR δ 1.69 (m, 1H), 1.83 (m, 1H), 2.00 (m, 1H), 2.20 (m, 1H), 2.30-2.33 (m, 1H), 2.42 (m 1H), 2.54-2.61 (m, 1H), 3.14-3.19 (m, 1H), 3.20-3.24 (m, 1H), 3.30 (m, 1H), 3.58 (m, 1H), 3.72 (s, 3 H), 3.80 (m, 1H); $^{13}$C NMR δ 23.5, 27.0, 28.9, 29.8, 30.0, 34.6, 39.4, 40.4, 41.7, 44.6, 45.5, 45.6, 48.8, 49.8, 51.9, 126.0, 126.9, 127.4, 127.5, 128.5, 128.7, 129.3, 129.8, 130.4, 130.6, 131.2, 131.4, 132.5, 132.6, 137.4, 137.4, 170.0, 170.9, 174.7, 176.8; IR 3022, 2945, 2934, 2845, 1734, 1639 cm$^{-1}$; HRMS calcd for $C_{18}H_{20}Cl_2NO_3$ 368.0820, 368.0825 obsd.

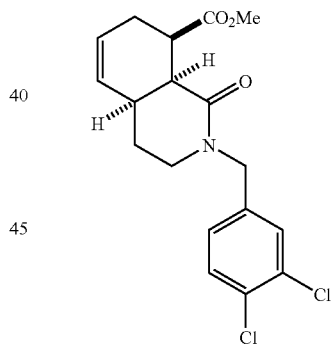

Methyl 2-(3,4-dichlorobenzyl)-1-oxo-1,2,3,4,4a,7,8,8a-octahydroisoquinoline-8-carboxylate 5. To the carboxylic acid scaffold NS) (67.1 mg, 0.189 mmol) in MeOH (0.5 mL) and benzene (1.5 mL) was added trimethylsilyldiazomethane solution (0.47 mL, 2 M in ether, 0.945 mmol) and the reaction stirred for 14 h at rt. The solvent was removed in vacuo and the residue chromatographed to 5 as a colorless oil (68.8 mg, 0.187 mmol, 98% yield). TLC $R_f$=0.09 (25% EtOAc in Hexanes); $^1$H NMR δ 1.82-1.89 (m, 1 H), 1.99-2.08 (m, 1 H), 2.36-2.39 (m, 1 H), 2.62-2.67 (m, 1 H), 2.86 (m, 1 H), 3.01-3.13 (m, 2 H), 3.42-3.44 (m, 1 H), 3.77 (s, 3 H), 4.15 (d, J=15.2 Hz, 1 H), 4.83 (d, J=15.2 Hz, 1 H), 5.55 (dd, J=0.8, 10.1 Hz, 1 H), 5.87-5.91 (m, 1 H), 6.99 (dd, J=1.6, 7.9 Hz, 1 H), 7.21 (d, J=1.2 Hz, 1 H), 7.34 (d, J=8.3 Hz, 1 H); $^{13}$C NMR δ d 34.2, 41.0, 42.7, 51.8, 126.9, 127.6, 129.2, 129.3, 130.4; u 23.6, 27.2, 44.1, 49.3, 131.0, 132.4, 137.2, 169.6, 174.1; IR 3509 (w), 3021 (m), 2928 (m), 2869 (m), 2250 (m), 1736 (s), 1634 (s) cm$^{-1}$; HRMS calcd for $C_{18}H_{20}Cl_2NO_3$ 368.0820, 368.0825 obsd.

General procedure for the coupling of carboxylic acid scaffolds 2{1-6} with amines 6{1-12}. Each reaction tube of a 24-position Bohdan Miniblock XT was charged with EDC.HCl (28.8 mg, 0.15 mmol). The air atmosphere was exchanged for argon and $CH_2Cl_2$ (0.3 mL) was added. A solution of the carboxylic acid scaffold 2{1-6} (0.10 mmol) in $CH_2Cl_2$ (0.4 mL) was added via syringe followed by a solution of the amine 6{1-12} (0.20 mmol) and DMAP (mg, 0.02 mmol) in $CH_2Cl_2$ (0.4 mL). The reactions were stirred at room temperature (rt) for 14 h then partitioned between $CH_2Cl_2$ and water in hydrophobic phase separator tubes, which allowed the halogenated solvent layer to pass through. The aqueous layers were washed with $CH_2Cl_2$ (2×3 mL). The combined organics were passed through 1,000 mg silica SPE tubes, eluting with $CH_2Cl_2$ (7 mL) then $CH_2Cl_2$:acetone (1:1, 7 mL) to yield the crude amides 7{1-72}. The crude amides were evaporated in a Genevac EZ-2 Plus parallel evaporator and subjected to mass-directed preparative HPLC purification to give the pure amides 7{1-72}. Characterization of representative library examples:

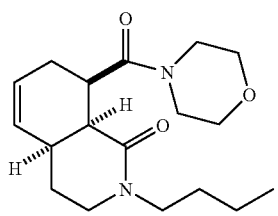 [SMILES: CCCCN1CC[C@H]2C=CC[C@@H](C(=O)N3CCOCC3)[C@H]2C1=O]

2-Butyl-8-(morpholine-4-carbonyl)-2,3,4,4a,8,8a-hexahydroisoquinolin-1(7H)-one 7{1}. $^1$H NMR δ 0.89 (t, J=8.0 Hz, 3 H), 1.21 (q, J=8.0 Hz, 2 H), 1.42-1.50 (m, 2 H), 1.84-2.01 (m, 2 H), 2.14-2.20 (m, 1 H), 2.40-2.49 (m, 1 H), 2.78-2.80 (m, 1 H), 2.89-2.97 (m, 2 H), 3.06-3.13 (m, 2 H), 3.27-3.34 (m, 1 H), 3.47-3.53 (m, 2 H), 3.55-3.60 (m, 1 H), 3.65-3.71 (m, 6 H), 5.53 (dd, J=2.3, 8.0 Hz, 1 H), 5.89-5.94 (m, 1 H); $^{13}$C NMR δ d 13.9, 34.6, 38.5, 42.6, 127.5, 128.9; u 20.0, 25.0, 27.3, 29.1 (×2), 44.6, 47.3 (×2), 66.9 (×2), 168.2, 172.3.

2-Cyclopropyl-8-(morpholine-4-carbonyl)-2,3,4,4a,8,8a-hexahydroisoquinolin-1(7H)-one 7{13}. $^1$H NMR δ 0.55-0.59 (m, 2 H), 0.70-0.81 (m, 2 H), 1.80-1.88 (m, 1 H), 1.99-2.06 (m, 1 H), 2.14-2.21 (m, 1 H), 2.35-2.44 (m, 1 H), 2.69-2.75 (m, 2 H), 2.86-2.89 (m, 1 H), 3.00-3.04 (m, 1 H), 3.09-3.15 (m, 1 H), 3.19-3.25 (m, 1 H), 3.50-3.56 (m, 1 H), 3.65-3.70 (m, 6 H), 5.51 (dd, J=2.2, 10.1 Hz, 1 H), 5.85-5.90 (m, 1 H); $^{13}$C NMR δ d 30.1, 34.1, 38.3, 42.9, 127.7, 128.3; u 6.0, 6.6, 25.1 (×2), 27.3, 44.8 (×2), 66.9 (×2), 170.7, 172.2.

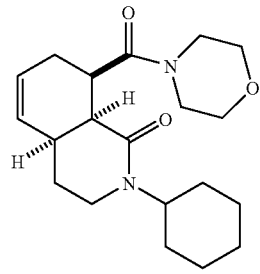 [SMILES: O=C([C@@H]1CC=C[C@@H]2CCN(C3CCCCC3)C(=O)[C@@H]21)N1CCOCC1]

2-Cyclohexyl-8-(morpholine-4-carbonyl)-2,3,4,4a,8,8a-hexahydroisoquinolin-1(7H)-one 7{25}. $^1$H NMR δ 0.99-1.10 (m, 1 H), 1.30-1.38 (m, 4 H), 1.53-1.55 (m, 1 H), 1.61-1.63 (m, 2 H), 1.73-1.86 (m, 3 H), 1.91-1.97 (m, 1 H), 2.12-2.20 (m, 1 H), 2.41-2.50 (m, 1 H), 2.75-2.81 (m, 1 H), 2.89-2.95 (m, 2 H), 3.10-3.13 (m, 2 H), 3.47-3.51 (m, 2 H), 3.67-3.77 (m, 6 H), 4.45-4.53 (m, 1 H), 5.49 (dd, J=2.2, 10.1 Hz, 1 H), 5.90-5.95 (m, 1 H); $^{13}$C NMR δ d 34.1, 39.0, 43.0, 52.2, 127.4, 129.2; u 24.8, 25.6 (×2), 25.7, 27.5, 29.3, 30.0 (×2), 38.1 (×2), 66.9 (×2), 167.8, 172.4.

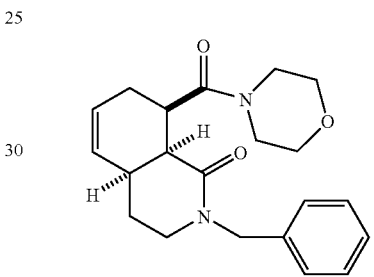

2-Benzyl-8-(morpholine-4-carbonyl)-2,3,4,4a,8,8a-hexahydroisoquinolin-1(7H)-one 7{37}. $^1$H NMR δ 1.84-1.92 (m, 1 H), 1.94-2.00 (m, 1 H), 2.21-2.27 (m, 1 H), 2.50-2.59 (m, 1 H), 2.77-2.83 (m, 1 H), 2.98-3.07 (m, 3 H), 3.12-3.19 (m, 1 H), 3.51-3.54 (m, 2 H), 3.66-3.74 (m, 6 H), 4.35 (d, J=14.6 Hz, 1 H), 4.83 (d, J=14.6 Hz, 1 H), 5.50 (dd, J=1.9, 10.1 Hz, 1 H), 5.88-5.93 (m, 1 H), 7.18-7.31 (m, 5 H); $^{13}$C NMR δ d 34.6, 38.5, 42.6, 127.2, 127.7, 127.9 (×2), 128.5 (×3); u 25.2 (×2), 27.2, 44.2, 50.4 (×2), 66.9 (×2), 137.1, 168.8, 172.3.

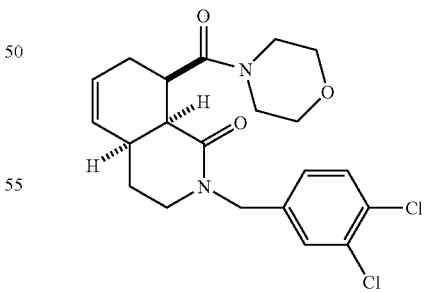

2-(3,4-Dichlorobenzyl-8-(morpholine-4-carbonyl)-2,3,4,4a,8,8a-hexahydroisoquinolin-1(7H)-one 7{49}. $^1$H NMR δ 1.87-1.95 (m, 1 H), 2.05-2.12 (m, 1 H), 2.25-2.31 (m, 1 H), 2.48-2.57 (m, 1 H), 2.82-2.84 (m, 1 H), 2.97-3.00 (m, 1 H), 3.07-3.13 (m, 2 H), 3.16-3.22 (m, 1 H), 3.51-3.52 (m, 2 H), 3.67-3.70 (m, 6 H), 4.18 (d, J=14.9 Hz, 1 H), 4.89 (d, J=14.9 Hz, 1 H), 5.55 (dd, J=2.0, 10.0 Hz, 1 H), 5.90-5.95 (m, 1 H), 7.05 (dd, J=2.1, 10.2 Hz, 1 H), 7.30 (d, J=2.0 Hz, 1 H), 7.37 (d, J=8.5 Hz, 1 H); ¹³C NMR δ d 34.5, 38.4, 42.4, 127.1, 127.9, 128.2, 129.5, 130.5; u 25.2 (×2), 27.2, 44.8, 49.5 (×2), 66.9 (×2), 131.2, 132.6, 137.5, 169.3, 172.1.

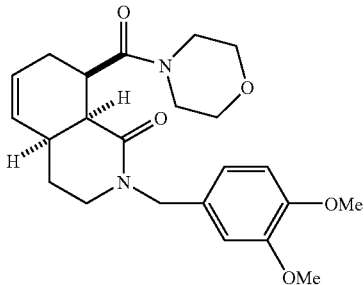 [SMILES: COc1ccc(CN2CC[C@H]3C=CC[C@@H](C(=O)N4CCOCC4)[C@H]3C2=O)cc1OC]

2-(3,4-Dimethoxybenzyl-8-(morpholine-4-carbonyl)-2,3, 4,4a,8,8a-hexahydroisoquinolin-1(7H)-one 7{61}. ¹H NMR δ 1.84-1.92 (m, 1 H), 1.95-2.02 (m, 1 H), 2.21-2.28 (m, 1 H), 2.50-2.59 (m, 1 H), 2.80-2.81 (m, 1 H), 2.97-3.06 (m, 3 H), 3.09-3.16 (m, 1 H), 3.52-3.54 (m, 2 H), 3.68-3.73 (m, 6 H), 3.86 (s, 3 H), 3.87 (s, 3 H), 4.08 (d, J=14.3 Hz, 1 H), 4.99 (d, J=14.3 Hz, 1 H), 5.50 (dd, J=2.0, 9.9 Hz, 1 H), 5.85-5.90 (m, 1 H), 6.72-6.79 (m, 3 H); ¹³C NMR δ d 34.6, 38.6, 42.6, 55.9 (×2), 110.8, 111.0, 120.3, 128.0, 128.3; u 25.1 (×2), 27.2, 44.0, 50.1 (×2), 66.9 (×2), 129.7, 148.3, 149.2, 168.8, 172.3.

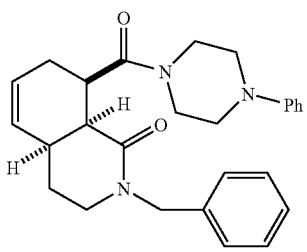 [SMILES: O=C1[C@H]2[C@H](C=CC[C@H]2C(=O)N2CCN(c3ccccc3)CC2)CCN1Cc1ccccc1]

2-Benzyl-8-(4-phenylpiperazine-1-carbonyl)-2,3,4,4a,8, 8a-hexahydroisoquinolin-1(7H)-one 7{38}. ¹H NMR δ 1.64-1.76 (m, 1 H), 1.86-1.95 (m, 1 H), 1.98-2.05 (m, 1 H), 2.26-2.30 (m, 1 H), 2.54-2.62 (m, 1 H), 2.85-2.86 (m, 1 H), 3.05-3.28 (8 H), 3.68-3.74 (m, 2 H), 3.81-3.96 (m, 1 H), 4.37 (d, J=14.6 Hz, 1 H), 4.85 (d, J=14.6 Hz, 1 H), 5.53 (dd, J=1.8, 9.9 Hz, 1 H), 5.91-5.96 (m, 1 H), 6.90-6.96 (m, 3 H), 7.20-7.32 (m, 7 H); ¹³C NMR δ d 34.6, 38.6, 42.8, 116.5 (×2), 120.3, 127.2, 127.7, 127.9 (×2), 128.4 (×2), 128.6, 129.2 (×2); u 25.2 (×2), 27.2, 44.2 (×2), 49.6, 50.3 (×2), 137.1, 151.1, 168.8, 172.1.

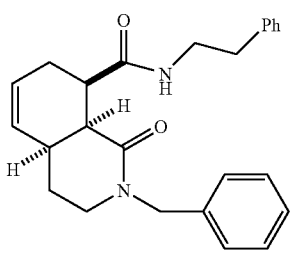 [SMILES: O=C(NCCc1ccccc1)[C@@H]1CC=C[C@@H]2CCN(Cc3ccccc3)C(=O)[C@@H]21]

2-Benzyl-8-(phenethyl-4-carbonyl)-2,3,4,4a,8,8a-hexahydroisoquinolin-1(7H)-one 7{39}. ¹H NMR δ 1.75-1.81 (m, 1 H), 1.92-2.00 (m, 2 H), 2.26-2.30 (m, 1 H), 2.65-2.70 (m, 1 H), 2.80-2.88 (m, 3 H), 3.08 (dd, J=3.7, 8.7 Hz, 2 H), 3.52-3.58 (m, 2 H), 4.43 (d, J=14.6 Hz, 1 H), 5.55 (dd, J=1.7, 9.9 Hz, 1 H), 5.81-5.85 (m, 1 H), 7.15-7.30 (m, 10 H), 7.37 (br s, 1 H); ¹³C NMR δ d 35.6, 42.4, 44.9, 426.2, 127.3, 127.6 (×2), 128.4 (×3), 128.5 (×2), 128.7, 128.9 (×2); u 25.3, 27.3, 35.6, 40.9, 44.2, 50.3, 136.9, 139.5, 170.5, 174.0.

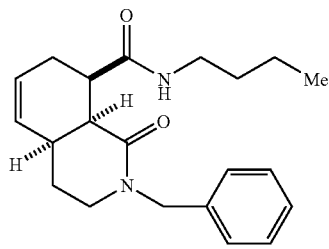 [SMILES: CCCCNC(=O)[C@@H]1CC=C[C@@H]2CCN(Cc3ccccc3)C(=O)[C@@H]21]

2-Benzyl-N-butyl-1-oxo-1,2,3,4,4a,7,8,8a-octahydroisoquinoline-8-carboxamide 7{40}. ¹H NMR δ 0.92 (t, J=7.3 Hz, 3 H), 1.34-1.41 (m, 2 H), 1.48-1.55 (m, 2 H), 1.77-1.87 (m, 1 H), 1.92-2.03 (m, 1 H), 2.34-2.40 (m, 2 H), 2.71-2.75 (m, 1 H), 2.78-2.86 (m, 1 H), 3.08-3.11 (m, 2 H), 3.23-3.36 (m, 3 H), 4.46 (d, J=14.9 Hz, 1 H), 4.69 (d, J=14.9 Hz, 1 H), 5.56 (dd, J=1.8, 10.1 Hz, 1 H), 5.85-5.88 (m, 1 H), 7.16-7.18 (m, 2 H), 7.25-7.32 (m, 3 H), 7.55 (br s, 1 H); ¹³C NMR δ d 13.8, 35.7, 42.5, 45.3, 127.3, 127.7 (×2), 128.4, 128.5 (×2), 128.9; u 20.2, 25.7, 27.2, 31.6, 39.4, 44.3, 50.4, 136.8, 170.8, 174.1.

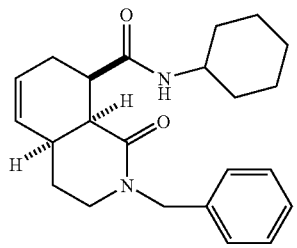

2-Benzyl-N-cyclohexyl-1-oxo-1,2,3,4,4a,7,8,8a-octahydroisoquinoline-8-carboxamide 7{41}. ¹H NMR δ 1.12-1.26 (m, 3 H), 1.32-1.42 (m, 2 H), 1.57-1.62 (m, 1 H), 1.66-1.82 (m, 3 H), 1.90-1.99 (m, 4 H), 2.33-2.36 (m, 2 H), 2.70-2.84 (m, 2 H), 3.06-3.10 (m, 2 H), 3.20-3.22 (m, 1 H), 3.74-3.83 (m, 1 H), 4.50 (d, J=14.7 Hz, 1 H), 4.65 (d, J=14.6 Hz, 1 H), 5.55 (dd, J=1.8, 9.9 Hz, 1 H), 5.83-5.88 (m, 1 H), 7.16-7.18 (m, 2 H), 7.24-7.32 (m, 3 H), 7.43 (br s, 1 H); ¹³C NMR δ d 35.7, 42.5, 45.2, 48.1, 127.3, 127.8 (×2), 128.3, 128.5 (×2), 128.8; u 24.9 (×2), 25.7, 25.8, 27.2, 32.9 (×2), 44.4, 50.4, 136.9, 170.8, 173.1.

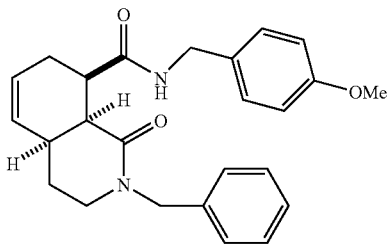

2-Benzyl-N-(4-methoxybenzyl)-1-oxo-1,2,3,4,4a,7,8,8a-octahydroisoquinoline-8-carboxamide 7{42}. ¹H NMR δ 1.75-1.81 (m, 1 H), 1.91-2.01 (m, 1 H), 2.35-2.37 (m, 2 H), 2.73-2.80 (m, 2 H), 3.04-3.08 (m, 2 H), 3.28-3.29 (m, 1 H), 3.79 (s, 3 H), 4.35-4.40 (m, 2 H), 4.45-4.53 (m, 2 H), 4.59 (d, J=14.7 Hz, 1 H), 5.56 (dd, J=2.0, 9.9 Hz, 1 H), 5.84-5.87 (m, 1 H), 6.85 (d, J=8.6 Hz, 2 H), 7.15 (d, J=8.4 Hz, 2 H), 7.24-7.31 (m, 5 H), 7.61 (br s, 1 H); ¹³C NMR δ d 35.5, 42.5, 44.7, 55.3, 113.9 (×2), 127.3, 127.7 (×2), 128.4, 128.5 (×2), 128.6, 129.1 (×2); u 25.4, 27.2, 43.0, 44.3, 50.4, 131.1, 136.9, 158.7, 170.6, 174.0.

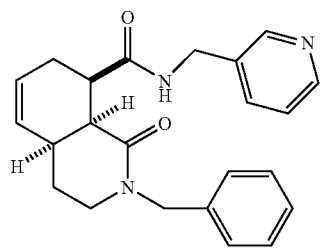

2-Benzyl-N-(pyridin-3-ylmethyl)-1-oxo-1,2,3,4,4a,7,8,8a-octahydroisoquinoline-8-carboxamide 7{43}. ¹H NMR δ 1.76-1.83 (m, 1 H), 1.93-2.01 (m, 1 H), 2.36-2.41 (m, 2 H), 2.77-2.82 (m, 2 H), 3.08-3.11 (m, 2 H), 3.25-3.27 (m, 1 H), 4.45 (d, J=14.9 Hz, 1 H), 4.50-4.53 (m, 2 H), 4.65 (d, J=14.9 Hz, 1 H), 5.57 (dd, J=1.7, 10.0 Hz, 1 H), 5.84-5.98 (m, 1 H), 7.16 (d, J=6.8 Hz, 2 H), 7.23-7.32 (m, 4 H), 7.73 (d, J=7.8 Hz, 1 H), 8.22 (br s, 1 H), 8.49 (d, J=6.3 Hz, 1 H), 8.57 (d, J=2.0 Hz, 1 H); ¹³C NMR δ d 35.7, 42.5, 45.3, 123.5, 127.3, 127.6 (×2), 128.3, 128.6 (×2), 128.8, 135.5, 148.5, 149.1; u 25.7, 27.2, 41.0, 44.3, 50.5, 134.6, 136.7, 170.7, 174.5.

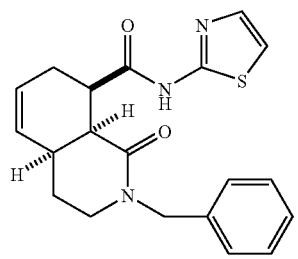

2-Benzyl-N-(thiazol-2-yl)-1-oxo-1,2,3,4,4a,7,8,8a-octahydroisoquinoline-8-carboxamide 7{44}. ¹H NMR δ 1.81-1.87 (m, 1 H), 1.94-2.04 (m, 1 H), 2.49-2.53 (m, 2 H), 2.84-2.902 (m, 1 H), 2.96-3.00 (m, 1 H), 3.09-3.12 (m, 2 H), 3.30-3.31 (m, 1 H), 4.41 (d, J=14.7 Hz, 1 H), 4.80 (d, J=14.6 Hz, 1 H), 5.58 (d, J=10.1 Hz, 1 H), 5.88-5.93 (m, 1 H), 6.93 (d, J=3.5 Hz, 1 H), 7.17 (d, J=8.1 Hz, 2 H), 7.23-7.31 (m, 3 H), 7.46 (d, J=7.8 Hz, 1 H), 12.55 (br s, 1 H); ¹³C NMR δ d 35.6, 42.3, 46.0, 113.2, 127.4, 127.8 (×2), 128.0, 128.5 (×2), 128.9, 137.5; u 25.6, 27.2, 43.9, 50.6, 136.5, 159.0, 170.4, 172.0.

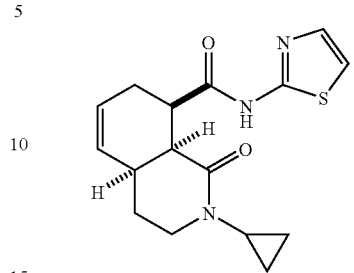

2-Cyclopropyl-N-(thiazol-2-yl)-1-oxo-1,2,3,4,4a,7,8,8a-octahydroisoquinoline-8-carboxamide 7{20}. ¹H NMR δ 0.46-0.52 (m, 1 H), 0.66-0.84 (m, 3 H), 1.83-1.88 (m, 1 H), 1.90-1.99 (m, 2 H), 2.42-2.46 (m, 2 H), 2.64-2.70 (m, 1 H), 2.79-2.87 (m, 1 H), 2.90-2.94 (m, 1 H), 3.08-3.21 (m, 3 H), 5.58 (dd, J=1.8, 10.1 Hz, 1 H), 5.86-5.91 (m, 1 H), 6.93 (d, J=3.5 Hz, 1 H), 7.45 (d, J=3.5 Hz, 1 H), 12.15 (br s, 1 H); ¹³C NMR δ d 30.2, 35.2, 42.6, 45.7, 113.2, 127.9, 128.8, 137.5; u 6.4, 6.8, 25.3, 27.4, 44.4, 158.8, 172.0, 172.4.

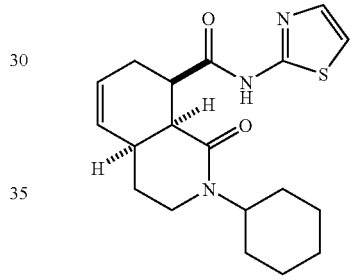

2-Cyclohexyl-N-(thiazol-2-yl)-1-oxo-1,2,3,4,4a,7,8,8a-octahydroisoquinoline-8-carboxamide 7{32}. ¹H NMR δ 1.00-1.09 (m, 1 H), 1.30-1.40 (m, 4 H), 1.54-1.66 (m, 3 H), 1.74-1.78 (m, 2 H), 1.84-2.02 (m, 2 H), 2.41-2.46 (m, 2 H), 2.78-2.87 (m, 1 H), 2.92-2.97 (m, 1 H), 3.01-3.08 (m, 1 H), 3.15-3.21 (m, 2 H), 4.49-4.54 (m, 1 H), 5.56 (d, J=9.8 Hz, 1 H), 5.87-5.92 (m, 1 H), 6.92 (d, J=3.6 Hz, 1 H), 7.44 (d, J=3.5 Hz, 1 H), 12.70 (br s, 1 H); ¹³C NMR δ d 34.9, 42.4, 46.0, 52.9, 113.1, 127.8, 128.8, 137.5; u 25.4, 25.6 (×2), 25.7, 27.4, 29.5, 29.6, 38.2, 159.0, 169.5, 172.2.

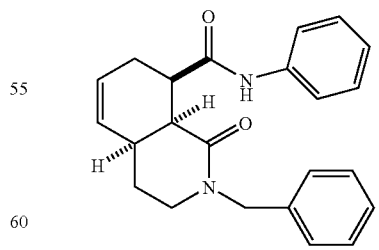

2-Benzyl-N-phenyl-1-oxo-1,2,3,4,4a,7,8,8a-octahydroisoquinoline-8-carboxamide 7{45}. ¹H NMR δ 1.81-1.85 (m, 1 H), 1.94-2.02 (m, 1 H), 2.46-2.55 (m, 2 H), 2.83-2.85 (m, 1 H), 2.93-2.97 (m, 1 H), 3.12-3.14 (m, 2 H), 3.22-3.26 (m, 1 H), 4.48 (d, J=14.9 Hz, 1 H), 4.78 (d, J=14.6 Hz, 1 H), 5.58 (d, J=9.8 Hz, 1 H), 5.90-5.93 (m, 1 H), 7.06 (d, J=3.5 Hz, 1 H), 7.17 (d, J=7.1 Hz, 2 H), 7.26-7.32 (m, 5 H), 7.636 (d, J=9.4 Hz, 2 H), 10.89 (br s, 1 H); $^{13}$C NMR δ d 36.1, 42.5 (×2), 120.0 (×2), 123.6, 127.4, 127.7 (×2), 128.1, 128.6 (×2), 128.8 (×2), 129.3; u 26.6, 27.2, 44.4, 50.7, 136.6, 138.9, 171.4, 172.5.

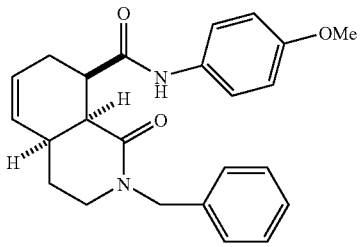

2-Benzyl-N-(4-methoxyphenyl)-1-oxo-1,2,3,4,4a,7,8,8a-octahydroisoquinoline-8-carboxamide 7{46}. $^1$H NMR δ 1.80-1.85 (m, 1 H), 1.93-2.01 (m, 1 H), 2.46-2.50 (m, 2 H), 2.81-2.85 (m, 1 H), 2.90-2.95 (m, 1 H), 3.11-3.14 (m, 2 H), 3.22-3.24 (m, 1 H), 3.78 (s, 3 H), 4.47 (d, J=14.9 Hz, 1 H), 4.77 (d, J=14.9 Hz, 1 H), 5.57 (dd, J=1.9, 10.0 Hz, 1 H), 5.88-5.93 (m, 1 H), 6.85 (d, J=9.1 Hz, 2 H), 7.17 (d, J=8.1 Hz, 2 H), 7.25-7.29 (m, 3 H), 7.54 (d, J=9.1 Hz, 2 H), 10.63 (br s, 1 H); $^{13}$C NMR δ d 36.1, 42.5 (×2), 55.5, 114.0 (×2), 121.6 (×2), 127.4, 127.7 (×2), 128.1, 128.6 (×2), 129.3; u 26.5, 27.2, 44.3, 50.6, 132.2, 136.6, 155.9, 171.4, 172.2.

2-Benzyl-N-(2,4-dichlorophenyl)-1-oxo-1,2,3,4,4a,7,8,8a-octahydroisoquinoline-8-carboxamide 7{47}. $^1$H NMR δ 1.82-1.91 (m, 1 H), 2.00-2.05 (m, 1 H), 2.46-2.58 (m, 2 H), 2.89-2.95 (m, 2 H), 3.10-3.21 (m, 2 H), 3.38-3.48 (m, 1 H), 4.48 (d, J=14.4 Hz, 1 H), 4.68 (d, J=14.7 Hz, 1 H), 5.62 (d, J=10.4 Hz, 1 H), 5.89-5.94 (m, 1 H), 7.15-7.36 (complex, 7 H), 8.43 (d, J=9.1 Hz, 2 H), 9.47 (br s, 1 H); $^{13}$C NMR δ d 35.4, 42.6, 45.8, 122.9, 127.4, 127.7, 127.8 (×2), 128.3, 128.5, 128.6 (×2), 128.7; u 25.3, 27.3, 44.2, 50.4, 124.1, 128.7, 134.2, 136.8, 170.2, 172.5.

2-Benzyl-N-(2,4-dichlorophenyl)-1-oxo-1,2,3,4,4a,7,8,8a-octahydroisoquinoline-8-carboxamide 7{48}. $^1$H NMR δ 1.82-1.88 (m, 1 H), 1.94-2.04 (m, 1 H), 2.46-2.50 (m, 2 H), 2.84-2.90 (m, 1 H), 2.91-2.96 (m, 1 H), 3.13-3.17 (m, 2 H), 3.20-3.21 (m, 1 H), 4.45 (d, J=14.9 Hz, 1 H), 4.82 (d, J=14.6 Hz, 1 H), 5.58 (dd, J=1.8, 10.1 Hz, 1 H), 5.89-5.94 (m, 1 H), 7.17-7.19 (m, 2 H), 7.26-7.33 (m, 3 H), 7.40 (d, J=8.6 Hz, 1 H), 7.80 (dd, J=2.8, 8.8 Hz, 1 H), 7.99 (d, J=2.5 Hz, 1 H), 11.73 (br s, 1 H); $^{13}$C NMR δ d 36.1, 42.2, 48.5, 118.8, 118.9, 123.8, 127.5 (×2), 128.0, 128.6 (×2), 129.3, 131.6; u 26.6, 27.1, 44.2, 50.8, 121.3, 124.1, 136.2, 137.9, 171.4, 172.9.

Near-Neat Procedure Diels-Alder/Acylation Reaction Sequence

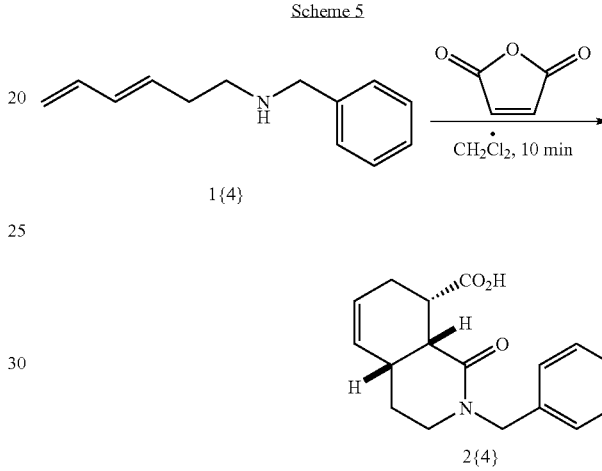

Reaction Scheme 5 shows a reaction where a diene 1{4} (4.9 g, 26 mmol) was dissolved in 5 mL dichloromethane in a 100 mL round bottom flask fitted with a magnetic stir bar. Maleic anhydride 2 (2.8 g, 29 mmol) was added to the reaction flask in 5 portions over 5 minutes with constant stirring (the reaction is exothermic and becomes violent if maleic anhydride is added all at once). After stirring for additional 5 minutes, 60 mL hexane was added to the reaction and the organic layer was decanted. The white solid residue was dissolved in 50 mL 20% dichloromethane/hexane solution which upon slow evaporation afforded 2{4} as colorless crystals (6.6 g, 23 mmol, 88% yield).

Synthesis of Analogs from N-Substituted Maleimides

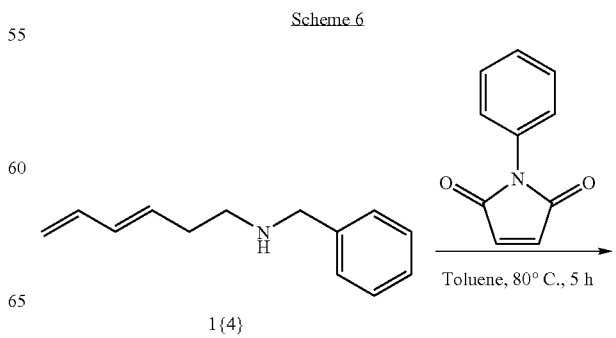

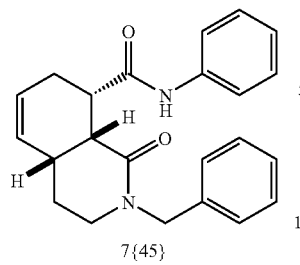

7{45}

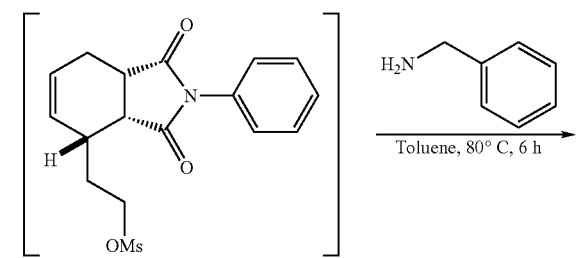

Reaction Scheme 6 shows a reaction where diene 1{4} (100 mg, 0.53 mmol) and N-phenylmaleimide (104 mg, 0.60 mmol) were dissolved in toluene (5 mL) in a 25 mL round bottom flask at room temperature. The reaction was stirred for 5 hours at 80° C. The reaction was cooled and then directly loaded onto a silica gel column. Chromatography with 20% EtOAc/hexane afforded 7{45} (164 mg, 0.45 mmol, 85% yield) as a white solid. The following compounds were also synthesized using Scheme 6.

7{73}

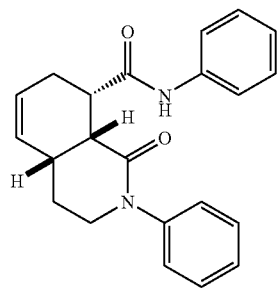

7{33}

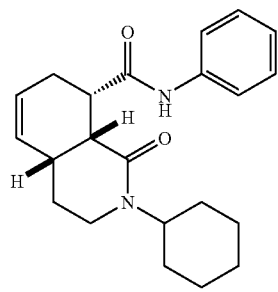

One Pot Three Component Synthesis of Analogs

Scheme 7

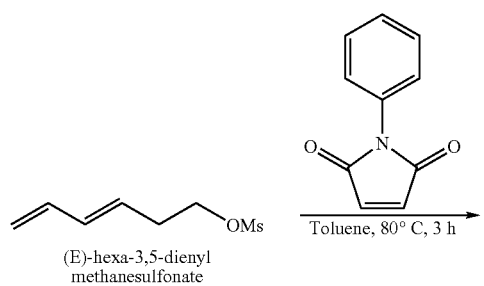

(E)-hexa-3,5-dienyl methanesulfonate

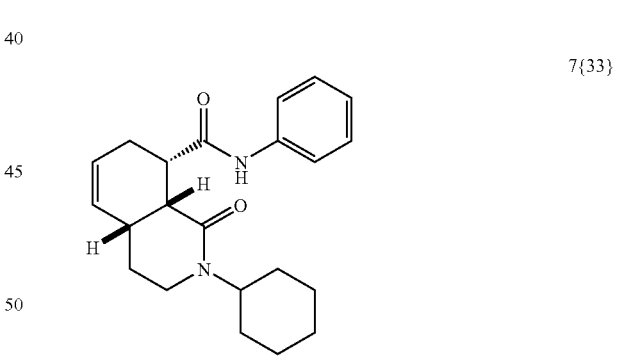

7{45}

Reaction Scheme 7 shows another diene, (E)-hexa-3,5-dienyl methanesulfonate (100 mg, 0.57 mmol) and N-phenylmaleimide (118 mg, 0.68 mmol) were dissolved in toluene (5 mL) in a 25 mL round bottom flask at room temperature. After stirring for 3 hours at 80° C., benzyl amine (0.18 mL, 177 mg, 1.65 mmol) was added and the reaction was stirred for additional 6 h at 80° C. The reaction was cooled and then directly loaded onto silica gel column. Chromatography with 20% EtOAc/hexane produced the corresponding analog 7{45} (160 mg, 0.44 mmol, 78% yield) as a white solid. The following compounds were also synthesized using Scheme 7.

7{33}

7{74}

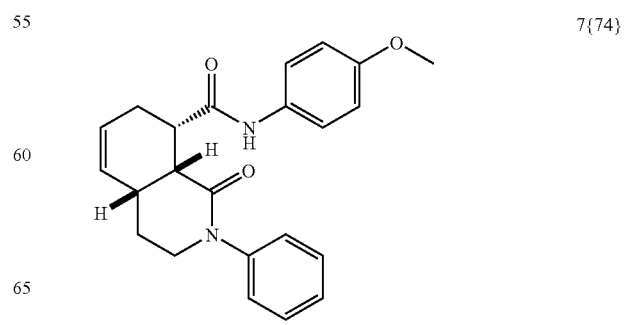

-continued

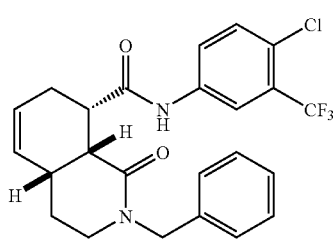

7{48}

Synthesis of the Lactone Carboxylic Acid Scaffold

Scheme 8

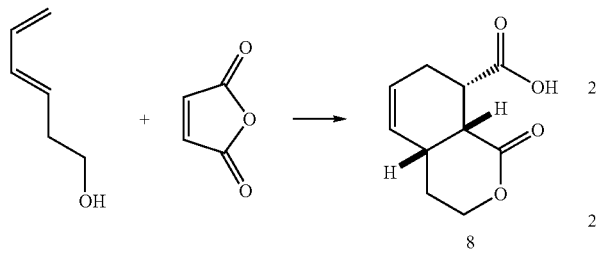

8

Reaction Scheme 8 produces a 1-Oxo-3,4,4a,7,8,8a-hexahydro-1H-isochromene-8-carboxylic acid 8. Maleic anhydride (2.30 g, 0.023 mol) was added to neat (E)-hexa-3,5-dien-1-ol (2.30 g, 0.023 mol) in a glass mortar and ground together with a pestal for 90 seconds to initiate the reaction. After the initially vigorous exothermic reaction was complete, the reaction was allowed to stand at rt for 30 minutes. The crude reaction mixture was chromatographed to yield the lactone carboxylic acid 8 as a white solid (3.42 g, 0.017 mol, 74% yield).

Coupling of Carboxylic Acid Scaffolds with Alcohols

Scheme 9

Reaction Scheme 9 produces a 4-chloro-3-(trifluoromethyl)phenyl 2-benzyl-1-oxo-1,2,3,4,4a,7,8,8a-octahydroisoquinoline-8-carboxylate 9{1}. A 20 mL scintillation vial was charged with a mixture of the carboxylic acid (145 mg, 0.51 mmol), the phenol (200 mg, 1.02 mmol), EDC.HCl (244 mg, 1.28 mmol) and DMAP (12 mg, 0.10 mmol). A solution of Et₃N (205 mg, 1.02 mmol) in CH₂Cl₂ (10 mL) was added, the vial was capped and stirred at rt for 14 h. The reaction was partitioned between water (25 mL) and CH₂Cl₂ (3×10 mL) and the combined organic layers were dried with Na₂SO₄. The crude product was purified by silica gel chromatography to afford the ester derivative 9{1} as a colorless oil (174 mg, 0.38 mmol, 74% yield).

Scheme 10

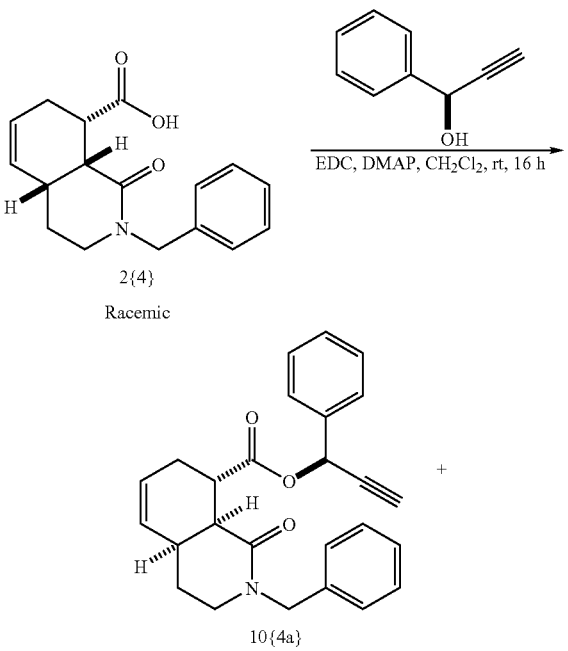

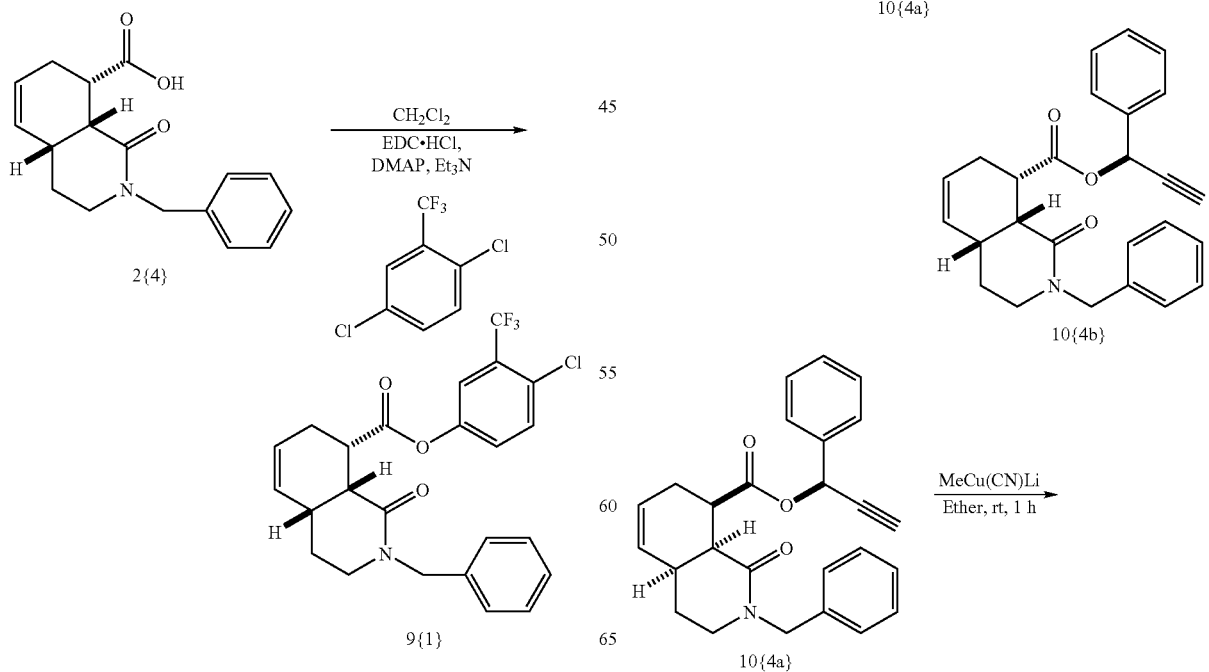

-continued

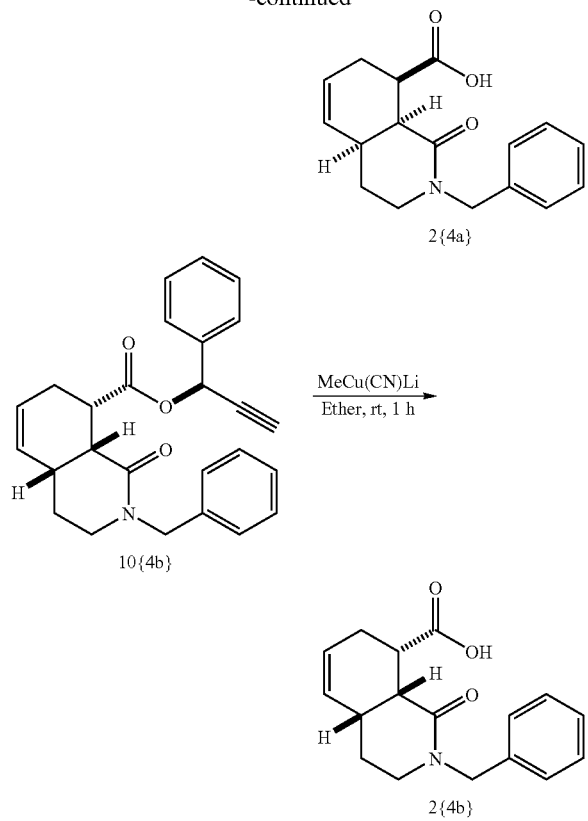

Scheme 10 illustrates the resolution of racemic carboxylic acid scaffold 2{4} to its enantiomers 2{4a} and 2{4b}. To a solution of carboxylic acid 2{4} (285 mg, 1.0 mmol) in dry CH$_2$Cl$_2$ (20 mL) were added EDC (382 mg, 2.0 mmol), DMAP (12 mg, 0.1 mmol) and (R)-1-Phenyl-2-propyn-1-ol (160 mg, 1.2 mmol) at room temperature. After stirring for 16 hour at room temperature the reaction solution was diluted with CH$_2$Cl$_2$ (80 mL), washed with water (20 mL×2) and the combined organic layers were dried over anhydrous MgSO$_4$. Evaporation of solvent followed by chromatography with 10% EtOAc/hexane gave 10{4a} (190 mg, 0.47 mmol, 95% yield) and 10(4b) (192 mg, 0.48 mmol, 96% yield) both as white foams.

10{4a}: R$_f$=0.25 (20% EtOAc/hexane); [α]$_D^{20}$ −37.0 (c 1.0, CHCl$_3$); $^1$H NMR (400 MHz, CDCl$_3$) δ 7.70-7.60 (2H, m), 7.40-7.10 (8H, m), 6.63 (1H, d, J=2.2 Hz), 5.90-5.83 (1H, m), 5.51 (1H, dd, J=10.0 Hz, 1 Hz), 4.64 (1H, d, J=14.7 Hz), 4.38 (1H, d, J=14.7 Hz), 3.34 (1H, dd, J=5.4 Hz, 3.3 Hz), 3.10-2.98 (1H, m), 2.85-2.65 (2H, m), 2.69 (1H, d, J=2.2 Hz), 2.46-2.38 (1H, m), 1.98-1.74 (2H, m); $^{13}$C NMR (100 MHz, CDCl$_3$) δ 172.6, 169.0, 137.3, 136.5, 129.1, 128.6, 128.5 (2), 128.4 (2), 127.9 (2), 127.8 (2), 127.6, 127.2, 80.5, 75.5, 65.0, 50.1, 43.8, 42.5, 41.1, 34.2, 27.3, 23.6; IR (neat) 2122, 1737, 1630, 1356 cm$^{-1}$.

10{4b}: R$_f$=0.20 (20% EtOAc/hexane); [α]$_D^{20}$ −15.0 (c 1.0, CHCl$_3$); $^1$H NMR (400 MHz, CDCl$_3$) δ 7.70-7.60 (2H, m), 7.40-7.15 (8H, m), 6.62 (1H, d, J=2.2 Hz), 5.85-5.78 (1H, m), 5.50 (1H, dd, J=10.0 Hz, 1.6 Hz), 4.75 (1H, d, J=14.7 Hz), 4.36 (1H, d, J=14.7 Hz), 3.47 (1H, dd, J=5.4 Hz, 3.2 Hz), 3.10-3.00 (2H, m), 2.85-2.60 (2H, m), 2.65 (1H, d, J=2.2 Hz), 2.48-2.28 (2H, m), 2.05-1.95 (1H, m), 1.82-1.77 (1H, m); $^{13}$C NMR (100 MHz, CDCl$_3$) δ 172.6, 169.1, 137.2, 137.0, 129.0, 128.7, 128.5 (2), 128.4 (2), 127.9 (2), 127.8, 127.7 (2), 127.2, 80.5, 75.3, 65.3, 50.3, 43.8, 42.8, 41.4, 34.3, 27.3, 23.6; IR (neat) 2123, 1734, 1630, 1356 cm$^{-1}$.

To a suspension of CuCN (134 mg, 1.5 mmol) in dry diethyl ether (10 mL), MeLi (1.0 mL, 1.5 mmol) was added slowly at 0° C. and stirred for 10 min when a clear homogeneous solution formed. Then a solution of 10{4a} (190 mg, 0.47 mmol) in dry diethyl ether was added to the reaction at 0° C. The reaction was warmed to the room temperature and stirred for 1 hour. The reaction was quenched with saturated NH$_4$Cl solution (5 mL) and acidified with a solution of HCl (1 mL, 10%) at room temperature. The reaction mixture was extracted with EtOAc (20 mL×3) and the combined organic layers were dried over anhydrous MgSO$_4$. Evaporation of solvent followed by chromatography with 50% EtOAc/hexane gave 2{4a} (104 mg, 0.36 mmol, 74% yield) as white solid. [α]$_D^{20}$ −21.4 (c 0.5, CHCl$_3$).

To a suspension of CuCN (134 mg, 1.5 mmol) in dry diethyl ether (10 mL), MeLi (1.0 mL, 1.5 mmol) was added slowly at 0° C. and stirred for 10 min when a clear homogeneous solution formed. Then a solution of 10{4b} (192 mg, 0.48 mmol) in dry diethyl ether was added to the reaction at 0° C. The reaction was warmed to the room temperature and stirred for 1 hour. The reaction was quenched with saturated NH$_4$Cl solution (5 mL) and acidified with a solution of HCl (1 mL, 10%) at room temperature. The reaction mixture was extracted with EtOAc (20 mL×3) and the combined organic layers were dried over anhydrous MgSO$_4$. Evaporation of solvent followed by chromatography with 50% EtOAc/hexane gave 2{4b} (112 mg, 0.39 mmol, 83% yield) as white solid. [α]$_D^{20}$ +22.0 (c 0.5, CHCl$_3$).

Synthesis of Enantio-Enriched n-alkyl-octahydroisoquinolin-1-one-8-carboxamides

The following enantio-enriched n-alkyl-octahydroisoquinolin-1-one-8-carboxamides were prepared from 2{4a} and 2{4b} following identical conditions reported for syntheses of the racemic carboxamides.

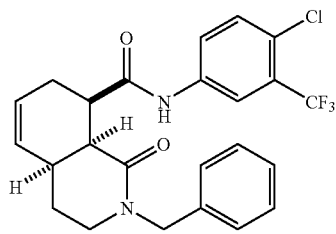

11789

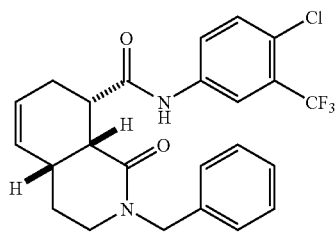

11790

-continued

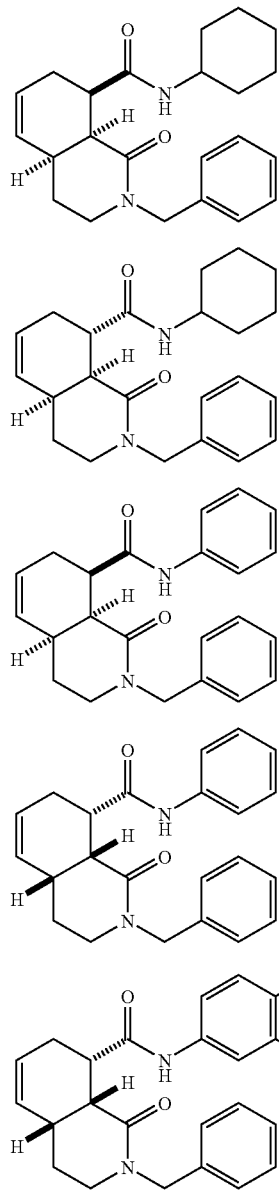

11789: [α]$_D^{20}$ +23.6(c 1.0, CHCl$_3$).[3]

11790: [α]$_D^{20}$ −23.2(c 1.0, CHCl$_3$); m.p. 180-182° C.; IR (neat) 2867, 1695, 1614, 1482, 1315 cm$^{-1}$; HRMS (ESI) m/z calcd for C$_{24}$H$_{23}$ClF$_3$N$_2$O$_2$ ([M+H]$^+$), 463.1400, found 463.1404.[1,2,3]

11791: [α]$_D^{20}$ +15.8 (c 1.0, CHCl$_3$).

11792: [α]$_D^{20}$ 16.0 (c 1.0, CHCl$_3$); IR (neat) 2853, 1635, 1535, 1490, 1353 cm$^{-1}$; $^1$H NMR (400 MHz, CDCl$_3$) δ 7.42 (1H, bs), 7.32-7.12 (5H, m), 5.88-5.80 (1H, m), 5.54 (1H, d, J=10.0 Hz), 4.64 (1H, d, J=14.8 Hz), 4.50 (1H, d, J=14.8 Hz), 3.83-3.70 (1H, m), 3.20 (1H, dd, J=2.5 Hz, 2.5 Hz), 3.08 (1H, d, J=8.3 Hz), 3.07 (1H, d, J=8.5 Hz), 2.72-2.65 (2H, m), 2.40-2.25 (2H, m), 2.00-1.10 (12H, m); $^{13}$C NMR (100 MHz, CDCl$_3$) δ 173.1, 170.8, 136.9, 128.8, 128.5 (2), 128.3, 127.8 (2), 127.3, 50.4, 48.1, 45.2, 44.4, 42.5, 35.7, 32.9 (2), 27.2, 25.8, 25.7, 24.9; HRMS (ESI) m/z calcd for C$_{23}$H$_{31}$N$_2$O$_2$ ([M+H]$^+$), 367.2385, found 367.2387.[1,2]

11793: [α]$_D^{20}$ +24.8 (c 1.0, CHCl$_3$).

11794: [α]$_D^{20}$ −25.2 (c 0.6, CHCl$_3$); IR (neat) 2868, 1667, 1624, 1596, 1490 cm$^{-1}$; HRMS (ESI) m/z calcd for C$_{23}$H$_{25}$N$_2$O$_2$ ([M+H]$^+$), 361.1916, found 361.1911.[1,2]

11869*: [α]$_D^{20}$ −20.5 (c 1.0, CHCl$_3$); m.p. 156-158° C.; IR (neat) 2925, 1675, 1618, 1478, 1320 cm$^{-1}$; $^1$H NMR (400 MHz, CDCl$_3$) δ 11.83 (1H, bs), 7.98 (1H, d, J=2.6 Hz), 7.74 (1H, dd, J=8.7 Hz, 2.5 Hz), 7.59 (1H, d, J=8.7 Hz), 7.34-7.15 (5H, m), 5.95-5.88 (1H, m), 5.58 (1H, d, J=10.0 Hz, 1.2 Hz), 4.82 (1H, d, J=14.8 Hz), 4.45 (1H, d, J=14.8 Hz), 3.23-2.82 (5H, m), 2.52-2.45 (2H, m), 2.03-1.80 (2H, m); $^{13}$C NMR (100 MHz, CDCl$_3$) δ 172.9, 171.5, 138.5, 136.3, 135.1, 129.4, 128.7 (2), 128.1, 127.6 (2), 123.9, 119.2 (q), 50.8, 48.6, 44.3, 42.2, 36.2, 27.2, 26.6.[1,2,4]

Scheme 11

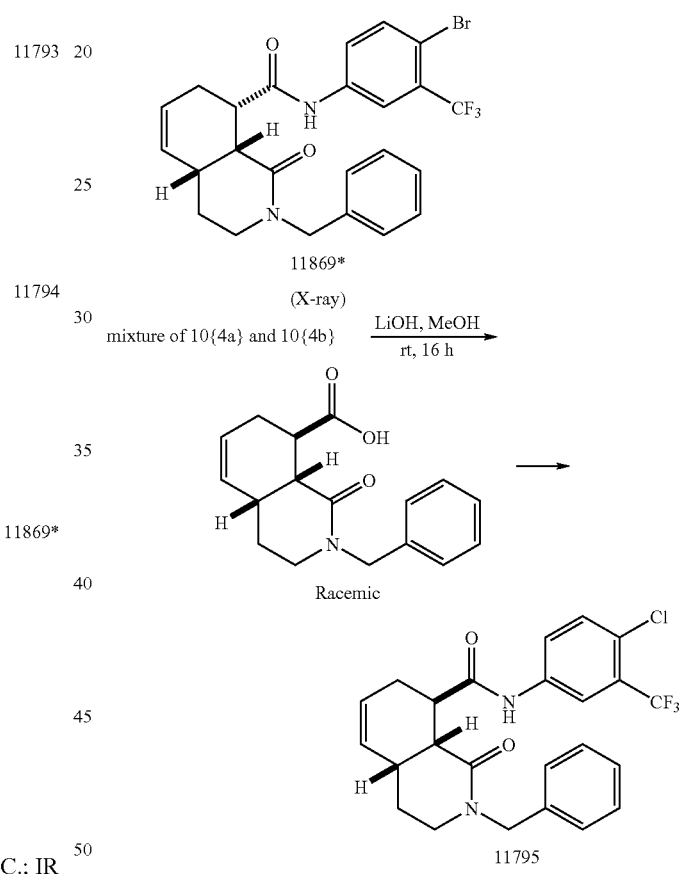

11795: m.p. 200-202° C.; IR (neat) 2931, 1694, 1612, 1540, 1482 cm$^{-1}$; $^1$H NMR (400 MHz, CDCl$_3$) δ 10.02 (1H, bs), 8.12 (1H, J=1.7 Hz), 7.68 (1H, d, J=8.6 Hz), 7.41-7.15 (6H, m), 6.10-6.00 (1H, m), 5.68 (1H, d, J=10.1 Hz), 4.66 (2H, s), 3.81-3.67 (1H, m), 3.40-1.80 (8H, m); $^{13}$C NMR (100 MHz, CDCl$_3$) δ 172.9, 170.6, 137.8, 136.5, 131.6, 128.9, 128.7 (2), 127.6, 127.5, 127.2, 127.1 (2), 123.5, 118.6 (q), 51.1, 44.7, 42.8, 41.5, 29.8, 27.0, 23.6.

For enantiomerically pure compounds:
1. 11789 and 11790 are the enantiomeric pairs of racemic 8620. 11791 and 11792 are the enantiomeric pairs of racemic 8920. 11793 and 11794 are the enantiomeric pairs of racemic 8937. Compound 11869* is a single enantiomer of racemic 11869 and has the absolute configuration shown.

2. Enantiomeric excess (ee) for 11789 and 11790 were found to be 95% and 94% respectively using analytical HPLC (Chiralcel OD-H, 1 mL/min, 10% i-PrOH/hexane).
3. The absolute configuration of 11869* was confirmed by X-Ray crystallography using anomalous dispersion. This also confirms the absolute configuration of all the carboxamides listed above.
4. The individual enantiomers can be separated from each other or combined into a racemic mixture. It is recognized that some pure enantiomers may be more biologically active compared to other enantiomers or the racemic mixture. The disclosure of one enantiomer is considered to disclose all of its other enantiomers.

The compounds prepared herein were tested for bioactivity with opioid receptors. Agonist assays: Data represent the percent efficacy (relative to cognate agonist) of the test compound at 10 micromolar. The response to a saturating concentration of a reference antagonist or to vehicle (usually none or negligible) is set to 0%. Antagonist assays: Data represent the percent inhibition of the response to an EC90 concentration (empirically determined immediately prior to assay) of cognate/reference agonist by the test compound at 10 micromolar. The response inhibition elicited by a saturating concentration of reference antagonist is set to 100%; the response inhibition (usually none or negligible) elicited by vehicle is set to 0%. The following tables provide data related to the bioactivity for opioid receptors of the compounds described herein.

TABLE 4

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 8909 | 1 | None | —CH2CH2OCH2CH2— | cyclopropyl | | | |
| 8910 | 1 | none | —CH2CH2OCH2CH2— | cyclohexyl | | 2950 | |
| 8911 | 1 | none | —CH2CH2OCH2CH2— | n-butyl | | | |
| 8912 | 1 | none | —CH2CH2N(Ph)CH2CH2— | benzyl | 3854 | 4803 | 2396 |
| 8913 | 1 | none | —CH2CH2N(Ph)CH2CH2— | cyclopropyl | | 3194 | |
| 8914 | 1 | none | —CH2CH2N(Ph)CH2CH2— | n-butyl | | | |
| 8915 | 1 | none | —CH2CH2N(Ph)CH2CH2— | 3,4-dimethoxybenzyl | 4693 | 8897 | 5536 |
| 8916 | 1 | H | —CH2CH2Ph | benzyl | | 561 | 4599 |
| 8917 | 1 | H | 2-phenylethyl | cyclopropyl | | | |
| 8918 | 1 | H | 2-phenylethyl | n-butyl | | 3271 | |
| 8919 | 1 | H | n-butyl | n-butyl | | 2813 | |
| 8920 | 1 | H | cyclohexyl | benzyl | | 298 | |
| 8921 | 1 | H | cyclohexyl | cyclopropyl | | | |
| 8922 | 1 | H | cyclohexyl | cyclohexyl | | 167 | |
| 8923 | 1 | H | cyclohexyl | n-butyl | | 1029 | |
| 8924 | 1 | H | 4-methoxybenzyl | benzyl | | 3729 | |
| 8925 | 1 | H | 4-methoxybenzyl | cyclopropyl | | | |
| 8926 | 1 | H | 4-methoxybenzyl | cyclohexyl | | 2691 | |
| 8927 | 1 | H | 4-methoxybenzyl | n-butyl | | | |
| 8928 | 1 | H | 4-methoxybenzyl | 3,4-dichlorobenzyl | | 964 | 7395 |
| 8929 | 1 | H | 4-methoxybenzyl | 3,4-dimethoxybenzyl | | | |
| 8930 | 1 | H | pyridin-3-yl-methyl | cyclopropyl | | | |
| 8931 | 1 | H | pyridin-3-yl-methyl | cyclohexyl | | 552 | |
| 8932 | 1 | H | pyridin-3-yl-methyl | 3,4-dichlorobenzyl | | 693 | |
| 8933 | 1 | H | thiazole | benzyl | | 200 | |
| 8934 | 1 | H | thiazole | cyclopropyl | | | |
| 8935 | 1 | H | thiazole | cyclohexyl | | 160 | |
| 8936 | 1 | H | thiazole | n-butyl | | 355 | |
| 8937 | 1 | H | phenyl | benzyl | 850 | 146 | 2574 |
| 8938 | 1 | H | phenyl | cyclopropyl | | 1404 | |
| 8939 | 1 | H | phenyl | cyclohexyl | 8938 | 71 | |
| 8940 | 1 | H | phenyl | n-butyl | 6109 | 677 | |
| 8941 | 1 | H | phenyl | 3,4-dichlorobenzyl | 1112 | 259 | 2697 |
| 8942 | 1 | H | phenyl | 3,4-dimethoxybenzyl | 4607 | 3058 | 3523 |
| 8943 | 1 | H | 4-methoxyphenyl | benzyl | | 883 | |
| 8944 | 1 | H | 4-methoxyphenyl | cyclopropyl | | | |
| 8945 | 1 | H | 4-methoxyphenyl | cyclohexyl | 5669 | 1790 | |
| 8946 | 1 | H | 4-methoxyphenyl | n-butyl | | 5036 | |
| 8947 | 1 | H | 4-methoxyphenyl | 3,4-dichlorobenzyl | | 2558 | 3493 |
| 8948 | 1 | H | 2,4-dichlorophenyl | cyclopropyl | | | |
| 8949 | 1 | H | 2,4-dichlorophenyl | cyclohexyl | | 506 | |
| 8950 | 1 | H | 2,4-dichlorophenyl | n-butyl | | 1139 | |
| 8951 | 1 | H | 2,4-dichlorophenyl | 3,4-dichlorobenzyl | | 2443 | |
| 8952 | 1 | H | 2,4-dichlorophenyl | 3,4-dimethoxybenzyl | | | 5660 |
| 8620 | 1 | H | 4-chloro-3-trifluoromethylphenyl | benzyl | | 5.3 (Avg) | 3,552 |

TABLE 4-continued

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 8954 | 1 | H | 4-chloro-3-trifluoromethylphenyl | cyclopropyl | | 493 | |
| 8955 | 1 | H | 4-chloro-3-trifluoromethylphenyl | cyclohexyl | | 111 | |
| 8956 | 1 | H | 4-chloro-3-trifluoromethylphenyl | n-butyl | | 190 | 2220 |
| 8957 | 1 | H | 4-chloro-3-trifluoromethylphenyl | 3,4-dichlorobenzyl | | | |
| 8958 | 1 | H | 4-chloro-3-trifluoromethylphenyl | 3,4-dimethoxybenzyl | | | 2540 |
| 5084 | 1 | H | 2-phenylethyl | 3,4-dichlorobenzyl | | 4802 | 5189 |
| 5085 | 1 | H | 3,4-difluorophenyl | 3,4-dichlorobenzyl | | 2961 | 4655 |
| 5086 | 1 | H | piperidine | 3,4-dichlorobenzyl | | | |
| 8599 | 1 | H | thiazole | 3,4-dichlorobenzyl | | | |
| 8600 | 1 | | OH | cyclopropyl | | | |
| 10821 | 1 | H | 3-chlorophenyl | phenyl | | 420 | |
| 10822 | 1 | H | 4-trifluoromethylphenyl | phenyl | | 786 | |
| 10823 | 1 | H | 3,4-difluorophenyl | phenyl | | 375 | |
| 10824 | 1 | H | 2,6-difluorophenyl | phenyl | | 5001 | |
| 10825 | 1 | H | 4-chloro-3-trifluoromethylphenyl | phenyl | | 100 | |
| 10826 | 1 | H | 2,4-dichlorophenyl | phenyl | | 287 | |
| 10827 | 1 | H | 4-methoxyphenyl | 2-phenylethyl | | | |
| 10828 | 1 | H | 3-chlorophenyl | 2-phenylethyl | | | |
| 10829 | 1 | H | 4-trifluoromethylphenyl | 2-phenylethyl | | | |
| 10830 | 1 | H | 3-trifluoromethylphenyl | 2-phenylethyl | | | |
| 10831 | 1 | H | 3,4-difluorophenyl | 2-phenylethyl | | | |
| 10832 | 1 | H | 2,6-difluorophenyl | 2-phenylethyl | | | |
| 10833 | 1 | H | 4-chloro-3-trifluoromethylphenyl | 2-phenylethyl | | | |
| 10834 | 1 | H | 2,4-dichlorophenyl | 2-phenylethyl | | 6485 | |
| 10835 | 1 | H | 4-methoxyphenyl | 4-chlorobenzyl | | 5074 | |
| 10836 | 1 | H | 3-chlorophenyl | 4-chlorobenzyl | | 225 | |
| 10837 | 1 | H | 4-trifluoromethylphenyl | 4-chlorobenzyl | | 2533 | |
| 10838 | 1 | H | 3-trifluoromethylphenyl | 4-chlorobenzyl | | 1512 | |
| 10839 | 1 | H | 3,4-difluorophenyl | 4-chlorobenzyl | | 652 | |
| 10840 | 1 | H | 2,6-difluorophenyl | 4-chlorobenzyl | | | |
| 10841 | 1 | H | 4-chloro-3-trifluoromethylphenyl | 4-chlorobenzyl | | 465 | |
| 10842 | 1 | H | 2,4-dichlorophenyl | 4-chlorobenzyl | | | |
| 10843 | 1 | H | 4-methoxyphenyl | isopropyl | | | |
| 10844 | 1 | H | 3-chlorophenyl | isopropyl | | 2131 | |
| 10845 | 1 | H | 4-trifluoromethylphenyl | isopropyl | | | |
| 10846 | 1 | H | 3-trifluoromethylphenyl | isopropyl | | 621 | |
| 10847 | 1 | H | 3,4-difluorophenyl | isopropyl | | 4197 | |
| 10848 | 1 | H | 2,6-difluorophenyl | isopropyl | | | |
| 10849 | 1 | H | 4-chloro-3-trifluoromethylphenyl | isopropyl | | 261 | |
| 10850 | 1 | H | 2,4-dichlorophenyl | isopropyl | | 2409 | |
| 10851 | 1 | H | 4-trifluoromethylphenyl | 4-trifluoromethylbenzyl | | | |
| 10852 | 1 | H | 3-trifluoromethylphenyl | 4-trifluoromethylbenzyl | | | |
| 10853 | 1 | H | 3,4-difluorophenyl | 4-trifluoromethylbenzyl | | | |
| 10854 | 1 | H | 2,6-difluorophenyl | 4-trifluoromethylbenzyl | | | |
| 11476 | 1 | H | (desoxo) phenyl | (desoxo) 3,4-dichlorobenzyl | | 1697 | 1,108 |
| 11477 | 1 | H | (desoxo) 4-chloro-3-trifluoromethylphenyl | (desoxo) benzyl | | 546 | 338 |

TABLE 4-continued

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 11478 | 1 (olefin hydrogenated) | H | 4-chloro-3-trifluoromethylphenyl | benzyl | | 51 | 1,748 |
| 11479 | 1 (olefin hydrogenated) | H | 4-chloro-3-trifluoromethylphenyl | cyclohexyl | | 792 | |
| 11789 | 1 | H | 4-chloro-3-trifluoromethylphenyl | benzyl | | 132 | 3477 |
| 11790 | 1 | H | 4-chloro-3-trifluoromethylphenyl | benzyl | | 3.2 | 208 |
| 11791 | 1 | H | cyclohexyl | benzyl | | 1303 | |
| 11792 | 1 | H | cyclohexyl | benzyl | | 213 | |
| 11793 | 1 | H | phenyl | benzyl | | 1605 | |
| 11794 | 1 | H | phenyl | benzyl | | 137 | 1657 |
| 11795 | 1 (epi scaffold) | H | 4-chloro-3-trifluoromethylphenyl | benzyl | | 158 | 5424 |
| 11808 | 1 | "=R2" | (side chain 1) | 4-chlorobenzyl | | 2293 | |
| 11809 | 1 | H | (side chain 2) | 4-chlorobenzyl | | | |
| 11810 | 1 | H | (side chain 3) | 4-chlorobenzyl | | | |
| 11811 | 1 | H | (side chain 4) | 4-chlorobenzyl | | | |
| 11812 | 1 | H | (side chain 5) | 4-chlorobenzyl | | | |
| 11813 | 1 | H | (side chain 6) | 4-chlorobenzyl | | 1157 | 1909 |
| 11814 | 1 | "=R2" | (side chain 1) | benzyl | | | |
| 11815 | 1 | H | (side chain 2) | benzyl | | | |
| 11816 | 1 | H | (side chain 3) | benzyl | | 2634 | |
| 11817 | 1 | H | (side chain 4) | benzyl | | | |
| 11818 | 1 | H | (side chain 5) | benzyl | | 6168 | |
| 11819 | 1 | H | (side chain 6) | benzyl | | 1290 | |
| 11821 | 1 | H | (side chain 2) | cyclohexyl | | 4708 | |
| 11822 | 1 | H | (side chain 3) | cyclohexyl | | 4499 | |
| 11823 | 1 | H | (side chain 4) | cyclohexyl | | | |
| 11824 | 1 | H | (side chain 5) | cyclohexyl | | | |
| 11825 | 1 | H | (side chain 6) | cyclohexyl | | 1106 | |
| 11826 | 1 | "=R2" | (side chain 1) | phenethyl | | | |
| 11827 | 1 | H | (side chain 2) | phenethyl | | | |
| 11828 | 1 | H | (side chain 3) | phenethyl | | | |
| 11829 | 1 | H | (side chain 4) | phenethyl | | | |
| 11830 | 1 | H | (side chain 5) | phenethyl | | | |
| 11831 | 1 | H | (side chain 6) | phenethyl | | 1525 | |
| 11836 | 1 | H | (±)-α-methylbenzyl | cyclohexyl | | 599 | |
| 11837 | 1 | H | 2-chloro-5-trifluoromethylphenyl | cyclohexyl | 8021 | 94 | |
| 11848 | 1 | H | (±)-α-methylbenzyl | 2-phenylethyl | | 3488 | |
| 11849 | 1 | H | 2-chloro-5-trifluoromethylphenyl | 2-phenylethyl | | 1816 | 2406 |
| 11854 | 1 | H | (±)-α-methylbenzyl | benzyl | | 712 | |
| 11856 | 1 | H | 4-chloro-3-trifluoromethylbenzyl | cyclohexyl | | 531 | |
| 11857 | 1 | H | 4-bromo-3-trifluoromethylphenyl | cyclohexyl | | 814 | |
| 11858 | 1 | H | 4-chloro-2-trifluoromethylphenyl | cyclohexyl | | 866 | |
| 11859 | 1 | H | 2-chloro-4-trifluoromethylphenyl | cyclohexyl | | | |
| 11860 | 1 | H | 4-chloro-3-methylphenyl | cyclohexyl | | 716 | |
| 11862 | 1 | H | 4-chloro-3-trifluoromethylbenzyl | phenyl | | 98 | |
| 11863 | 1 | H | 4-bromo-3-trifluoromethylphenyl | phenyl | | 12 | |
| 11864 | 1 | H | 4-chloro-2-trifluoromethylphenyl | phenyl | | 68 (Avg) | |
| 11865 | 1 | H | 2-chloro-4-trifluoromethylphenyl | phenyl | | 180 | |
| 11866 | 1 | H | 4-chloro-3-methylphenyl | phenyl | | 33.5 (Avg) | |
| 11868 | 1 | H | 4-chloro-3-trifluoromethylbenzyl | benzyl | | 455 | 2165 |

TABLE 4-continued

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 11869 | 1 | H | 4-bromo-3-trifluoromethylphenyl | benzyl | | 16.5 (Avg) | 648 |
| 11872 | 1 | H | 4-chloro-3-methylphenyl | benzyl | | 86 (Avg) | 2179 |
| 11874 | 1 | H | 4-chloro-3-trifluoromethylbenzyl | 2-phenylethyl | | 319 | 1244 |
| 11875 | 1 | H | 4-bromo-3-trifluoromethylphenyl | 2-phenylethyl | | 2283 | 1177 |
| 11876 | 1 | H | 4-chloro-3-trifluoromethylphenyl | 2-phenylethyl | | | |
| 11877 | 1 | H | 2-chloro-4-trifluoromethylphenyl | 2-phenylethyl | | 3303 | |
| 11878 | 1 | H | 4-chloro-3-methylphenyl | 2-phenylethyl | | 4116 | 1674 |
| 11886 | 1 | H | cyclohexyl | cyclohexylmethyl | | 177 | |
| 11887 | 1 | H | phenyl | cyclohexylmethyl | | 187 | |
| 11888 | 1 | H | 3-chlorophenyl | cyclohexylmethyl | | 68.0 (AVE) | |
| 11889 | 1 | H | 3,4-difluorophenyl | cyclohexylmethyl | | 131 | |
| 11890 | 1 | H | 4-chloro-3-trifluoromethylphenyl | cyclohexylmethyl | | 840 | |
| 11891 | 1 | H | thiazole | cyclohexylmethyl | | 183 | |
| 11892 | 1 | H | cyclohexyl | H | | | |
| 11893 | 1 | H | phenyl | H | | | |
| 11894 | 1 | H | 3-chlorophenyl | H | | | |
| 11895 | 1 | H | 3,4-difluorophenyl | H | | | |
| 11896 | 1 | H | 4-chloro-3-trifluoromethylphenyl | H | | 729 | |
| 11897 | 1 | H | thiazole | H | | | |
| 11899 | 1 | H | (side chain 7) | phenyl | | | |
| 11901 | 1 | H | (side chain 8) | benzyl | | | |
| 11902 | 1 | H | (side chain 7) | benzyl | | 3375 | |
| 11903 | 1 | "=R2" | (side chain 9) | benzyl | | | |
| 11904 | 1 | H | (side chain 10) | 3,4-dimethoxybenzyl | | 8766 | |
| 11905 | 1 | "=R2" | (side chain 1) | 3,4-dimethoxybenzyl | | | |
| 11908 | 1 | H | (side chain 7) | cyclohexyl | | | |
| 11909 | 1 | H | 4-fluorophenyl | benzyl | | 276 | |
| 11916 | 1 | H | methyl | cyclohexyl | | | |
| 11918 | 1 | H | benzyl | cyclohexyl | | 358 | |
| 11919 | 1 | H | 3-chloro-4-methylphenyl | cyclohexyl | | 102 | |
| 11920 | 1 | H | 4-nitro-3-trifluoromethylphenyl | cyclohexyl | | 5108 | |
| 11921 | 1 | H | 3-pyridine-yl | cyclohexyl | 836 | | |
| 11922 | 1 | H | methyl | phenyl | | | |
| 11923 | 1 | cyclohexyl | cyclohexyl | phenyl | | | |
| 11925 | 1 | H | 3-chloro-4-methylphenyl | phenyl | 15 | | |
| 11926 | 1 | H | 4-nitro-3-trifluoromethylphenyl | phenyl | 35 | | |
| 11927 | 1 | H | 3-pyridine-yl | phenyl | 2096 | | |
| 11928 | 1 | H | methyl | benzyl | | | |
| 11929 | 1 | cyclohexyl | cyclohexyl | benzyl | | | |
| 11930 | 1 | H | benzyl | benzyl | 739 | | |
| 11931 | 1 | H | 3-chloro-4-methylphenyl | benzyl | 61 | 2574 | |
| 11932 | 1 | H | 4-nitro-3-trifluoromethylphenyl | benzyl | 41 | 200 | |
| 11933 | 1 | H | 3-pyridine-yl | benzyl | 3526 | | |
| 11940 | 1 | H | adamantyl | cyclopropylmethyl | 701 | | |
| 11941 | 1 | H | 4-nitrophenyl | cyclopropylmethyl | | | |
| 11942 | 1 | H | 4-iodophenyl | cyclopropylmethyl | 1276 | | |
| 11943 | 1 | H | 3-bromobenzyl | cyclopropylmethyl | | | |
| 11944 | 1 | H | 4-methylbenzyl | cyclopropylmethyl | | | |
| 11945 | 1 | H | 2,4,6-trimethylphenyl | cyclopropylmethyl | >10,000 | | |
| 11946 | 1 | H | adamantyl | phenyl | 116 | | |
| 11947 | 1 | H | 4-nitrophenyl | phenyl | 141 | | |
| 11948 | 1 | H | 4-iodophenyl | phenyl | 83 | | |
| 11949 | 1 | H | 3-bromobenzyl | phenyl | 302 | | |
| 11950 | 1 | H | 4-methylbenzyl | phenyl | 297 | | |
| 11951 | 1 | H | 2,4,6-trimethylphenyl | phenyl | 4300 | | |
| 11952 | 1 | H | adamantyl | benzyl | | | |
| 11953 | 1 | H | 4-nitrophenyl | benzyl | | | |
| 11954 | 1 | H | 4-iodophenyl | benzyl | 194 | 2825 | |
| 11955 | 1 | H | 3-bromobenzyl | benzyl | 438 | 3275 | |
| 11956 | 1 | H | 4-methylbenzyl | benzyl | 2362 | | |
| 11957 | 1 | H | 2,4,6-trimethylphenyl | benzyl | 3216 | | |
| 12084 | 1 | "=R2" | —CH2CH2CH2CH2— | cyclohexyl | 6292 | | |

TABLE 4-continued

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 12085 | 1 | H | cyclopropylmethyl | cyclohexyl | 475 | | |
| 12086 | 1 | methyl | methyl | cyclohexyl | >10,000 | | |
| 12087 | 1 | H | 4-chlorophenyl | cyclohexyl | 582 | | |
| 12088 | 1 | H | 3,4,5-trifluorophenyl | cyclohexyl | 2793 | | |
| 12089 | 1 | "=R2" | —CH2CH2CH2CH2— | cyclopropylmethyl | | | |
| 12090 | 1 | H | cyclopropylmethyl | cyclopropylmethyl | 5650 | | |
| 12091 | 1 | methyl | methyl | cyclopropylmethyl | | | |
| 12092 | 1 | H | 4-chlorophenyl | cyclopropylmethyl | 3234 | | |
| 12093 | 1 | H | 3,4,5-trifluorophenyl | cyclopropylmethyl | 4370 | | |
| 12094 | 1 | "=R2" | —CH2CH2CH2CH2— | phenyl | >10,000 | | |
| 12095 | 1 | H | cyclopropylmethyl | phenyl | 1225 | | |
| 12096 | 1 | methyl | methyl | phenyl | >10,000 | | |
| 12097 | 1 | H | 4-chlorophenyl | phenyl | 168 | | |
| 12098 | 1 | H | 3,4,5-trifluorophenyl | phenyl | 289 | | |
| 12099 | 1 | "=R2" | —CH2CH2CH2CH2— | benzyl | 6647 | | |
| 12100 | 1 | H | cyclopropylmethyl | benzyl | 539 | | |
| 12101 | 1 | methyl | methyl | benzyl | >10,000 | | |
| 12102 | 1 | H | 4-chlorophenyl | benzyl | 165 | 5029 | |
| 12103 | 1 | H | 3,4,5-trifluorophenyl | benzyl | 180 | | |
| 12110 | 1 | H | allyl | cyclohexylmethyl | 1428 | | |
| 12111 | 1 | H | anthranilamide | cyclohexylmethyl | | | |
| 12112 | 1 | H | 4-(ethyl carboxylate)phenyl | cyclohexylmethyl | | | |
| 12113 | 1 | methyl | phenyl | cyclohexylmethyl | 2830 | | |
| 12114 | 1 | H | 3,4-dimethoxybenzyl | cyclohexylmethyl | | | |
| 12115 | 1 | "=R2" | ethyl pipecolinate | cyclohexylmethyl | 9155 | | |
| 12116 | 1 | H | allyl | phenyl | | | |
| 12117 | 1 | H | anthranilamide | phenyl | 648 | | |
| 12118 | 1 | H | 4-(ethyl carboxylate)phenyl | phenyl | | | |
| 12119 | 1 | methyl | phenyl | phenyl | 4014 | | |
| 12120 | 1 | H | 3,4-dimethoxybenzyl | phenyl | | | |
| 12121 | 1 | H | ethyl pipecolinate | phenyl | | | |
| 12122 | 1 | H | allyl | benzyl | 3431 | | |
| 12123 | 1 | H | anthranilamide | benzyl | 5932 | | |
| 12124 | 1 | H | 4-(ethyl carboxylate)phenyl | benzyl | 7821 | | |
| 12125 | 1 | H | phenyl | benzyl | >10,000 | | |
| 12126 | 1 | H | 3,4-dimethoxybenzyl | benzyl | >10,000 | | |
| 12127 | 1 | "=R2" | ethyl pipecolinate | benzyl | >10,000 | | |
| 12134 | 1 | isopropyl | cyclohexyl | cyclohexylmethyl | 1634 | | |
| 12135 | 1 | "=R2" | —CH2CH2(NMe)CH2CH2— | cyclohexylmethyl | | | |
| 12136 | 1 | H | 3,4-dichlorobenzyl | cyclohexylmethyl | 1301 | | |
| 12137 | 1 | H | 4-hexylphenyl | cyclohexylmethyl | | | |
| 12138 | 1 | H | pyrazine-2-yl | cyclohexylmethyl | 1651 | | |
| 12140 | 1 | isopropyl | cyclohexyl | phenyl | 416 | | |
| 12141 | 1 | "=R2" | —CH2CH2(NMe)CH2CH2— | phenyl | | | |
| 12142 | 1 | H | 3,4-dichlorobenzyl | phenyl | 103 | | |
| 12143 | 1 | H | 4-hexylphenyl | phenyl | | | |
| 12144 | 1 | H | pyrazine-2-yl | phenyl | | | |
| 12147 | 1 | "=R2" | —CH2CH2(NMe)CH2CH2— | benzyl | | | |
| 12148 | 1 | H | 3,4-dichlorobenzyl | benzyl | 644 | 2779 | |
| 12149 | 1 | H | 4-hexylphenyl | benzyl | | | |
| 12150 | 1 | H | pyrazine-2-yl | benzyl | | | |
| 12152 | 1 | H | cyclohexyl | cyclopropylmethyl | 2518 | | |
| 12153 | 1 | H | phenyl | cyclopropylmethyl | 6624 | | |
| 12154 | 1 | H | 3-chlorophenyl | cyclopropylmethyl | 1177 | | |
| 12155 | 1 | H | 3,4-difluorophenyl | cyclopropylmethyl | 2252 | | |
| 12156 | 1 | H | 4-chloro-3-trifluoromethylphenyl | cyclopropylmethyl | 788 | | |
| 12157 | 1 | H | thiazole | cyclopropylmethyl | 3501 | | |
| 12160 | 1 | methyl | phenyl | cyclohexyl | 2978 | | |
| 12161 | 1 | H | 4-chloro-3-trifluoromethylphenyl | (4'-methoxybiphenyl-3-yl)methyl | 2126 | | |
| 12163 | 1 | H | cyclohexyl | (±)-α-methylbenzyl | 1162 | 5909 | |
| 12164 | 1 | H | phenyl | (±)-α-methylbenzyl | 1384 | 4775 | |
| 12165 | 1 | H | 3-chlorophenyl | (±)-α-methylbenzyl | 1207 | | |
| 12166 | 1 | H | 3,4-difluorophenyl | (±)-α-methylbenzyl | 3203 | | |
| 12168 | 1 | H | thiazole | (±)-α-methylbenzyl | 1450 | | |

TABLE 4-continued

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 12170 | 1 | H | 4-chloro-3-trifluoromethylphenyl | 3-bromobenzyl | 1718 | 1462 | |
| 12171 | 1 | H | 4-bromo-3-trifluoromethylphenyl | 3-bromobenzyl | 503 | 694 | |
| 12172 | 1 | H | 4-bromo-3-trifluoromethylphenyl | cyclopropylmethyl | 1282 | | |
| 12173 | 1 | H | 4-bromo-3-trifluoromethylphenyl | cyclohexylmethyl | 508 | | |
| 13474 | 1 | H | 4-fluoro-3-trifluoromethylphenyl | benzyl | 192 | | |
| 13475 | 1 | H | 4-methyl-3-trifluoromethylphenyl | benzyl | 39 | 1163 | |
| 13476 | 1 | H | 2,3-difluoro-4-methylphenyl | benzyl | 559 | | |
| 13478 | 1 | H | 4-bromo-3-trifluoromethylphenyl | 2-fluorobenzyl | 22 | 299 | |
| 13479 | 1 | H | 4-methyl-3-trifluoromethylphenyl | 2-fluorobenzyl | 9.5 | 763 | |
| 13480 | 1 | H | 4-bromo-3-trifluoromethylphenyl | 2-methoxybenzyl | | | |
| 13481 | 1 | H | 4-methyl-3-trifluoromethylphenyl | 2-methoxybenzyl | 1342 | 1898 | |
| 13482 | 1 | H | 4-chloro-3-trifluoromethylphenyl | 2-fluoro-6-methoxybenzyl | | | |
| 13483 | 1 | H | 4-bromo-3-trifluoromethylphenyl | 2-fluoro-6-methoxybenzyl | | | |
| 13484 | 1 | H | 4-methyl-3-trifluoromethylphenyl | 2-fluoro-6-methoxybenzyl | | | |
| 13485 | 1 | H | 2,3-difluoro-4-methylphenyl | 2-fluoro-6-methoxybenzyl | | 5122 | |
| 14309 | 1 | H | pentafluorophenyl | benzyl | | 2969 | |
| 14417 | 2 | H | phenyl | benzyl | | | |
| 14418 | 2 | H | cyclohexyl | benzyl | | | |
| 14419 | 2 | H | 3-chlorophenyl | benzyl | | | |
| 14420 | 2 | H | 4-bromo-3-trifluoromethylphenyl | benzyl | | | |
| 14421 | 2 | H | 4-chloro-3-trifluoromethylphenyl | benzyl | | | |
| 14422 | 2 | H | thiazole | benzyl | | | |
| 14423 | 2 | H | phenyl | cyclohexyl | 8836 | | |
| 14424 | 2 | H | cyclohexyl | cyclohexyl | 1690 | | |
| 14425 | 2 | H | 3-chlorophenyl | cyclohexyl | 6044 | | |
| 14426 | 2 | H | 4-bromo-3-trifluoromethylphenyl | cyclohexyl | | | |
| 14427 | 2 | H | 4-chloro-3-trifluoromethylphenyl | cyclohexyl | | | |
| 14428 | 2 | H | thiazole | cyclohexyl | 2990 | | |
| 14429 | 0 | H | phenyl | benzyl | 7019 | | |
| 14430 | 0 | H | cyclohexyl | benzyl | | | |
| 14431 | 0 | H | 3-chlorophenyl | benzyl | | | |
| 14432 | 0 | H | 4-bromo-3-trifluoromethylphenyl | benzyl | 2767 | | |
| 14433 | 0 | H | 4-chloro-3-trifluoromethylphenyl | benzyl | 1938 | | |
| 14434 | 0 | H | thiazole | benzyl | | | |
| 14435 | 0 | H | phenyl | cyclohexyl | 1608 | | |
| 14436 | 0 | H | cyclohexyl | cyclohexyl | 2150 | | |
| 14437 | 0 | H | 3-chlorophenyl | cyclohexyl | 962 | | |
| 14438 | 0 | H | 4-bromo-3-trifluoromethylphenyl | cyclohexyl | 1918 | | |
| 14439 | 0 | H | 4-chloro-3-trifluoromethylphenyl | cyclohexyl | 5348 | | |
| 14440 | 0 | H | thiazole | cyclohexyl | 1038 | | |
| 14827 | 1 | methyl | methoxy | 2-phenylethyl | | | |
| 14828 | 1 | H | biphenyl-2-yl | phenyl | | | |
| 14829 | 1 | H | biphenyl-2-yl | benzyl | | | |
| 14830 | 1 | H | phenyl | (4'-methylbiphenyl-3-yl)methyl | | | |
| 14832 | 1 | H | 4-chloro-3-trifluoromethylphenyl | (4'-methylbiphenyl-3-yl)methyl | | | |

TABLE 4-continued

Opioid secondary binding activity for Formula 10 analogs

| C# | n= | R1 | R2 | R3 | DOR, Ki (nM) | KOR, Ki (nM) | MOR, Ki (nM) |
|---|---|---|---|---|---|---|---|
| 14833 | 1 | H | 4-chloro-3-trifluoromethylphenyl | (4'-trifluoromethoxybiphenyl-3-yl)methyl | | | |
| 14834 | 1 | H | phenyl | (side chain 11) | | | |
| 14835 | 1 | H | phenyl | (side chain 12) | | | |
| 14836 | 1 | H | phenyl | (side chain 13) | | | |
| 14837 | 1 | H | (4'-methylbiphenyl-3-yl)methyl | phenyl | | | |
| 14838 | 1 | H | (4'-methylbiphenyl-3-yl)methyl | benzyl | | | |
| 14839 | 1 | H | (4'-carbamoylbiphenyl-3-yl)methyl | benzyl | | | |
| 14840 | 1 | H | (side chain 16) | benzyl | | | |
| 14841 | 1 | H | (side chain 11) | benzyl | | | |
| 14842 | 1 | H | (side chain 15) | benzyl | | | |
| 14843 | 1 | H | (side chain 14) | benzyl | | | |
| 14844 | 1 | H | 3-(thiophen-2-yl)benzyl | benzyl | | | |
| 14845 | 1 | H | (side chain 13) | benzyl | | | |

(oh = olefin hydrogenated) (epi = epi scaffold or unknown epimer) (when R1 is nothing, then R2 is a ring) (Value for C# 8620 is an average)

TABLE 5

Example compounds with KOR/MOR binding data.

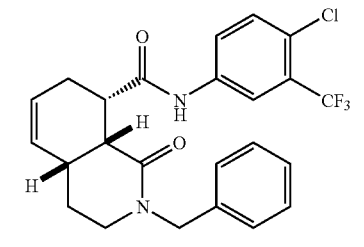

KOR 3.2 nM
MOR 208 nM
enantiopure

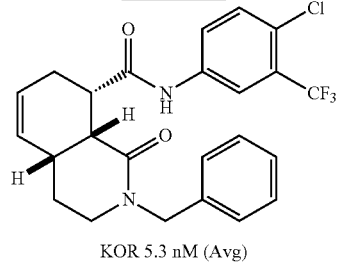

KOR 5.3 nM (Avg)
MOR 3,552 nM

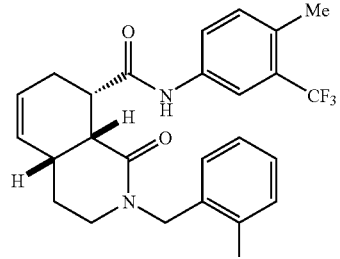

KOR 9.5 nM
MOR 763 nM

TABLE 5-continued

Example compounds with KOR/MOR binding data.

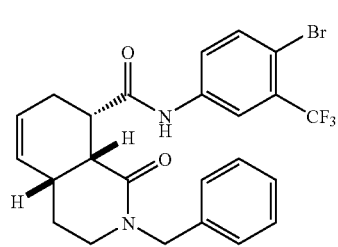

KOR 17 nM (Avg)
MOR 648 nM

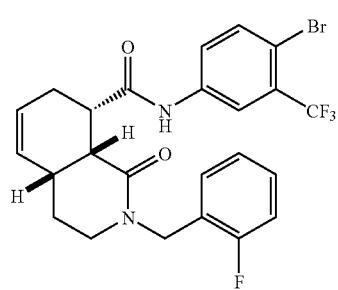

KOR 22 nM
MOR 299 nM

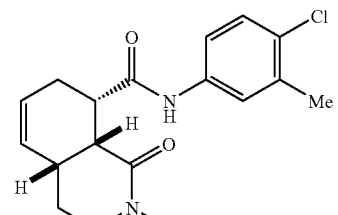

KOR 34 nM (Avg)

TABLE 5-continued
Example compounds with KOR/MOR binding data.
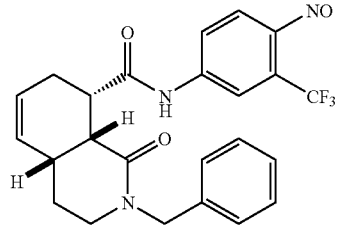
KOR 41 nM
MOR 200 nM
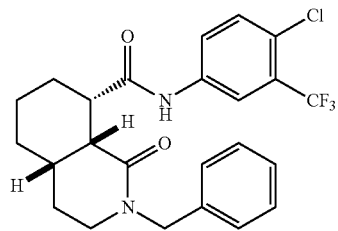
KOR 51 nM
MOR 1,708 nM
hydrogenated
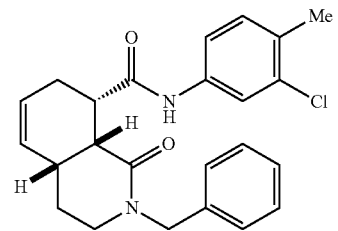
KOR 61 nM
MOR 2,574 nM
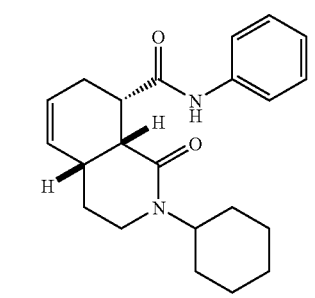
KOR 71 nM
DOR 8.938 nM
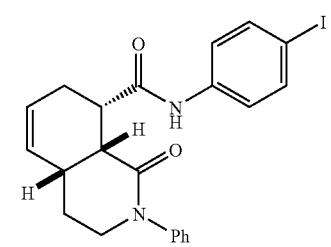
KOR 83 nM
TABLE 5-continued
Example compounds with KOR/MOR binding data.
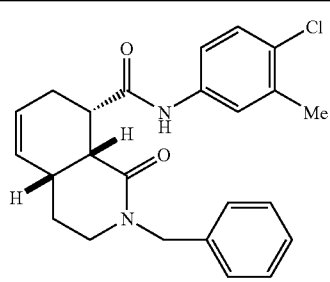
KOR 86 nM
MOR 2.179 nM
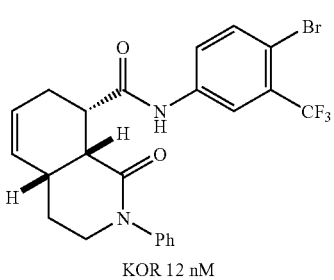 [SMILES: O=C(Nc1ccc(Br)c(C(F)(F)F)c1)[C@H]1CC=C[C@H]2CCN(c3ccccc3)C(=O)[C@@H]12]
KOR 12 nM
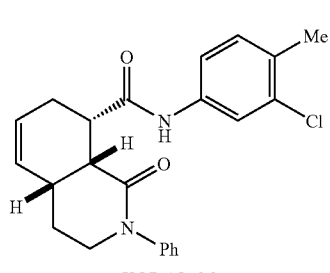
KOR 15 nM
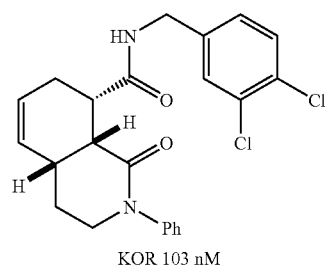 [SMILES: O=C(NCc1ccc(Cl)c(Cl)c1)[C@H]1CC=C[C@H]2CCN(c3ccccc3)C(=O)[C@@H]12]
KOR 103 nM
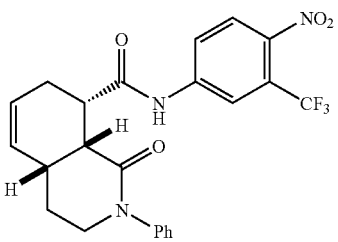
KOR 35 nM TABLE 5-continued Example compounds with KOR/MOR binding data.

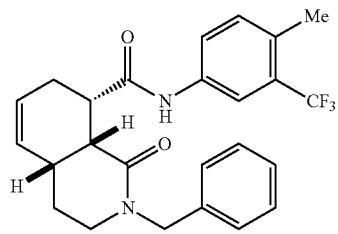

KOR 39 nM
MOR 1,163 nM

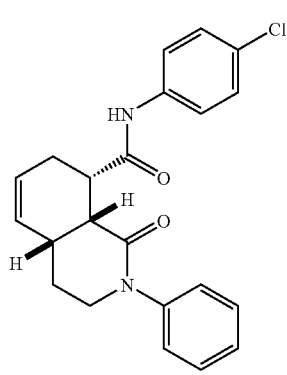

KOR 168 nM

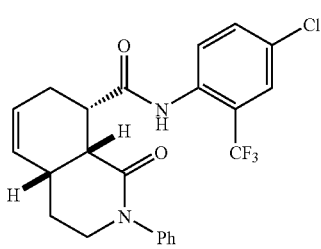

KOR 68 nM (Avg)

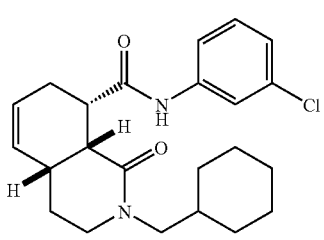

KOR 68 nM (Avg)

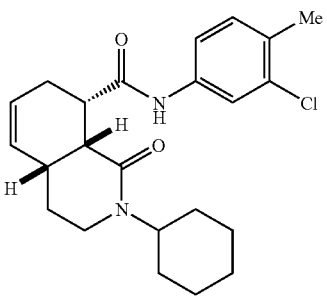

KOR 102 nM

TABLE 5-continued

Example compounds with KOR/MOR binding data.

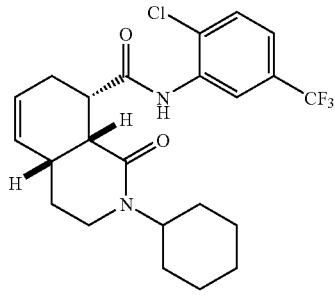 [SMILES: O=C(Nc1cc(C(F)(F)F)ccc1Cl)[C@H]1CC=C[C@H]2CCN(C3CCCCC3)C(=O)[C@@H]12]

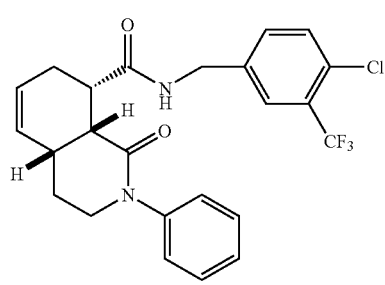 [SMILES: O=C(NCc1ccc(Cl)c(C(F)(F)F)c1)[C@H]1CC=C[C@H]2CCN(c3ccccc3)C(=O)[C@@H]12]

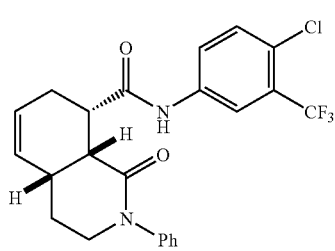 [SMILES: O=C(Nc1ccc(Cl)c(C(F)(F)F)c1)[C@H]1CC=C[C@H]2CCN(c3ccccc3)C(=O)[C@@H]12]

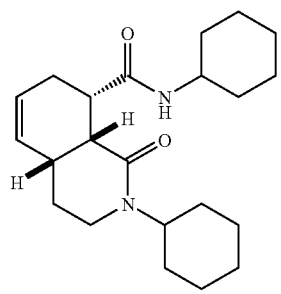

KOR 167 nM

Table 6 provides data that represent the average percent efficacy (N=4; relative to cognate agonist) of the test compound at 10 micromolar concentration. The response to a saturating concentration of cognate/reference agonist is set to 100%; the response to a saturating concentration of a reference antagonist or to vehicle (usually none or negligible) is set to 0%. All functional assays are performed on stably transfected CHO-cell lines expressing hKOR, hMOR or hDOR.

Experimental Procedure and Data Analysis: Assay buffer: 50 mM HEPES, 5 mM MgCl2, 150 mM NaCl, 0.2 mM EDTA, 100 mg/l ascorbic acid, pH 7.4 Reference agonist (U69593 for KOR; DAMGO for MOR and DADL for DOR) and compounds to be tested are dissolved in assay buffer or DMSO according to solubility. Serial dilutions of the test and reference compounds are made in binding buffer at 2× assay concentration (final assay concentrations ranging from 0.1 nM to 10 μM). Crude membrane fractions (1.8 to 3.5 cm2/well) (prepared from 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80 degrees centigrade; typically, one 10-cm plate provides sufficient material for 24 wells) are resuspended in 1.2 ml of assay buffer containing 20 μM GDP, wheat germ agglutinin (WGA)-coated scintillation proximity beads (2.4 mg), and [35S]GTPγS (300 pM final). The suspension is then added (50 μl/well) to 50 μl of the 2× test or reference compounds (each concentration assayed in triplicate) in flexible transparent PET 96-well plates. The reaction plate is sealed and incubated for 90 min at room temperature, then centrifuged for 5 min at 216×g, and finally loaded into a Wallac MicroBeta TriLux counter. Non-specific [35S]GTPγS binding is assessed at the maximum concentration of reference agonist in the presence of 10 μM antagonist. The background signal is measured at 10 μM reference agonist in the presence of 10 μM unlabeled GTPγS. Raw data (dpm) representing total [35S]GTPγS binding (i.e., specific+non-specific binding) are calculated as a percentage of the maximum response by the reference agonist (in this case U69593).

TABLE 6

Compounds having KOR agonist activity.

| C# | KOR agonist |
|---|---|
| 8909 | 7.8 |
| 8910 | 42.7 |
| 8911 | 8.3 |
| 8912 | 8 |
| 8913 | 27.5 |
| 8914 | 9.9 |
| 8915 | 6.7 |
| 8916 | 110.6 |
| 8917 | 6.6 |
| 8918 | 12.6 |
| 8919 | 40.3 |
| 8920 | 94.2 |
| 8921 | 4.1 |
| 8922 | 8 |
| 8923 | 67.6 |
| 8924 | 18.8 |
| 8925 | 5.4 |
| 8926 | 29 |
| 8927 | 8.7 |
| 8928 | 17.7 |
| 8929 | 3.6 |
| 8930 | 4 |
| 8931 | 67.7 |
| 8932 | 74.6 |
| 8933 | 121.5 |
| 8934 | 11 |
| 8935 | 129.2 |
| 8936 | 93.8 |
| 8937 | 136.6 |
| 8938 | 21.8 |
| 8939 | 133.7 |
| 8940 | 112.1 |
| 8941 | 79 |
| 8942 | 5.4 |
| 8943 | 72.9 |
| 8944 | 1 |
| 8945 | 54.3 |
| 8946 | 23.5 |
| 8947 | 17.3 |
| 8948 | 29.6 |
| 8949 | 67.9 |
| 8950 | 72.9 |
| 8951 | 23.2 |
| 8952 | −2.6 |
| 8953 | |
| 8954 | 66.4 |

TABLE 6-continued

Compounds having KOR agonist activity.

| C# | KOR agonist |
|---|---|
| 8955 | 93.2 |
| 8956 | 118.7 |
| 8957 | 33.1 |

Table 7 shows compounds having KOR agonist activity.

Experimental Procedure and Data Analysis: Assay buffer: 50 mM HEPES, 5 mM MgCl2, 150 mM NaCl, 0.2 mM EDTA, 100 mg/l ascorbic acid, pH 7.4 Reference agonist (U69593 for KOR; DAMGO for MOR and DADL for DOR) and compounds to be tested are dissolved in assay buffer or DMSO according to solubility. Serial dilutions of the test and reference compounds are made in binding buffer at 2× assay concentration (final assay concentrations ranging from 0.1 nM to 10 μM). Crude membrane fractions (1.8 to 3.5 cm2/well) (prepared from 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80 degrees centigrade; typically, one 10-cm plate provides sufficient material for 24 wells) are resuspended in 1.2 ml of assay buffer containing 20 μM GDP, wheat germ agglutinin (WGA)-coated scintillation proximity beads (2.4 mg), and [35S]GTPγS (300 pM final). The suspension is then added (50 μl/well) to 50 μl of the 2× test or reference compounds (each concentration assayed in triplicate) in flexible transparent PET 96-well plates. The reaction plate is sealed and incubated for 90 min at room temperature, then centrifuged for 5 min at 216×g, and finally loaded into a Wallac MicroBeta TriLux counter. Non-specific [35S]GTPγS binding is assessed at the maximum concentration of reference agonist in the presence of 10 μM antagonist. The background signal is measured at 10 μM reference agonist in the presence of 10 μM unlabeled GTPγS.

Raw data (dpm) representing total [35S]GTPγS binding (i.e., specific+non-specific binding) are plotted as a function of the logarithm of the molar concentration of the drug (i.e., test or reference compound). Non-linear regression of the normalized (i.e., fold increase in [35S]GTPγS binding over that observed in the absence of test or reference compound) data is performed in Prism 4.0 (GraphPad Software) using the built-in three parameter logistic model (i.e., sigmoidal concentration-response) describing agonist-stimulated activation of one receptor population:

$$y = \text{bottom} + [(\text{top} - \text{bottom})/(1 + 10^{x - \log EC50})]$$

where bottom equals the best-fit basal [35S]GTPγS binding and top equals the best-fit maximum [35S]GTPγS binding. The log EC50 (i.e., the log of the drug concentration that increases [35S]GTPγS binding by 50% of the top) is thus estimated from the data, and the EC50 (agonist potency) is obtained. To obtain an estimate of the relative efficacy of the test compound (Rel. Emax), its data-fit top is compared to and expressed as a ratio of that for the reference agonist (Rel. Emax of 1.00). Reference antagonist for KOR was nor-BNI; for DOR was naltrindole and for MOR was naloxone.

TABLE 7

Compounds having KOR agonist activity, with values shown as ic50's (uM).

| C# | KOR agonist EC$_{50}$ values | Emax values relative to U69593 |
|---|---|---|
| 8620 | 4.7 | 67% |
| 10825 | 26 | 82% |
| 11790 | 12 | 78% |
| 11834 | 839 | 71% |
| 11837 | 419 | 106% |
| 11862 | 238 | 81% |
| 11863 | 10 | 95% |
| 11864 | 503 | 119% |
| 11866 | 417 | 123% |
| 11869 | 158 | 68% |
| 11872 | 1,431.00 | 123% |
| 11888 | 868 | 70% |

TABLE 8

Example ester compounds with KOR/MOR binding data, where Ki is for the KOR.

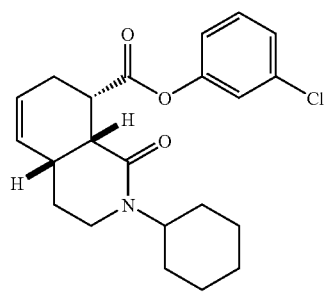

Ki = 84 nM

Ki = 241 nM

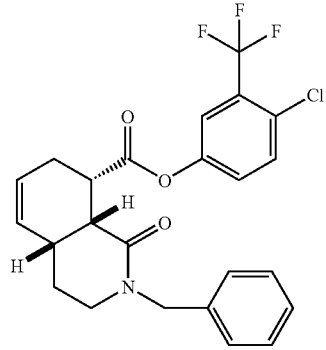

Ki = 244 nM

TABLE 8-continued

Example ester compounds with KOR/MOR binding data, where Ki is for the KOR.

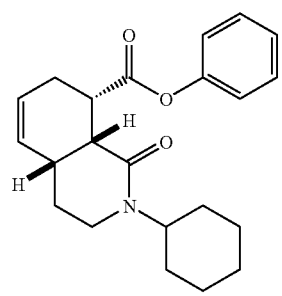

Ki = 405 nM

Ki = 713 nM

Ki = 1,478 nM

Ki = 1,874 nM

Ki = 1,971 nM
MOR: Ki = 1,501 nM

TABLE 8-continued
Example ester compounds with KOR/MOR binding data, where Ki is for the KOR.
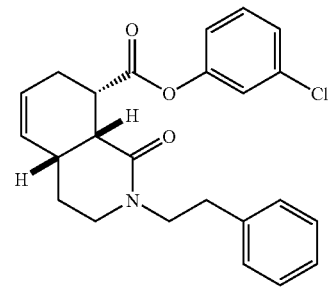
Ki = 3.222 nM
MOR: Ki = 1.771 nM
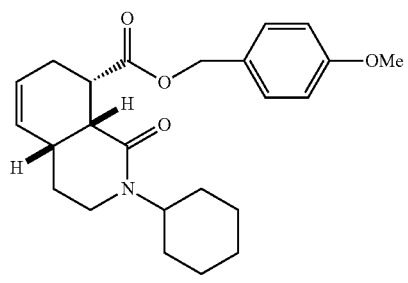
Ki = 3,363 nM
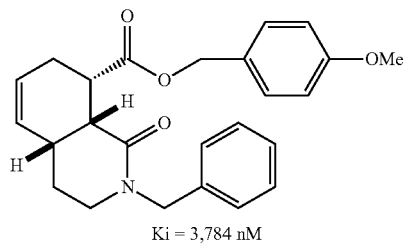 [SMILES: COc1ccc(COC(=O)[C@H]2CC=C[C@H]3CCN(Cc4ccccc4)C(=O)[C@@H]23)cc1]
Ki = 3,784 nM
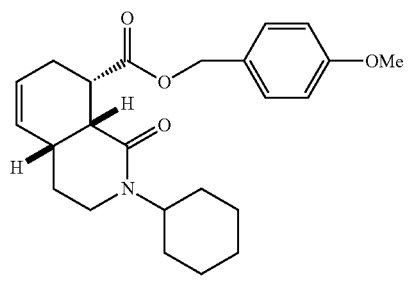
Ki = 3,790 nM
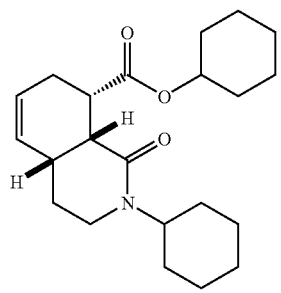
Ki = 508 nM
TABLE 8-continued
Example ester compounds with KOR/MOR binding data, where Ki is for the KOR.
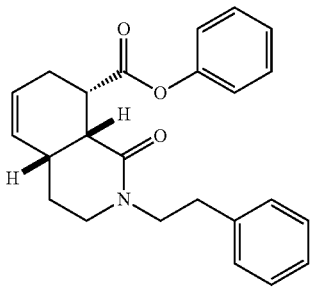
Ki = 2,859 nM
MOR: Ki = 649 nM
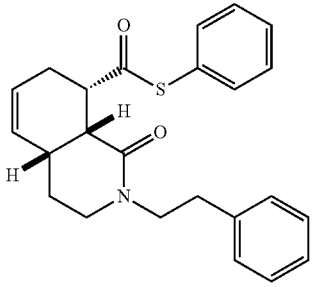
Ki = 2,616 nM
TABLE 9
Example lactone compounds with KOR binding data
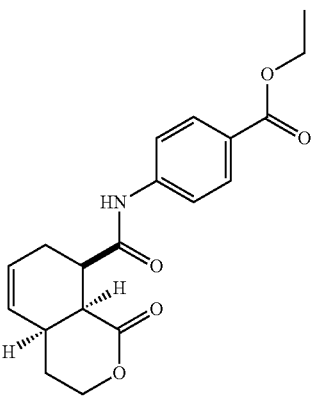
Ki = 8,996 nM TABLE 9-continued
Example lactone compounds with KOR binding data
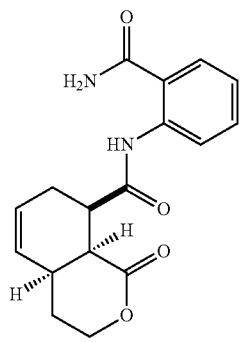
Ki = 6,006 nM
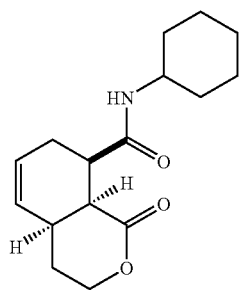 [SMILES: O=C1OCC[C@H]2C=CC[C@@H](C(=O)NC3CCCCC3)[C@@H]12]
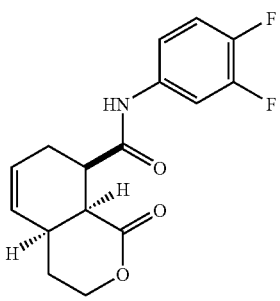 [SMILES: O=C1OCC[C@H]2C=CC[C@@H](C(=O)Nc3ccc(F)c(F)c3)[C@@H]12]
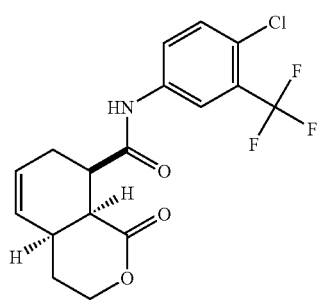 [SMILES: O=C1OCC[C@H]2C=CC[C@@H](C(=O)Nc3ccc(Cl)c(C(F)(F)F)c3)[C@@H]12]
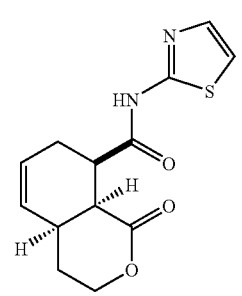 [SMILES: O=C1OCC[C@H]2C=CC[C@@H](C(=O)Nc3nccs3)[C@@H]12]
TABLE 9-continued
Example lactone compounds with KOR binding data
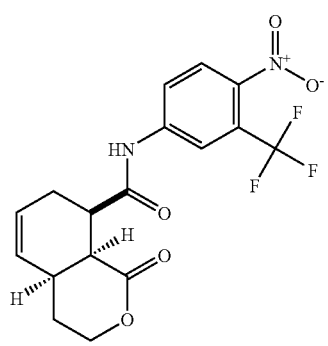 [SMILES: O=C1OCC[C@H]2C=CC[C@@H](C(=O)Nc3ccc([N+](=O)[O-])c(C(F)(F)F)c3)[C@@H]12]
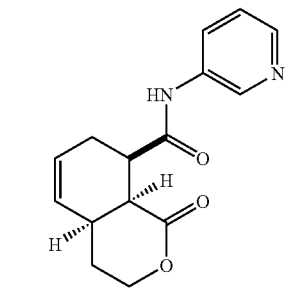 [SMILES: O=C1OCC[C@H]2C=CC[C@@H](C(=O)Nc3cccnc3)[C@@H]12]
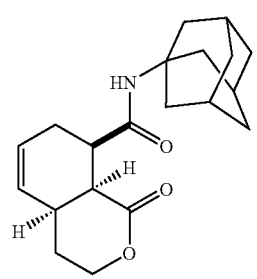 [SMILES: O=C1OCC[C@H]2C=CC[C@@H](C(=O)NC34CC5CC(CC(C5)C3)C4)[C@@H]12]
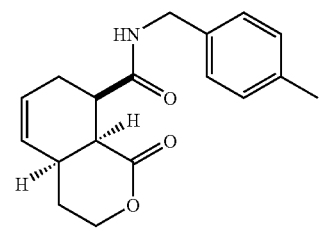 [SMILES: Cc1ccc(CNC(=O)[C@@H]2CC=C[C@@H]3CCOC(=O)[C@@H]32)cc1]
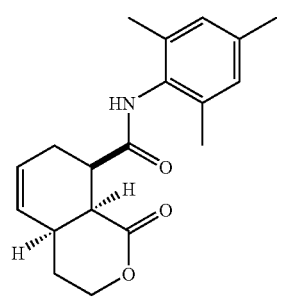 [SMILES: Cc1cc(C)c(NC(=O)[C@@H]2CC=C[C@@H]3CCOC(=O)[C@@H]32)c(C)c1]

TABLE 9-continued
Example lactone compounds with KOR binding data
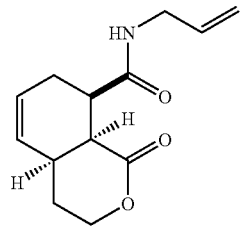 [SMILES: C=CCNC(=O)[C@@H]1CC=C[C@@H]2CCOC(=O)[C@@H]21]
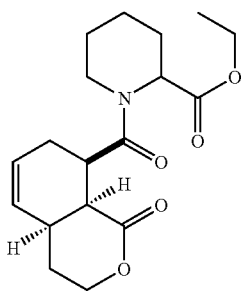 [SMILES: CCOC(=O)C1CCCCN1C(=O)[C@@H]1CC=C[C@@H]2CCOC(=O)[C@@H]21]
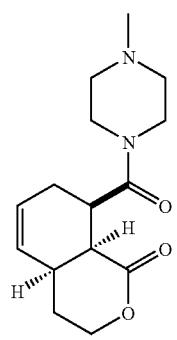
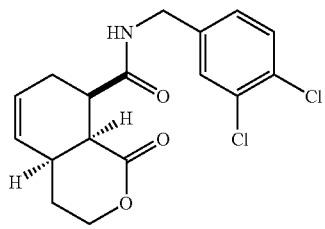 [SMILES: O=C1OCC[C@H]2C=CC[C@@H](C(=O)NCc3ccc(Cl)c(Cl)c3)[C@@H]12]
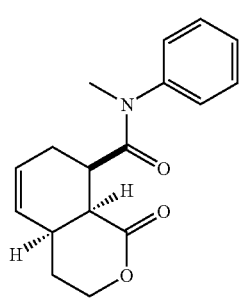
TABLE 9-continued
Example lactone compounds with KOR binding data
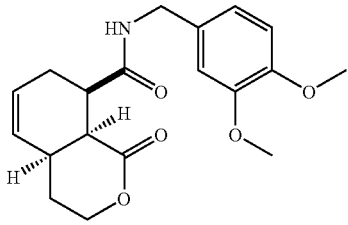 [SMILES: COc1ccc(CNC(=O)[C@@H]2CC=C[C@@H]3CCOC(=O)[C@@H]32)cc1OC]
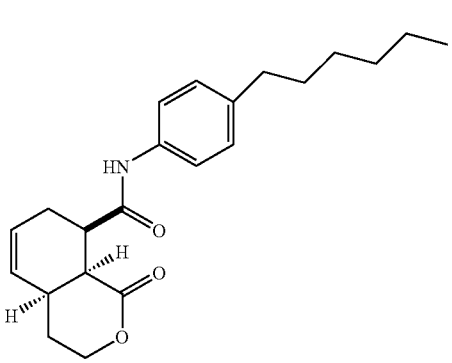 [SMILES: CCCCCCc1ccc(NC(=O)[C@@H]2CC=C[C@@H]3CCOC(=O)[C@@H]32)cc1]
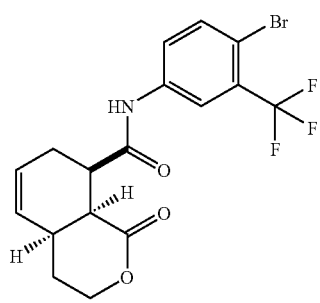 [SMILES: O=C1OCC[C@H]2C=CC[C@@H](C(=O)Nc3ccc(Br)c(C(F)(F)F)c3)[C@@H]12]
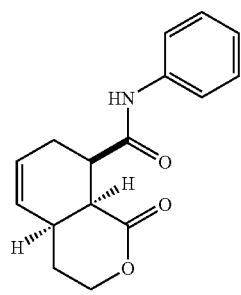 [SMILES: O=C1OCC[C@H]2C=CC[C@@H](C(=O)Nc3ccccc3)[C@@H]12]
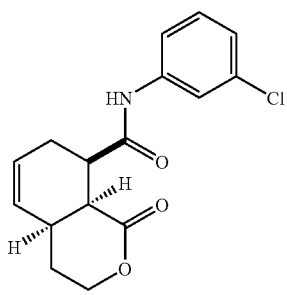 [SMILES: O=C1OCC[C@H]2C=CC[C@@H](C(=O)Nc3cccc(Cl)c3)[C@@H]12]

TABLE 9-continued

Example lactone compounds with KOR binding data

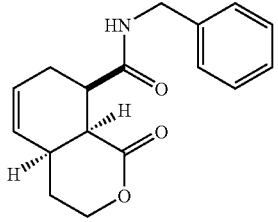 [SMILES: O=C1OCC[C@H]2C=CC[C@@H](C(=O)NCc3ccccc3)[C@@H]12]

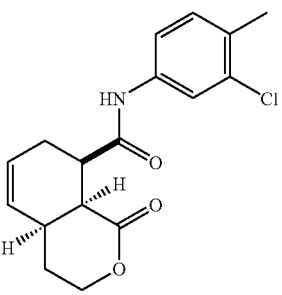 [SMILES: Cc1ccc(NC(=O)[C@@H]2CC=C[C@@H]3CCOC(=O)[C@@H]32)cc1Cl]

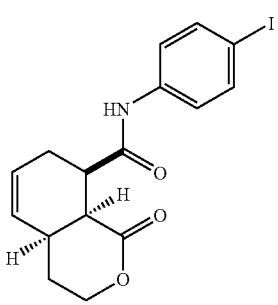 [SMILES: O=C1OCC[C@H]2C=CC[C@@H](C(=O)Nc3ccc(I)cc3)[C@@H]12]

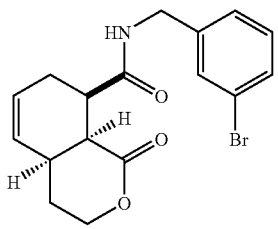 [SMILES: O=C1OCC[C@H]2C=CC[C@@H](C(=O)NCc3cccc(Br)c3)[C@@H]12]

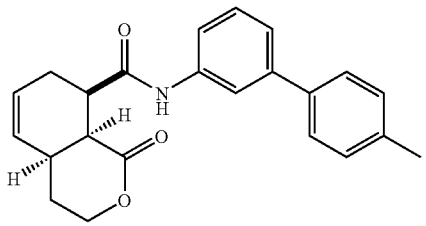 [SMILES: Cc1ccc(-c2cccc(NC(=O)[C@@H]3CC=C[C@@H]4CCOC(=O)[C@@H]43)c2)cc1]

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

The invention claimed is:

1. A compound selected from the group of:

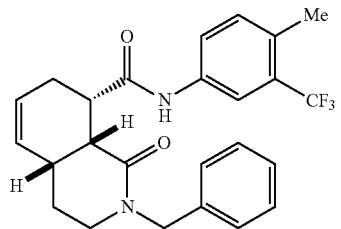

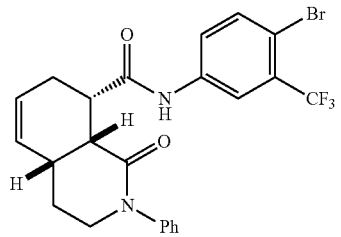

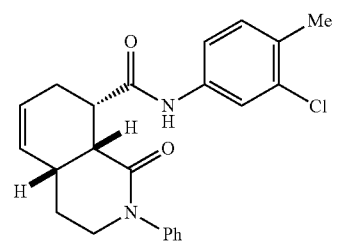

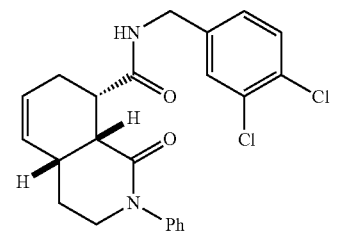

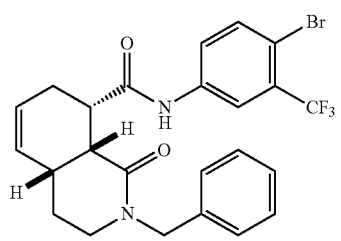

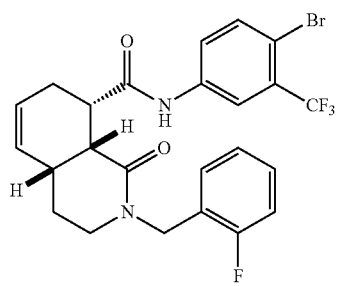

-continued
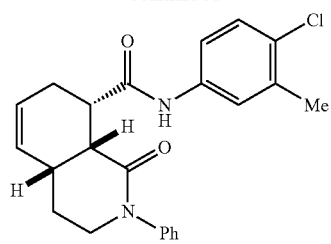
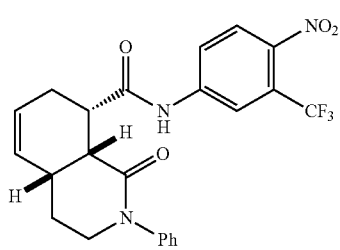
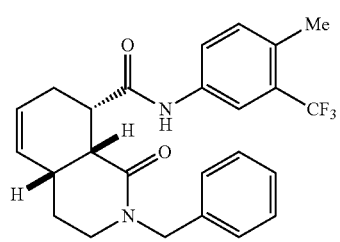
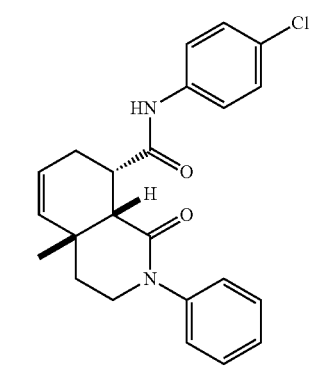
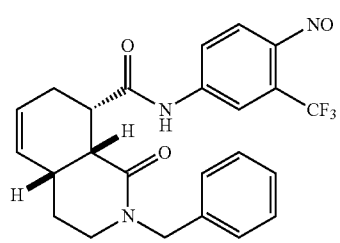
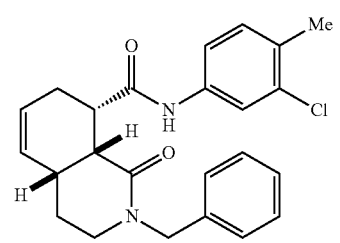
-continued
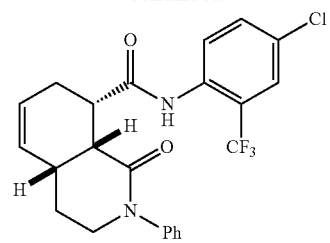
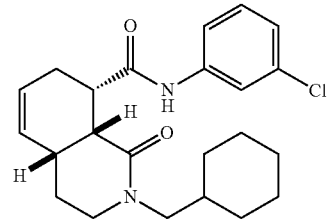
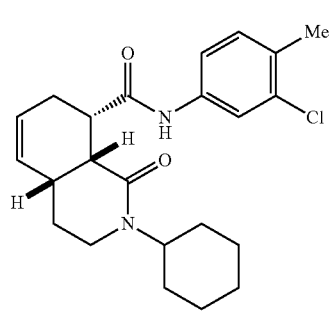
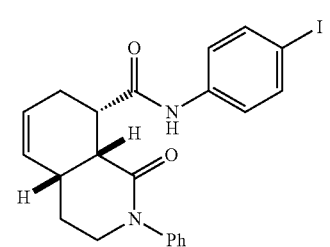
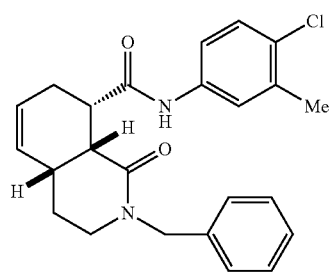
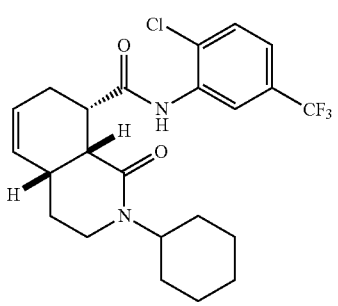

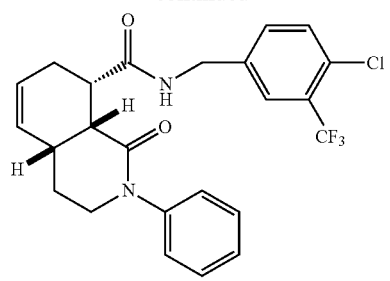
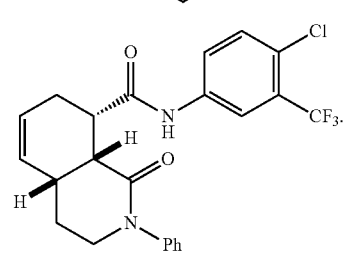
2. A pharmaceutical composition comprising:
a pharmaceutically acceptable carrier; and
compound selected from the group of:
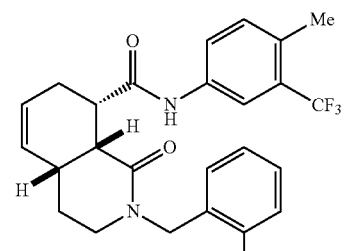
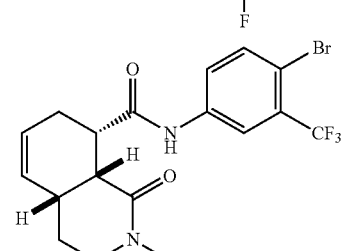
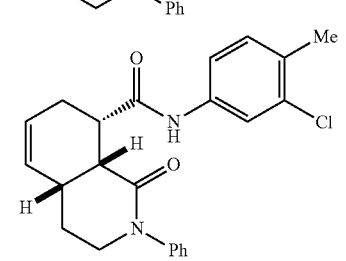
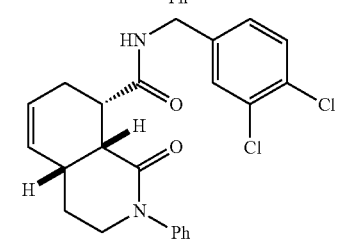
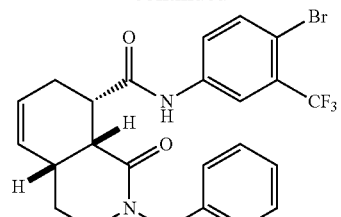
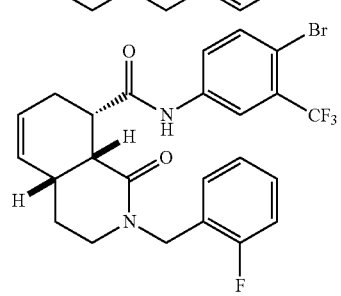
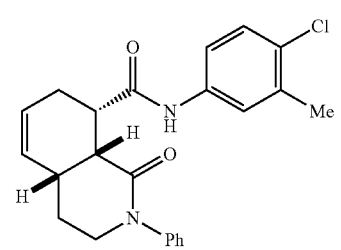
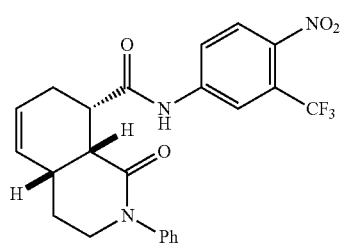 [SMILES: O=C(Nc1ccc(Cl)c(C(F)(F)F)c1)[C@H]1CC=C[C@H]2CCN(c3ccccc3)C(=O)[C@@H]12]
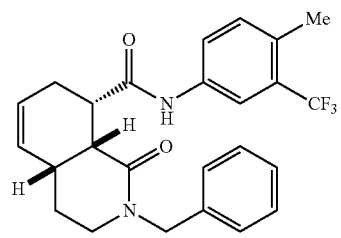
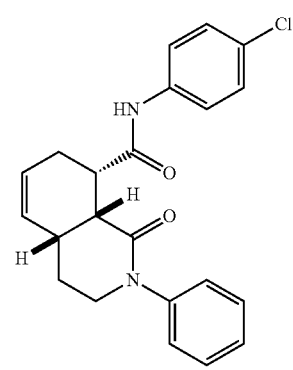

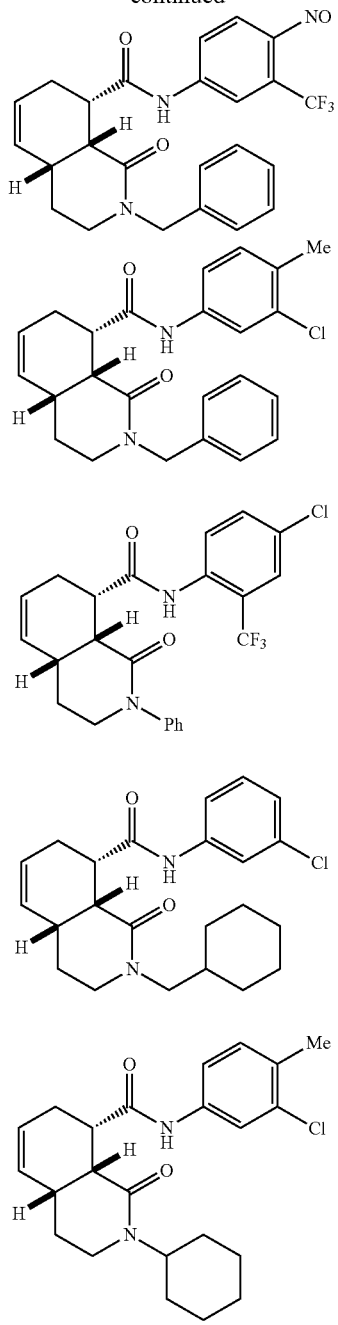
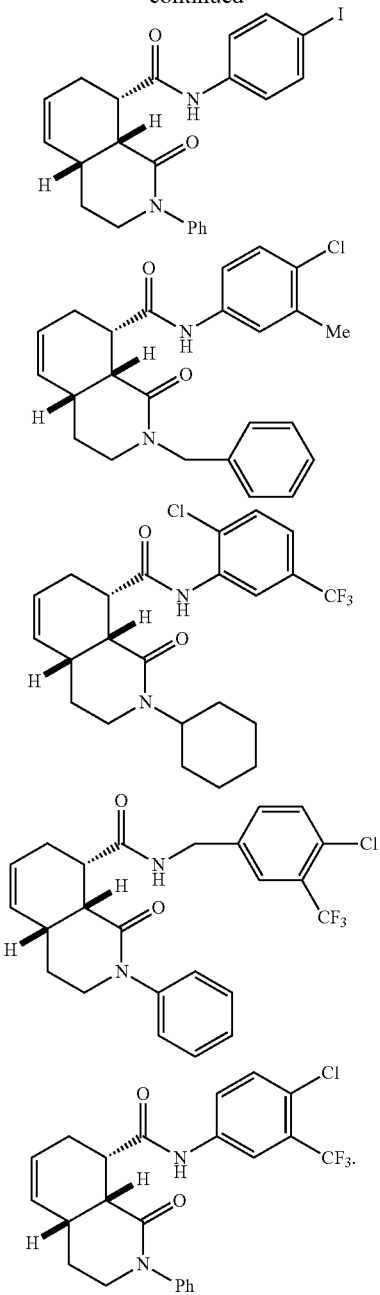
* * * * *